United States Patent
Einav et al.

(10) Patent No.: US 8,895,598 B2
(45) Date of Patent: Nov. 25, 2014

(54) METHODS OF TREATING A FLAVIVIRIDAE FAMILY VIRAL INFECTION, COMPOSITIONS FOR TREATING A FLAVIVIRIDAE FAMILY VIRAL INFECTION, AND SCREENING ASSAYS FOR IDENTIFYING COMPOSITIONS FOR TREATING A FLAVIVIRIDAE FAMILY VIRAL INFECTION

(75) Inventors: Shirit Einav, Los Altos Hills, CA (US); Jeffrey S. Glenn, Palo Alto, CA (US); Robert McDowell, San Francisco, CA (US); Wenjin Yang, Foster City, CA (US); Hadas Dvory-Sobol, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 346 days.

(21) Appl. No.: 12/678,014

(22) PCT Filed: Sep. 18, 2008

(86) PCT No.: PCT/US2008/076804
§ 371 (c)(1), (2), (4) Date: Mar. 12, 2010

(87) PCT Pub. No.: WO2009/039246
PCT Pub. Date: Mar. 26, 2009

(65) Prior Publication Data
US 2010/0260717 A1 Oct. 14, 2010

Related U.S. Application Data

(60) Provisional application No. 60/973,309, filed on Sep. 18, 2007, provisional application No. 61/088,759, filed on Aug. 14, 2008, provisional application No. 61/092,537, filed on Aug. 28, 2008.

(51) Int. Cl.
| | | |
|---|---|---|
| A61K 31/415 | (2006.01) | |
| C07K 14/005 | (2006.01) | |
| A61K 31/67 | (2006.01) | |
| A61K 31/7056 | (2006.01) | |
| A61K 45/06 | (2006.01) | |

(52) U.S. Cl.
CPC ............... C07K 14/005 (2013.01); A61K 31/67 (2013.01); A61K 31/7056 (2013.01); A61K 45/06 (2013.01); G01N 2500/02 (2013.01); G01N 2333/186 (2013.01); C12N 2770/24222 (2013.01)
USPC ....................................................... 514/394

(58) Field of Classification Search
USPC ........................................................ 514/394
See application file for complete search history.

(56) References Cited

U.S. PATENT DOCUMENTS 2,684,327 A 7/1954 Passal et al.
2,689,853 A 9/1954 Schenck et al.
(Continued)

FOREIGN PATENT DOCUMENTS

DE 102007028521 A1 12/2008
EP 1400241 A1 3/2004
(Continued)

OTHER PUBLICATIONS

Voronina et al. "Synthesis and pharmaceutical properties of amidine analogs of pyracetatam," Khimiko-Farmatsevticheskii Zhurnal, 1990, vol. 24, No. 11, pp. 26-29. CAPLUS Abstract. AN 1991:101601.*
(Continued)

Primary Examiner — Shengjun Wang
(74) Attorney, Agent, or Firm — Thomas | Horstemeyer, LLP

(57) ABSTRACT

Briefly described, embodiments of this disclosure include compositions, pharmaceutical compositions, methods of treating a host infected with a virus from the Flaviviridae family of viruses, methods of identifying a candidate agent for the treatment of hepatitis C virus (HCV) infection, and the like.

6 Claims, 16 Drawing Sheets

(56) References Cited

U.S. PATENT DOCUMENTS

| | | | |
|---|---|---|---|
| 3,265,691 | A | 8/1966 | Richter et al. |
| 3,423,413 | A | 1/1969 | Priewe et al. |
| 3,428,634 | A | 2/1969 | Palazzo |
| 4,011,322 | A | 3/1977 | Rahtz et al. |
| 4,269,835 | A * | 5/1981 | Whittle ............................ 514/357 |
| 5,552,426 | A | 9/1996 | Lunn et al. |
| 6,211,177 | B1 | 4/2001 | Sperl et al. |
| 6,476,062 | B2 | 11/2002 | Chu |
| 7,495,015 | B2 | 2/2009 | Arora et al. |
| 2002/0128307 | A1 | 9/2002 | Chu |
| 2004/0092575 | A1 * | 5/2004 | Peuvot et al. .................. 514/424 |
| 2004/0097438 | A1 * | 5/2004 | Hashimoto et al. ............. 514/43 |
| 2004/0224876 | A1 | 11/2004 | Jost-Price et al. |
| 2005/0187261 | A1 | 8/2005 | Verner et al. |
| 2005/0192261 | A1 | 9/2005 | Jost-Price et al. |
| 2006/0052602 | A1 | 3/2006 | Kim et al. |
| 2008/0161324 | A1 | 7/2008 | Johansen |
| 2010/0028299 | A1 | 2/2010 | Einav et al. |

FOREIGN PATENT DOCUMENTS

| | | | |
|---|---|---|---|
| KR | 10-1995-0031074 A | | 12/1995 |
| WO | 0204425 A2 | | 1/2002 |
| WO | 0207761 A1 | | 3/2002 |
| WO | 03060475 A2 | | 7/2003 |
| WO | 2005012288 A1 | | 2/2005 |
| WO | WO 2005/032329 | | 4/2005 |
| WO | 2006010446 A2 | | 2/2006 |
| WO | 2006131737 A2 | | 12/2006 |
| WO | 2006135383 A2 | | 12/2006 |
| WO | WO 2006/131737 | * | 12/2006 |
| WO | 2007103111 A2 | | 9/2007 |
| WO | 2007115077 A2 | | 10/2007 |
| WO | 2007117465 A2 | | 10/2007 |
| WO | 2008033466 A2 | | 3/2008 |
| WO | 2009039248 A2 | | 3/2009 |

OTHER PUBLICATIONS

International Search Report and Written Opinion dated Apr. 1, 2009.
International Search Report and Written Opinion dated Aug. 13, 2009.
Blight, K. J., et al., "Allelic Variation in the Hepatitis C Virus NS4B Protein Dramatically Influences RNA Replication," J. Virology, Jun. 2007, vol. 81, No. 11, pp. 5724-5736.
Einav, S., et al., "A Nucleotide Binding Motif in Hepatitis C Virus (HCV) NS4B Mediates HCV RNA Replication," J. Virology, Oct. 2004, vol. 78, No. 20, pp. 11288-11295.
Puerstinger, G., et al., "Antiviral 2,5-disubstituted Imidazo[4,5-c]pyridines; From Anti-Pestvirus to Anti-Hepatitis C Virus Activity," Bioorganic & Medicinal Chemistry Letters, Jan. 2007, vol. 17., No. 2, pp. 390-393.
Hirashima, S., et al., "Benzimidazole Derivatives Bearing Substituted Biphenyls as Hepatitis C Virus NS5B RNA-Dependent RNA Plymerase Inhibitors: Structure-Activity Relationship Studies and Identification of a Potent and Highly Selective Inhibitor JTK-109," J. Medicinal Chemistry, Jun. 2006, vol. 49, No. 15, pp. 4721-4736.
Korba, B. E., et al., "Nitazoxanide, Tizoxanide and Other Thiazolides are Potent Inhibitors of Hepatitis B Virus and Hepatitis C Virus Replication," Antiviral Research, Sep. 4, 2007, vol. 77. No. 1, pp. 56-63.
Einav, S., et al., "The Hepatitis C Virus (HCV) NS$B RNA Binding Inhibitor Clemizole is Highly Synergistic with HCV Protease Inhibitors," Anti-HCV Drug Synergy with Clemizole, JID 2010:202 (Jul. 1) pp. 65-74.
Cho, et al., "Identification of a Class of HCV Inhibitors Directed Against the Nonstructural Protein NS4B," www.scienceTranslationalMedicine.org, Jan. 20, 2010, vol. 2, Issue 15, pp. 1-8.
Cho, et al., Supplementary Materials for "Identification of a Class of HCV Inhibitors Directed Against the Nonstructural Protein NS4B," www.scienceTranslationalMedicine.org, Jan. 20, 2010, vol. 2, Issue 15, pp. 1-23.
International Search Report and Written Opinion dated Dec. 24, 2010.
International Search Report and Written Opinion dated Dec. 27, 2010.
Selwood, et al., "Synthesis and Biological Evaluation of Novel Pyrazoles and Indazoles as Activators of the Nitric Oxide Receptor, Soluable Guanylate Cyclase," Journal of Medicinal Chemistry, 2001, vol. 44, pp. 78-93.
Patel, et al., "3D QSAR and Molecular Docking Studies of Benzimidazole Derivatives as Hepatitis C Virus NS5B Polymerase Inhibitors," Journal of Chemical Information and Modeling, 2008, vol. 48, pp. 42-55.
Beaulieu, et al., "Benzimidazoles as New Potent and Selective DP Antagonists for the Treatment of Allergic Rhinitis," Bioorganic & Medical Chemistry Letters, 2004, vol. 14, pp. 3195-3199.
Einav, et al., "Discovery of a Hepatitis C Target and its Pharmacological Inhibitors by Microfluidic Affinity Analysis," Nature Biotechnology, Sep. 2008, vol. 26, No. 9, pp. 1019-1027.
Blight, et al.; Efficient Initiation of HCV RNA Replication in Cell Culture; Science; vol. 290; Dec. 8, 2009, 19721974.
Einav, et al.; A Nucleotide Binding Motif in Hepatitis C Virus (HCV) NS4B Mediates HCV RNA Replication; Journal of Virology; Oct. 2004; vol. 78, No. 20; pp. 1128-11295.
Hwang, et al.; Inhibition of Hepatitis C Virus Replication by Arsenic Trioxide; Antimicrobial Agents and Chemotheraphy; vol. 48, No. 8; Aug. 2004; p. 2876-2882.
Lohmann, et al.; Replication of Subgenomic Hepatitis C Virus RNAs in a Hepatoma Cell Line; Science; vol. 285; Jul. 2, 1999; pp. 110-113.
Maerkl, et al.; A Systems Approach to Measuring the Binding Energy Landscapes of Transcription Factors; Science; vol. 315; Jan. 12, 2007; pp. 233-237.
Takhampunya, et al.; Inhibition of Dengue Virus Replication by Mycophenolic Acid and Ribavirin; Journal of General Virology; vol. 87; 2006; 1947-1952.
Supplemental European Search Report dated Oct. 13, 2011.
Beaulieu, P.L., et al., "Non-nucleoside Inhibitors of the Hepatitis C Virus NS5B polymerase: Discovery and Preliminary SAR of Benzimidazolde Derivatives," Bioorganic & Medicinal Chemistry Letters, Pergamon, Elsevier Science, GB, vol. 14, No. 1, Jan. 1, 2004, pp. 119-124.
Beaulieu, P.L., et al., "Improved Replicon Cellular Activity of Non-Nucleoside Allosteric Inhibitors of HCV NS5B Polymerase: From Benzimidazole to Indole Scaffolds," Bioorganic & Medicinal Chemistry Letters, Pergamon, Elsevier Science, GB, vol. 16, No. 19, Oct. 1, 2006, pp. 4987-4993.
"Martindale, The Complete Drug Reference", 2000, Pharmaceutical Press, XP000002659125, Clemizole Hydrocholoride, p. 406.
Einav, Shirit, et al., "Discovery of a Hepatitis C Target and its Pharmacological Inhibitors of Microfluidic Affinity Analysis," Nature Biotechnology, Nature Publishing Group, NY, vol. 26, No. 9, Sep. 1, 2008, pp. 1019-1027.
Office Action dated Sep. 9, 2013 for Chinese Application Serial No. 201080021845.9, 4 pages.
Office Action dated Sep. 11, 2013 for Chinese Application Serial No. 201080021850.X, 3 pages.
Supplemental European Search Report dated Jul. 2, 2012.
Supplemental European Search Report dated Aug. 8, 2012.
Einav, et al., Discovery of a Hepatitis C Target and its Pharmacological Inhibitors by Microfluidic Affinity Analysis, Nature Biotechnology, Nature Publishing Group, New York, NY, vol. 26, No. 9, Sep. 1, 2008, pp. 1019-1027.
Caroti, et al., "Synthesis, Antilipidemic and Platelet Antiaggregatory Activity of 2-Aminobenzimidazole Amide Derivatives," II Farmaco, Elsevier France, Scientifiques Et Medicals, IT, vol. 44, No. 3, Jan. 1, 1989, pp. 227-255.
Tuncbilek, et al., "Synthesis and Antimicrobial Activity of Some New Anilino Benzimidazoles," Archiv Der Pharmazie, Wiley, VH Verlag GmBH & Co. KGAA, Dec. 1, 1997, pp. 372-376.
Manganaro, et al., "Activity of Antiinflammatory Steroidal and Nonsteroidal Compounds in Some Experimental Functions, II, Activity of Certain Nonsteroidal Antiinflammatory Agents as Compared with that of Prednisone in Murine Hepatitis Due to MHV3,"

(56) References Cited

OTHER PUBLICATIONS

Inflammation, Plenum Press, New York, NY, vol. Proc. Int. Symp. No. 1968, Jan. 1, 1968, pp. 67-71.
Anonymous, Registry, Dec. 8, 2008, XP007920913.
Anonymous, Registry, Dec. 18, 1984-Dec. 22, 2009, XP007920912.
Anonymous, Registry, Nov. 8, 2004, XP007920909.
Testa; "Prodrug research: futile or fertile?", 2004, Biochemical Pharmacology; 68:2097-2106.
Patani et al. Bioisosterism: A Rational Approach in Drug Design. Chem. Rev. 1996. vol. 96, pp. 3147-3176.
Supplementary European Search Report dated Sep. 19, 2011.
Iacobellis et al. "External validation of biochemical indices for noninvasive evaluation of liver fibrosis in HCV chronic Hepatitis". American Journal of Gastroenterology, 2005, vol. 100, pp. 868-873.
Echeverri, A.C. & Dasgupta, A. Amino Terminal Regions of Poliovirus 2C Protein Mediate Membrane Binding. Virology, 1995. vol. 208, pp. 540-553.
Rodriguez, P.L. & Carrasco L. Poliovirus Protein 2C Contains Two Regions Involved in RNA Binding Activity. J. Biol. Chem. 1995, vol. 270 (17), pp. 10105-10112.
Hadd, A.D. et al. Microchip Device for Performing Enzyme Assays. Anal. Chem. 1997, vol. 69, pp. 3407-3412.
El-Hage, N. & Luo, G. Replication of Hepatitis C Virus RNA Occurs in a Membrane-Bound Replication Complex Containing Nonstructural Viral Proteins and RNA. Journal of General Virology, 2003, vol. 84, pp. 2761-2769.
Park-Lee et al. Characterization of the Interaction between Neuronal RNA-binding Protein HuD and AU-rich RNA. Journal of Biological Chemistry, 2003, vol. 278(41) pp. 39801-39808.
Einav, S. et al. A Nucleotide Binding Motif in Hepatitis C Virus (HCV) NS4B Mediates HCV RNA Replication. Journal of Virology, 2004, vol. 78(20) pp. 11288-11295.
Lundin, M et al. Topology of the Membrane-Associated Hepatitis C Virus Protein NS4B. Journal of Virology, 2003, vol. 77(9), pp. 5428-5438.
Gosert, R. et al. Identification of the Hepatitis C Virus RNA Replication Complex in Huh-7 Cells Harboring Subgenomic Replicons. Journal of Virology, 2003, vol. 77(9), pp. 5487-5492.
Tscherne, D.M. Time- and Temperature-Dependent Activation of Hepatitis C Virus for Low-pH-Triggered Entry. Journal of Virology, 2006, vol. 80(4), pp. 1734-1741.
Elazar, M. et al. An N-Terminal Amphipathic Helix in Hepatitis C Virus (HCV) NS4B Mediates Membrane Association, Correct Localization of Replication Complex Proteins, and HCV RNA Replication. Journal of Virology, 2004, vol. 78(20), pp. 11393-11400.
Dimitrova M. et al. Protein-Protein Interactions between Hepatitis C Virus Nonstructural Proteins. Journal of Virology, 2003, vol. 77(9), pp. 5401-5414.
Glenn J.S. et al. In Vitro-Synthesized Hepatitis Delta Virus RNA Initiates Genome Replication in Cultured Cells. Journal of Virology, 1990, vol. 64(6), pp. 3104-3107.
Huang L. et al. Hepatitis C Virus Nonstructural Protein 5A (NS5A) Is an RNA-binding Protein. Journal of Biological Chemistry, 2005, vol. 280(43) pp. 36414-36428.
Elazar, M. et al. Amphipathic Helix-Dependent Localization of NS5A Mediates Hepatitis C Virus RNA Replication. Journal of Virology, 2003, vol. 77(70), pp. 6055-6061.
Egger D. et al. Expression of Hepatitis C Virus Proteins Induces Distinct Membrane Alterations Including a Candidate Viral Replication Complex. Journal of Virology, 2002, vol. 76(12), pp. 5974-5984.
Kang L. et al. Microfluidics for drug discovery and development: From target selection to product lifecycle management. Drug Discovery Today, 2008, vol. 13 (1/2), pp. 1-13.
Kusov YY. et al. Membrane association and RNA binding of recombinant hepatitis A virus protein 2C. Arch Virol. 1998, vol. 143, pp. 931-944.
Liang, T.J. et al. Pathogenesis, Natural History, Treatment, and Prevention of Hepatitis C, Ann. Intern. Med., 2000, vol. 132, pp. 296-305.
Park, S. et al. HuD RNA Recognition Motifs Play Distinct Roles in the Formation of a Stable Complex with AU-Rich RNA. Mol. Cell. Biol. 2000, vol. 20(13), pp. 4765-4772.
Lee, N.L. et al. Solvent Compatibility of Poly(dimethylsiloxane)-Based Microfluidic Devices. Anal. Chem., 2003, vol. 75, pp. 6544-6554.
Roosild, T.P. et al. NMR Structure of Mistic, a Membrane-Integrating Protein for Membrane Protein Expression. Science, 2005, vol. 307, pp. 1317.
Reed K.E. & Rice C.M. Overview of Hepatitis C Virus Genome Structure, Polyprotein Processing, and Protein Properties. The Hepatitis C Viruses, Current Topics in Microbiology and Immunology, 2000, vol. 242, pp. 55-84.
Overington, J.P. et al. How many drug targets are there? Nat Rev Drug Discov. 2006, vol. 5, pp. 993-996.
Maerkl, SJ. et al. A Systems Approach to Measuring the Binding Energy Landscapes of Transcription Factors. Science, 2007, vol. 315, pp. 233-237.
Toepke, MW, et al. PDMS absorption of small molecules and consequences in microfluidic applications. Lab on a Chip, 2006, vol. 6, pp. 1484-1483.
Whitesides, GM. The origins and the future of microfluidics. Nature 2006, vol. 442, pp. 368-373.
Myer, VE et al. Identification of HuR as a protein implicated in AUUUA-mediated mRNA decay. The EMBO Journal, 1997, vol. 16, pp. 2130-2139.
Glenn, JS. et al. In Vitro-Synthesized Hepatitis Delta Virus RNA Initiates Genome Replication in Cultured Cells. Journal of Virology, 1990, vol. 64(6), pp. 3104-3107.
Glenn, JS et al. Identification of a Prenylation Site in Delta Virus Large Antigen. Science, 1992, vol. 256, pp. 1331-1333.
Burd, CG & Dreyfuss G. Conserved Structures and Diversity of Functions of RNA-Binding Proteins. Science, 1994, vol. 265, pp. 615-621.
Wung, CH et al. Identification of the RNA-binding sites of the triple gene block protein 1 of bamboo mosaic potexvirus. J. Gen. Virol. 1999, vol. 80, pp. 1119-1126.
Spangberg, K et al. HuR, a Protein Implicated in Oncogene and Growth Factor mRNA Decay, Binds to the 39 Ends of Hepatitis C Virus RNA of Both Polarities. Virology, 2000, vol. 274, pp. 378-390.
Lindenbach et al. Complete Replication of Hepatitis C Virus in Cell Culture. Science, 2005, vol. 309, pp. 623-626.
Tong X et al. Identification and analysis of fitness of resistance mutations against the HCV protease inhibitor SCH 503034. Antiviral Research, 2006, vol. 70, pp. 28-38.
Blight KJ et al. Efficient Initiation of HCV RNA Replication in Cell Culture. Science, 2000, vol. 290, pp. 1972-1974.
Schilders G. et al. MPP6 is an exosome-associated RNA-binding protein involved in 5.8S rRNA maturation. Nucleic Acids Research, 2005, vol. 33(21), pp. 6795-6804.

* cited by examiner 3 male, HCV genotype 4 patients:

| | Baseline | week 2 | week 4 | week 8 |
|---|---|---|---|---|
| #1 24 y.o., ALT 59 | 290,000 | 190,000 | 2,400 | <10 |
| #2 27y.o., ALT 124 | 730,000 | 320,000 | <10 | <10 |
| #3 32y.o., ALT 99 | 489,000 | 70,000 | <10 | <10 |

Normal ALT = <45

100 BID clemizole X 8 weeks
180 ug/wk pegasys on weeks 4-8
Continued on NTZ + pegasys Upper: HCV 5'-UTR positive strand (SEQ ID NO. 1); GenBank NC_004102; nt 1-341
5'UTR
Lower: HCV 3'UTR negative strand (SEQ ID NO. 2)
For genotype 1a

```
  5'   1 gccagccccc tgatggggc gacactccac catgaatcac tcccctgtga ggaactactg
         cggucggggg acuacccccg cugugaggug guacuuagug aggggacacu ccuugaugac 61 tcttcacgca gaaagcgtct agccatggcg ttagtatgag tgtcgtgcag cctccaggac
         agaagugcgu cuuucgcaga ucgguaccgc aaucauacuc acagcacguc ggagguccug 121 cccccctccc gggagagcca tagtggtctg cggaaccggt gagtacaccg gaattgccag
         gggggagggg cccucucggu aucaccagac gccuuggcca cucaugugc cuuaacgguc 181 gacgaccggg tcctttcttg gataaacccg ctcaatgcct ggagatttgg gcgtgccccc
         cugcuggccc aggaaagaac cuauuugggc gaguuacgga ccucuaaacc cgcacggggg 241 gcaagactgc tagccgagta gtgttgggtc gcgaaaggcc ttgtggtact gcctgatagg
         cguucugacg aucggcucau cacaacccag cgcuuuccgg aacaccauga cggacuaucc 301 gtgcttgcga gtgccccggg aggtctcgta gaccgtgcac c
         cacgaacgcu cacggggccc uccagagcau cuggcacgug g 5'
```

(SEQ ID NO. 3)

5' UTR pos (For genotype 1b)
agacccaagctggctagcgtttaaacttaagcttggtaccgagctcggatccactagtccagtgtggtggaattctgca
gatatcataatacgactcactatagccagccccgattggggcgacactccaccatagatcactcccctgtgaggaac
tactgtcttcacgcagaaagcgtctagccatggcgttagtatgagtgtcgtgcagcctccaggaccccccctcccggga
gagccatagtggtctgcggaaccggtgagtacaccggaattgccaggacgaccgggtcctttcttggatcaacccgctc
aatgcctggagatttgggcgtgccccgcgagactgctagccgagtagtgttgggtcgcgaaaggccttgtggtactgc
ctgatagggtgcttgcgagtgccccgggaggtctcgtagaccgtgcaccatgagcacgaatcctaaacctcaaagaaaa
accaaagggcgcgccatggatcgatatccagcacagtggcggccgctcgagt (SEQ ID NO. 4)

3' UTR neg (For genotype 1b)
acucgagcggccgccacugugcuggauaucgauccauggcgcgcccuuugguuuuucuuugagguuuaggauucgugcu
cauggugcacggucuacagagaccucccggggcacucgcaagcaccuaucaggcaguaccacaaggccuuucgcgaccc
aacacuacucggcuagcagucucgcggggcacgcccaaaucuccaggcauugagcggguugauccaagaaaggacccg
gucguccuggcaauuccggguguacucaccgguuccgcagaccacuaugcucucccgggaggggggguccuggaggcug
cacgacacucauacuaacgccauggcuagacgcuuucugcgugaagacaguaguuccucacaggggagugaucuaugu
ggagugucgccccaaucggggcuggcuauagugagucguauuaugauaucugcagaauuccaccacacuggacuagu
ggauccgagcucgguaccaagcuuaaguuuaaacgcuagccagcuuggggucu
```

FIG. 3

Preparation of 5, 6-Disubstituted
Chemizoles Compounds

//METHODS OF TREATING A FLAVIVIRIDAE FAMILY VIRAL INFECTION, COMPOSITIONS FOR TREATING A FLAVIVIRIDAE FAMILY VIRAL INFECTION, AND SCREENING ASSAYS FOR IDENTIFYING COMPOSITIONS FOR TREATING A FLAVIVIRIDAE FAMILY VIRAL INFECTION

CROSS-REFERENCE TO RELATED APPLICATION

This application claims priority to "METHODS OF TREATING A FLAVIVIRIDAE FAMILY VIRAL INFECTION, COMPOSITIONS FOR TREATING A FLAVIVIRIDAE FAMILY VIRAL INFECTION, AND SCREENING ASSAYS FOR IDENTIFYING COMPOSITIONS FOR TREATING A FLAVIVIRIDAE FAMILY VIRAL INFECTION," having serial number PCT/US2008/76804, filed on Sep. 18, 2008. This application claims priority to and the benefit of the following U.S. provisional applications: U.S. Provisional No. 60/973,309, filing date Sep. 18, 2007, U.S. Provisional No. 61/088,759, filed on Aug. 14, 2008 and U.S. Provisional No. 61/092,537, filing date Aug. 28, 2008; which are entirely incorporated herein by reference.

STATEMENT REGARDING FEDERALLY SPONSORED RESEARCH OR DEVELOPMENT

This invention was made with Government support under contract DK066793 awarded by the National Institutes of Health. The Government has certain rights in this invention.

BACKGROUND

Over 150 million people are infected with Hepatitis C Virus (HCV) worldwide. Unfortunately, many of these individuals are unable to clear their infection with the current standard of care, which consists of treatment with a combination of interferon and ribavirin. Moreover, this treatment is associated with significant side effects, precluding its use by many individuals. Thus, current therapies are inadequate for the majority of the patients, and there is a pressing need for new drugs to treat HCV infection (See, Annals Internal Med. 132:296).

The 9.6-kb positive single-stranded RNA HCV genome encodes a 3,000-amino-acid polyprotein which is proteolytically processed into structural proteins, which are components of the mature virus, and nonstructural proteins (NS), which are involved in replicating the viral genome (Curr Top Microbiol Immunol 242, 55-84 (2000)). Like other positive strand RNA viruses (B. N. Fields, D. M. Knipe, and P. M. Howley (ed.), Fields Virology. (Lippincott-Raven Publications, Philadelphia, Pa., 1996, in "The viruses and their replication")), HCV appears to replicate in association with intracellular membrane structures. In the case of HCV, the structures are termed the membranous web (J Virol 76, 5974-5984 (2002)) and are believed to be induced by the NS4B protein. NS4B is also required to assemble the other viral NS proteins within the apparent sites of RNA replication (J Virol 78, 11393-11400 (2004)). It is not known how viral RNA, especially the negative strand template required for production of progeny genomes, might be incorporated or maintained at these replication sites.

There is an ongoing need in the art for agents that treat HCV infection; and for methods of identifying candidate agents that are suitable for treating HCV infection.

SUMMARY

Briefly described, embodiments of this disclosure include compounds, compositions, pharmaceutical compositions, methods of treating a host infected with a virus from the Flaviviridae family of viruses, methods of identifying a candidate agent for the treatment of hepatitis C virus (HCV) infection, and the like.

One exemplary method of treating a host infected with a virus from the Flaviviridae family of viruses, among others, includes: administering to the host a therapeutically effective amount of an inhibiting agent to reduce the viral load in the host. In an embodiment, the inhibiting agent is selected from the group consisting of clemizole, a clemizole analog, and a compound having a clemizole scaffold; an H1 antagonist, an H1 receptor antagonist that shares structural similarity with clemizole; cinoxacin, a cinoxacin analog, and a compound having a cinoxacin scaffold; norepinephrine, a norepinephrine analog, and a compound having a norepinephrine scaffold; glybenclamide, a glybenclamide analog, and a compound having a glybenclamide scaffold; spiradoline, a spiradoline analog, and a compound having a spiradoline scaffold; tropicamide, a tropicamide analog, and a compound having a tropicamide scaffold, pharmaceutical salts of each of these compounds, isosteres of each of these compounds, and a combination thereof.

One exemplary method of identifying a candidate agent for the treatment of hepatitis C virus (HCV) infection, among others, includes: admixing a test agent with i) an HCV NS4B polypeptide that binds HCV 3'UTR negative strand nucleic acid; and ii) a nucleic acid comprising an HCV 3'UTR negative strand polynucleotide; and b) determining the effect, if any, of the test agent on the binding of NS4B to the HCV 3'UTR negative strand nucleic acid, wherein a test agent that inhibits binding of NS4B to the HCV 3'UTR negative strand nucleic acid is a candidate agent for the treatment of HCV infection.

One exemplary pharmaceutical composition, among others, includes: an inhibiting agent. In an embodiment, the inhibiting agent is selected from the group consisting of: a clemizole analog, and a compound having a clemizole scaffold; an H1 antagonist, an H1 receptor antagonist that shares structural similarity with clemizole; cinoxacin, a cinoxacin analog, and a compound having a cinoxacin scaffold; norepinephrine, a norepinephrine analog, and a compound having a norepinephrine scaffold; glybenclamide, a glybenclamide analog, and a compound having a glybenclamide scaffold; spiradoline, a spiradoline analog, and a compound having a spiradoline scaffold; tropicamide, a tropicamide analog, and a compound having a tropicamide scaffold, pharmaceutical salts of each of these compounds isosteres of each of these compounds, and a combination thereof.

BRIEF DESCRIPTION OF THE DRAWINGS

FIG. 3 illustrate RNA strands for 5' untranslated region of the HCV positive strand RNA genome and the 3' untranslated region of the HCV negative strand RNA.

DETAILED DESCRIPTION

Figure 1A:
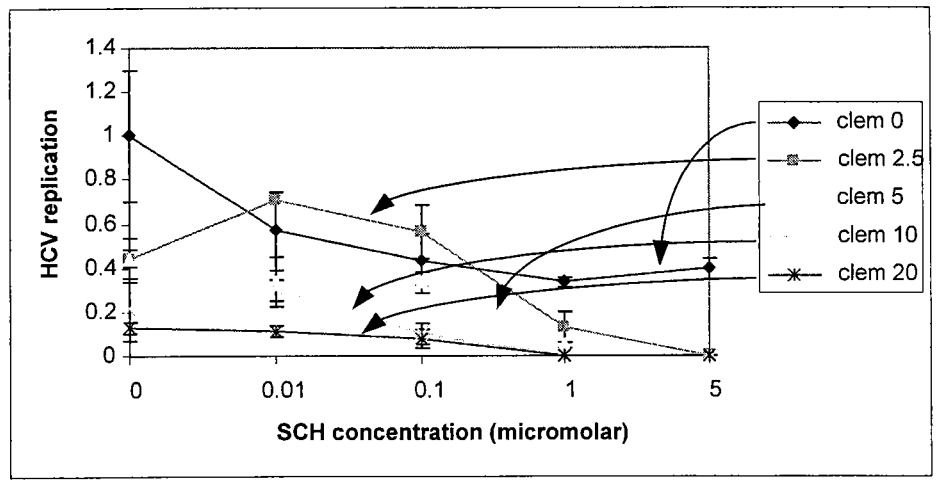
FIGS. 1A and 1B HCV show graphs illustrating data from replication assays employing a luciferase reporter-linked HCV genome in the presence of various combinations of clemizole and an NS3 protease inhibitor (SCH503034).

Before the present disclosure is described in greater detail, it is to be understood that this disclosure is not limited to particular embodiments described, and that the various embodiments of the invention may, of course, vary. It is also to be understood that the terminology used herein is for the purpose of describing particular embodiments only, and is not intended to be limiting, because the scope of the present disclosure is to be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes both a single compound and a plurality of compounds. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

By "Flaviviridae virus" is meant any virus of the Flaviviridae family, including those viruses that infect humans and non-human animals. The polynucleotide and polypeptides sequences encoding these viruses are well known in the art, and may be found at NCBI's GenBank database, e.g., as Genbank Accession numbers NC_004102, AB031663, D11355, D11168, AJ238800, NC_001809, NC_001437, NC_004355 NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety.

As used herein, the terms "determining," "measuring," "assessing," and "assaying" are used interchangeably and include both quantitative and qualitative determinations.

As used herein, the term "micro-fluidic" device refers to any device in which micro-volumes of fluid are manipulated along a fluid flow path during any given use or operation, e.g., sample preparation, sample separation, chemical synthesis, sample binding, sample washing, etc., where "micro-volume" means from about 10 femtoliters to 500 µl, e.g., from about 100 femtoliters to about 200 µl. The micro-fluidic devices contain at least one fluid flow path through which fluid flows through the device, where a plurality of flow paths that may or may not be intersecting and may be positioned in any convenient configuration may be present in the device. Generally, the micro-fluidic device with which the subject methods are practiced has at least one micro-compartment positioned at some point in the fluid flow path, where the term "micro-compartment" means any type of structure in which micro-volumes of fluid may be contained, and includes micro-chambers, micro-channels, micro-conduits and the like. Depending on the nature of the micro-compartment, the micro-compartment may be the entire fluid flow path through the device, e.g., where the fluid flow path is a micro-channel, or occupy only a portion of the fluid flow path of the device. The term micro-chamber, as used herein, means any structure or compartment having a volume ranging from about 1 µl to 500 µl, having cross-sectional areas ranging from about 0.05 $cm^2$ with a chamber depth of 200 µm to 5 $cm^2$ with a chamber depth of 1 mm; e.g., from about 10 µl to 500 µl, having a cross-sectional area ranging from about 0.5 $cm^2$ with a chamber depth of 200 µm to about 5 $cm^2$ with a chamber depth of 1 mm; or from about 20 µl to 200 µl, having a cross-sectional area ranging from about 1 $cm^2$ with a chamber depth of 200 µm to about 4 $cm^2$ with a chamber depth of 500 µm. The micro-compartment structure may have any convenient configuration, including square, circular, rectangular, octagonal, irregular, etc. Micro-channels or micro-conduits are micro-compartments that are dimensioned or configured such that fluid is capable of flowing through the micro-channel by capillary flow, i.e., the micro-channel is of capillary dimensions. By capillary dimensions is meant a structure or container in which any cross-sectional dimension from one side to another, e.g., diameter, widest point between two walls of a channel, etc., does not exceed about 250 µm. Any cross-sectional dimension of the micro-channel can range from about 10 to 250 µm, usually from about 50 to 200 µm. The flow through the micro-channels may also be pressurized.

The terms "polypeptide" and "protein", used interchangeably herein, refer to a polymeric form of amino acids, of any number greater than three, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides, of any number greater than three, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. Isolated compounds are usually at least about 80%, at least 90% pure, at least 98% pure, or at least about 99% pure, by weight. The present disclosure encompasses diastereomers as well as their racemic and resolved, enantiomerically pure forms and pharmaceutically acceptable salts thereof.

"Operably linked" refers to an arrangement of elements wherein the components so described are configured so as to perform their usual function. For example, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

As used herein, the terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (b) impeding the development of the disease, and (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (e.g., reduction of pathogen load, reduction of disease symptoms, etc.).

As used herein, the terms "prophylactically treat" or "prophylactically treating" refers completely or partially preventing a disease or symptom thereof and/or may be therapeutic in terms of a partial or complete cure for a disease and/or adverse effect attributable to the disease.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host, including any organism or those animals noted above that are alive. The term "living host" refers to the entire host or organism and not just a part excised (e.g., a liver or other organ) from the living host.

The term "unit dosage form," as used herein, refers to physically discrete units suitable as unitary dosages for human and animal subjects, each unit containing a predetermined quantity of a compound (e.g., an anti-viral compound as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more such excipients, diluents, carriers, and adjuvants.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, inhalation, and the like.

The term "therapeutically effective amount" as used herein refers to that amount of an embodiment of the inhibiting agent being administered that will relieve to some extent one or more of the symptoms of the condition, such as a viral infection being treated and/or that amount that will prevent, to some extent, one or more of the symptoms of the condition that the host being treated has or is at risk of developing.

"Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed inhibiting agents form salts, these salts are within the scope of the present disclosure. Reference to an inhibiting agent of any of the formulas herein is understood to include reference to salts thereof, unless otherwise indicated. The term "salt(s)", as employed herein, denotes acidic and/or basic salts formed with inorganic and/or organic acids and bases. In addition, when an inhibiting agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of agents that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the agents described in the instant disclosure are also contemplated herein.

To the extent that the disclosed active agents (compounds, and salts thereof), may exist in their tautomeric form, all such tautomeric forms are contemplated herein as part of the present disclosure.

All stereoisomers of the agents, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of a compound described herein may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of an agent that is converted into a biologically active form in vivo. Prodrugs are often useful because, in some situations, they may be easier to administer than the parent compound. They may, for instance, be bioavailable by oral administration whereas the parent compound is not or is less so. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing a compound into a host. Preferred routes of administration of the compounds of embodiments of the invention include oral administration and intravenous administration. However, any route of administration, such as topical, subcutaneous, peritoneal, intraarterial, inhalation, vaginal, rectal, nasal, introduction into the cerebrospinal fluid, or instillation into body compartments, can be used.

The term "aliphatic group" refers to a saturated or unsaturated linear or branched hydrocarbon group and encompasses alkyl, alkenyl, and alkynyl groups, for example.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, n-octyl, dodecyl, octadecyl, amyl, 2-ethylhexyl, and the like. The term "substituted alkyl" refers to alkyl groups substituted with one or more groups, preferably selected from aryl, substituted aryl, heterocyclo, substituted heterocyclo, carbocyclo, substituted carbocyclo, halo, hydroxy, protected hydroxy, alkoxy (e.g., C1 to C7) (optionally substituted), acyl (e.g., C1 to C7), aryloxy (e.g., C1 to C7) (optionally substituted), alkylester (optionally substituted), arylester (optionally substituted), alkanoyl (optionally substituted), aryol (optionally substituted), carboxy, protected carboxy, cyano, nitro, amino, substituted amino, (monosubstituted)amino, (disubstituted)amino, protected amino, amido, lactam, urea, urethane, sulfonyl, etc.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. The term "substituted alkenyl" refers to alkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The term "alkynyl" refers to straight or branched chain hydrocarbon groups having 2 to 12 carbon atoms, preferably 2 to 4 carbon atoms, and at least one triple carbon to carbon bond, such as ethynyl. The term "substituted alkynyl" refers to alkynyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The term "alkoxy" refers to an alkyl group linked to oxygen thus: R—O—. In this function, R represents the alkyl group. An example would be the methoxy group $CH_3O$—.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" refers to a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" refers to the above-defined cycloalkyl group substituted by an above defined alkyl group. Examples of such a group include (cyclohexyl)methyl, 3-(cyclopropyl)-n-propyl, 5-(cyclopentyl)hexyl, 6-(adamantyl) hexyl, and the like.

The term "substituted phenyl" refers to a phenyl group substituted with one or more moieties, and in some instances one, two, or three moieties, chosen from the groups consisting of halogen, hydroxy, protected hydroxy, cyano, nitro, trifluoromethyl, C1 to C7 alkyl, C1 to C7 alkoxy, C1 to C7 acyl, C1 to C7 acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—(C1 to C6 alkyl)carboxamide, protected N—(C1 to C6 alkyl)carboxamide, N,N-di(C1 to C6 alkyl)carboxamide, trifluoromethyl, N—((C1 to C6 alkyl)sulfonyl)amino, N-(phenylsulfonyl)amino or phenyl, substituted or unsubstituted, such that, for example, a biphenyl or naphthyl group results.

Examples of the term "substituted phenyl" include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" refers to one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl) n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynaphth-2-yl)methyl and the like.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, etc., where optionally one or more pair of substituents together with the atoms to which they are bonded form a 3 to 7 member ring.

The term "heteroaryl" refers to optionally substituted five-membered or six-membered rings that have 1 to 4 heteroatoms, such as oxygen, sulfur and/or nitrogen atoms, in particular nitrogen, either alone or in conjunction with sulfur or oxygen ring atoms. Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings can include from one to three halo, trihalomethyl, amino, protected amino, amino salts, monosubstituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a C1 to C4 alkoxy group, similarly, "lower alkylthio" means a C1 to C4 alkylthio group.

The terms "heterocycle", "heterocyclic", "heterocyclic group" or "heterocyclo" refer to fully saturated or partially unsaturated or completely unsaturated, including aromatic ("heteroaryl") or nonaromatic cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, etc., where optionally one or more pair of substituents together with the atoms to which they are bonded form a 3 to 7 member ring.

The term "alkanoyl" refers to an alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

The term "(monosubstituted)amino" refers to an amino group with one substituent preferably chosen from the group consisting of phenyl, substituted phenyl, alkyl, substituted alkyl, C1 to C4 acyl, C2 to C7 alkenyl, C2 to C7 substituted alkenyl, C2 to C7 alkynyl, C7 to C16 alkylaryl, C7 to C16 substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, C1 to C7 acyl, C2 to C7 alkenyl, C2 to C7 alkynyl, C7 to C16 alkylaryl, C7 to C16 substituted alkylaryl and heteroaryl. The two substituents can be the same or different.

The term "heteroaryl(alkyl)" refers to an alkyl group as defined above, substituted at any position by a heteroaryl group, as above defined.

"Isosteres" are different atoms, molecules, or ions that have different molecular formulae but have similar or identical outer shell electron arrangements and also have similar properties (e.g., pharmacological properties (e.g., pharmacokinetic and pharmacodynamic)).

Discussion

Embodiments of the present invention provide methods of treating a Flaviviridae family viral infection, compositions (including inhibiting agents and combinations of agents) for treating a Flaviviridae family viral infection, and screening assays for identifying compositions for treating a Flaviviridae family viral infection. In particular, embodiments of the present invention provide for methods of treating infections caused by Hepatitis C virus and compositions for treating infections caused by Hepatitis C virus.

Embodiments of the present invention provide compositions (including pharmaceutical compositions) including an agent that can be used to treat a host being infected by a Flaviviridae family viral infection, which may be referred to herein as an "inhibiting agent". In particular, the inhibiting agent can be used to treat hosts infected with Hepatitis C virus. The inhibiting agent can be in one or more of the following groups: clemizole, clemizole analogs, and compounds having a clemizole scaffold; H1 antagonists, H1 receptor antagonists that share structural similarity with clemizole; cinoxacin, cinoxacin analogs, and compounds having a cinoxacin scaffold; norepinephrine, norepinephrine analogs, and compounds having a norepinephrine scaffold; glybenclamide, glybenclamide analogs, and compounds having a glybenclamide scaffold; spiradoline, spiradoline analogs, and compounds having a spiradoline scaffold; tropicamide, tropicamide analogs, and compounds having a tropicamide scaffold; one of the other inhibiting agents or their analogs noted below; pharmaceutical salts of each of these compounds; and isosteres of any of the foregoing; and the like, all as described in more detail below.

Embodiments of the present invention also provide in vitro methods of identifying agents that inhibit binding of HCV NS4B to HCV RNA. Embodiments of the present invention provide methods of treating an HCV infection in a host, which methods generally involve administering to the host an inhibiting agent that inhibits binding of NS4B to HCV RNA in an amount therapeutically effective to reduce viral load in the host.

As described in Example 1, it has been observed that HCV NS4B binds to the 3'-UTR of HCV RNA. Certain methods of embodiments of the invention exploit this interaction to provide a means to identify inhibiting agents that interfere with the interaction and thus are candidates for development as agents for treating HCV infection. Thus, embodiments of the present invention provide screening assays to identify inhibiting agents that inhibit NS4B binding to the 3'-UTR of HCV.

Inhibiting agents identified by an embodiment of the screening method, including the inhibiting agents discussed below, are candidates for development as drugs for treating viral infections, where the virus is an NS4B-encoding virus. NS4B encoding viruses include Flaviviridae family viruses that include, but are not limited to, flaviviruses, pestiviruses and hepatitis C viruses. Such viruses also include yellow fever virus (YFV); Dengue virus, including Dengue types 1-4; Japanese Encephalitis virus; Murray Valley Encephalitis virus; St. Louis Encephalitis virus; West Nile virus; tick-borne encephalitis virus; Kunjin virus; Central European encephalitis virus; Russian spring-summer encephalitis virus; Powassan virus; Kyasanur Forest disease virus; and Omsk hemorrhagic fever virus.

Identification of inhibiting agents (e.g., anti-HCV agents) according to embodiments of the invention, and their use in inhibiting HCV replication and treating HCV infection, is of particular interest. The HCV to be inhibited may be of any genotype (genotype 1, 2, 3, 4, 5, 6, and the like), as well as subtypes of any HCV genotype (e.g., 1a, 1b, 2a, 2b, 3a, etc.). Because currently HCV genotype 1 is normally the most difficult to treat, application of the methods and the agents of embodiments of the invention to treat infections with HCV genotype 1 and genotype 1 subtypes is of particular interest.

While the specification below refers to HCV, such a reference is only for clarity and is not intended to limit the disclosure below to HCV. As noted above, the disclosure can be applied to any virus encoding a nucleotide-binding NS4B protein (e.g., a Flaviviridae virus having an NS4B polypeptide that binds the 3'-UTR of HCV negative strand RNA).

Screening Methods

Embodiments of present invention provide in vitro cell-free methods of identifying agents (inhibiting agents) that modulate RNA binding to an RNA-binding protein. The methods generally involve contacting, in a microfluidic device for example, a test agent with an RNA and an in vitro transcribed and translated protein that binds RNA; and detecting the effect, if any, of the test agent on binding of the RNA to the protein. Thus, embodiments of the invention provide in vitro cell-free methods of identifying agents that modulate an activity of a membrane-bound protein. Embodiments of the methods generally involve contacting, in a microfluidic device for example, a test agent with a membrane-bound protein; and determining the effect, if any, of the test agent on an activity of the membrane-bound protein.

In one embodiment, the invention provides in vitro cell-free methods of identifying agents that inhibit binding of NS4B to HCV RNA, in particular to the 3'-UTR of HCV. The methods generally involve contacting an HCV 3'-UTR-binding NS4B polypeptide with HCV 3'-UTR in the presence of a test agent; and detecting the effect, if any, of the test agent on binding of the NS4B polypeptide to the HCV 3'-UTR.

An NS4B polypeptide that is suitable for use in an embodiment of the screening method binds the 3'UTR of negative strand HCV RNA (SEQ ID NO: 2, FIG. 3). In an embodiment, a suitable NS4B polypeptide binds the 3'UTR of negative strand HCV RNA with a Kd of about 1 nM to 6 nM (e.g., about 1 nM to 1.5 nM, about 1.5 nM to 2 nM, about 2 nM to 2.5 nM, about 2.5 nM to 3 nM, about 3 nM to 3.5 nM, about 3.5 nM to 4 nM, about 4 nM to 4.5 nM, about 4.5 nM to 5 nM, or about 5 nM to 6 nM).

HCV 3'-UTR negative strand RNA-binding NS4B polypeptides that are suitable for use in embodiments of the screening method include NS4B polypeptides that comprise a domain that binds (in a nucleotide-independent manner) a stretch of at least 15, at least 20, at least 25, at least 30, at least 35, at least 40, at least 45, at least 50, at least 75, at least 100, at least 125, at least 150, at least 175, at least 200, at least 225, at least 250, at least 275, at least 300, at least 325, at least 350, at least 400, at least 450, at least 500, or at least 525 contiguous nucleotides of a nucleotide sequence having at least about 80%, at least about 85%, at least about 90%, at least about 95%, at least about 98%, at least about 99%, or 100%, identity over a stretch of from about 100 nucleotides to about 200 nucleotides, over a stretch of from about 200 nucleotides to about 300 nucleotides, over a stretch of from about 300 nucleotides to about 400 nucleotides, over a stretch of from about 400 nucleotides to about 500 nucleotides, or over the entire length of the nucleotide sequence set forth in FIG. 3 (SEQ ID NO: 2), which is the 3'UTR of the negative strand of an HCV genome.

For example, in some embodiments, a suitable NS4B binds a stretch of about 15 to 20, about 20 to 25, about 25 to 30, about 30 to 35, about 35 to 40, about 40 to 45, about 45 to 50, about 50 to 75, about 75 to 100, about 100 to 125, about 125 to 150, about 150 to 175, about 175 to 200, about 200 to 225, about 225 to 250, about 250 to 275, about 275 to 300, about 300 to 325, about 325 to 350, about 350 to 400, about 400 to 450, about 450 to 500, or about 500 to 525 contiguous nucleotides of a nucleotide sequence having at least about 80%, at least about 85%, at least about 90%, at least about 95%, at least about 98%, at least about 99%, or 100%, identity over a stretch of from about 100 nucleotides to about 200 nucleotides, over a stretch of from about 200 nucleotides to about 300 nucleotides, over a stretch of from about 300 nucleotides to about 400 nucleotides, over a stretch of from about 400 nucleotides to about 500 nucleotides, or over the entire length of the nucleotide sequence set forth in FIG. 3 (SEQ ID NO: 2).

Figure 7:
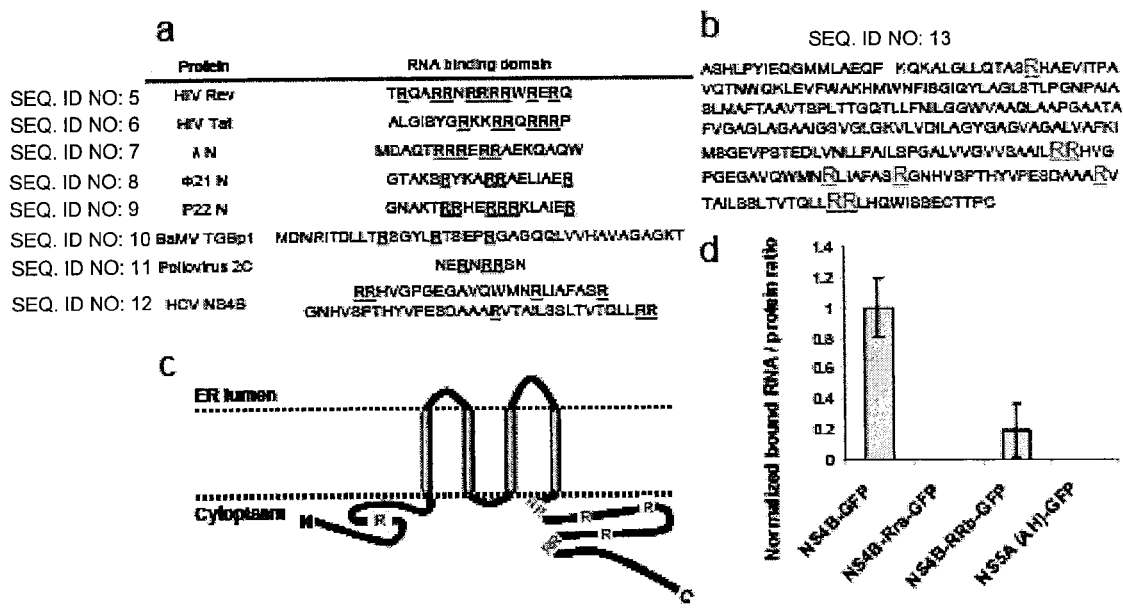
FIGS. 7a-7d illustrate the identification of RNA binding domains within NS4B and results relating to the same.

In an embodiment, a suitable NS4B polypeptide comprises an amino acid sequence having at least about 75%, at least about 80%, at least about 85%, at least about 90%, at least about 95%, at least about 98%, at least about 99%, or 100%, amino acid sequence identity over a stretch of from about 100 contiguous amino acids to 150 contiguous amino acids, over a stretch of from about 150 contiguous amino acids to about 200 contiguous amino acids, over a stretch of from about 200 contiguous amino acids to about 250 contiguous amino acids, or over the entire 261 contiguous amino acids, of the amino acid sequence depicted in FIG. 7B (SEQ ID NO: 13).

In some embodiments, a suitable NS4B polypeptide comprises one, two, three, four, five, six, seven, eight, nine, ten, or from ten to fifteen amino acid sequence substitutions, compared to the amino acid sequence depicted in FIG. 7B (SEQ ID NO: 13). In some embodiments, a suitable NS4B polypeptide comprises one or more amino acid substitutions in a nucleotide binding motif (e.g., GSVGGLGK, SEQ ID No. 16; amino acids 130-136 of the amino acid sequence depicted in FIG. 7B), such that the NS4B polypeptide does not bind GTP, but retains binding to negative strand 3'UTR RNA (SEQ ID No. 1).

In an embodiment, an NS4B polypeptide is a fusion protein, e.g., a polypeptide comprising an NS4B polypeptide and a heterologous (non-NS4B) polypeptide (e.g., a fusion partner), where suitable heterologous polypeptides (fusion partners) include, but are not limited to, an epitope tag (e.g., glutathione-S-transferase, hemagglutinin (HA; e.g., CYPY-DVPDYA (SEQ ID No. 17)), FLAG (e.g., DYKDDDDK, SEQ ID No. 18), c-myc (e.g., CEQKLISEEDL, SEQ ID No. 19), and the like); a polypeptide that provides a detectable signal (e.g., an enzyme that converts a substrate into a product that can be detected colorimetrically, fluorimetrically, and the like, where suitable enzymes include, but are not limited to, luciferase, alkaline phosphatase, peroxidase, and the like; a fluorescent protein (e.g., a green fluorescent protein, a red fluorescent protein, a yellow fluorescent protein, and the like); a luminescent protein; and the like); a polypeptide that provides for ease of purification of the polypeptide (e.g., a metal ion affinity peptide, e.g., (His)n, e.g., 6His, and the like); glutathione-S-transferase; and the like); a polypeptide that provides for insertion into a eukaryotic cell membrane; a polypeptide that provides for solubility; a polypeptide that provides for attachment to another moiety, to a solid support, and the like. In an embodiment, the NS4B polypeptide can also be detectably labeled, e.g., with a radiolabel. In an embodiment, the NS4B polypeptide is biotinylated.

In an embodiment, the NS4B polypeptide that is used in the assay is detectably labeled, e.g., is directly detectably labeled. Suitable detectable labels include, e.g., radiolabels; enzymes that act on a substrate to yield a colored, luminescent, or fluorescent product; fluorescent proteins (e.g., a green fluorescent protein, a yellow fluorescent protein, a red fluorescent protein, and the like); a fluorophore (e.g., fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705, and Oregon green); and the like. In an embodiment, the NS4B polypeptide is labeled during in vitro translation, e.g., using an in vitro transcription/translation system that includes a tRNA charged with a fluorescently labeled amino acid.

In an embodiment, the NS4B polypeptide is immobilized on a solid support. The NS4B polypeptide can be immobilized on a solid support directly or indirectly. In an embodiment, indirect immobilization can be achieved by immobilizing onto a solid support an antibody that specifically binds NS4B.

In an embodiment, the NS4B polypeptide can be produced in vitro, e.g., the NS4B polypeptide can be chemically synthesized; produced recombinantly by a cell in vitro; or can be produced using an in vitro transcription/translation system. In vitro transcription/translation systems are known in the art, and any known in vitro transcription/translation system, or a suitable modification thereof, can be used. For example, a rabbit reticulocyte in vitro transcription/translation system can be used. As another example, a T7 coupled wheat germ extract mixture (such as those sold by Promega) can be used. Methods for preparing polypeptides by in vitro transcription and translation are known in the art. See, e.g., "Methods in Molecular Biology: In vitro Transcription and Translation Protocols" (2007) Guido Grandi, ed., Humana Press.

In an embodiment, the NS4B polypeptide is purified, e.g., the NS4B polypeptide is at least about 80%, at least about 85%, at least about 90%, or at least about 95% pure. In other embodiments, the NS4B polypeptide is not purified, e.g., the NS4B polypeptide is less than 80%, less than 75%, less than 50% pure, or less than 25% pure. For example, where the NS4B polypeptide is prepared using an in vitro transcription/translation system, the NS4B polypeptide can be used directly from the in vitro transcription/translation system without further purification.

In an embodiment, the NS4B polypeptide is associated with a lipid bilayer, e.g., a microsomal membrane preparation. In an embodiment, the NS4B polypeptide is inserted in a lipid bilayer and exhibits native topology. In an embodiment, the NS4B polypeptide is inserted into a lipid bilayer immediately upon being translated, e.g., in an in vitro transcription/translation system.

In an embodiment, an NS4B polypeptide can be present in an assay method in an amount of about 1 attomole to 1 femtomole, about 1 femtomole to 1 picomole, about 1 picomole to 1 nanomole, about 1 nanomole to 50 nanomoles, about 50 nanomoles to 100 nanomoles, about 100 nanomoles to 500 nanomoles, about 500 nanomoles to 1 µmole, about 1 µmole to 50 µmoles, about 50 µmoles to 100 µmoles, about 100 µmoles to 500 µmoles, about 500 µmoles to 1 mmole, about 1 mmole to 50 mmole, about 50 mmole to 100 mmole, or greater than 100 mmole.

Embodiments of the present disclosure include inhibiting agents that inhibit binding of NS4B polypeptide to the 3'UTR of HCV negative strand RNA by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the binding of NS4B polypeptide to the 3'UTR of HCV negative strand RNA in the absence of the test agent.

In an embodiment, the inhibiting agent is one that inhibits binding of NS4B polypeptide to the 3'UTR of HCV negative strand RNA with a 50% inhibitory concentration (IC50) of about 100 µM to 50 µM, about 50 µM to 25 µM, about 25 µM to 10 µM, about 10 µM to 5 µM, about 5 µM to 1 µM, about 1 µM to 500 nM, about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, or less than about 5 nM.

In an embodiment, a test agent that inhibits binding of NS4B polypeptide to the 3'UTR of HCV negative strand RNA is further tested for its ability to inhibit HCV replication in a cell-based assay. In these embodiments, a test agent of interest is contacted with a mammalian cell that harbors all or part of an HCV genome; and the effect, if any, of the test agent on HCV replication is determined. Suitable cells include mammalian liver cells that are permissive for HCV replication, e.g., an immortalized human hepatocyte cell line that is permissive for HCV replication. For example, a suitable mammalian cell is Huh7 hepatocyte or a subclone of Huh7 hepatocyte, e.g., Huh-7.5. Suitable cell lines are described in, e.g., Blight et al. (2002) J. Virol. 76:13001; and Zhang et al. (2004) J. Virol. 78:1448. In an embodiment, the HCV genome in the cell comprises a reporter, e.g., a nucleotide sequence encoding luciferase, a fluorescent protein, or other protein that provides a detectable signal; and determining the effect, if any, of the test agent on HCV replication is achieved by detection of a signal from the reporter.

Thus, in an embodiment, a test agent of interest (e.g., a inhibiting agent) inhibits HCV replication by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the level of HCV replication in the absence of the test agent.

A variety of different test agents may be screened using embodiments of the present disclosure. Candidate agents encompass numerous chemical classes, e.g., small organic compounds having a molecular weight of more than 50 daltons and less than about 10,000 daltons, less than about 5,000 daltons, or less than about 2,500 daltons. Test agents can comprise functional groups necessary for structural interaction with proteins, e.g., hydrogen bonding, and can include at least an amine, carbonyl, hydroxyl or carboxyl group, or at least two of these functional chemical groups. The test agents can comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

In an embodiment, the inhibiting agent inhibits binding of NS4B to the 3'UTR of negative strand HCV RNA. In an embodiment, the inhibiting agent inhibits binding of NS4B to the 3'UTR of negative strand HCV RNA with an IC50 of less than about 500 nM, e.g., in some embodiments, the inhibiting agent inhibits binding of NS4B to the 3'UTR of negative strand HCV RNA with an IC50 of about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, or less than about 5 nM.

In an embodiment, the inhibiting agent, when contacted with an HCV-infected cell (e.g., an HCV-infected liver cell), inhibits HCV replication in the cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the level of HCV replication in the HCV-infected cell not contacted with the inhibiting agent.

In an embodiment, the inhibiting agent, when contacted with an HCV-infected cell (e.g., an HCV-infected liver cell), reduces the amount of infectious HCV viral particles produced by the HCV-infected cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the number of infectious HCV viral particles produced by the cell not contacted with the inhibiting agent.

In an embodiment, the inhibiting agent, when administered in one or more doses to an individual in need thereof, reduces the HCV viral load in the individual by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the HCV viral load in the individual not treated with the inhibiting agent.

Test agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds and chemical analogs thereof, or to new agents with unknown properties such as those created through rational drug design.

In an embodiment, test agents are synthetic compounds. A number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

In another embodiment, the test agents are provided as libraries of natural compounds in the form of bacterial, fungal, plant and animal extracts that are available or readily produced. Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In an embodiment, the test agents are organic moieties. In this embodiment, as is generally described in WO 94/24314, test agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepines, beta-lactams, tetracyclines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present methods.

In an embodiment, in addition to determining the effect of a test agent on inhibition of NS4B binding to 3'UTR of HCV negative strand RNA, a test agent is assessed for any cytotoxic activity it may exhibit toward a living eukaryotic cell, using well-known assays, such as trypan blue dye exclusion, an MTT (3-(4,5-dimethylthiazol-2-yl)-2,5-diphenyl-2H-tetrazolium bromide) assay, and the like. Agents that do not exhibit significant cytotoxic activity are considered candidate agents for further development.

In addition to an NS4B polypeptide, a 3'UTR of HCV negative strand RNA, and a test agent, a variety of other reagents may be included in the screening assay. These include reagents like salts, neutral proteins, e.g. albumin, detergents, etc., including agents that are used to facilitate optimal binding activity and/or reduce non-specific or background activity. Reagents that improve the efficiency of the assay, such as protease inhibitors, nuclease inhibitors, antimicrobial agents, etc. may be used. The components of the assay mixture are added in any order that provides for the requisite activity. Incubations are performed at any suitable temperature, typically between 4° C. and 40° C. Incubation periods are selected for optimum activity, but may also be optimized to facilitate rapid high-throughput screening. In some embodiments, about 0.1 hour and 1 hour, about 1 hour and 2 hours, or about 2 hours and 4 hours, is sufficient.

Assays of embodiments of the invention can include controls, where suitable controls include a sample (e.g., a sample comprising the NS4B polypeptide, and the 3'UTR of HCV negative strand RNA, in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

The effect, if any, of the test agent on binding of NS4B polypeptide to 3'UTR of HCV negative strand RNA can be determined using any of a variety of assays in accordance with the methods of embodiment of the invention.

In some embodiments, the screening assay is carried out in a microfluidic device. Microfluidic devices suitable for use in one or more methods of the invention are described in, e.g., U.S. Pat. Nos. 5,770,029; 5,755,942; 5,746,901; 5,681,751; 5,658,413; 5,653,939; 5,653,859; 5,645,702; 5,605,662; 5,571,410; 5,543,838; 5,480,614; 7,076,092, 7,067,263; and Maerkl and Quake (2007) Science 315:233, all of which are incorporated herein by reference.

In an embodiment, the screening protocol can be conducted according to the following protocol:

Screening for Compounds Inhibitory of NS4B's RNA Binding:

1) The library compounds (dissolved in DMSO) are spotted onto epoxy coated glass substrates slide (CEL Associates) by OmniGrid Micro (GeneMachines) microarrayer using a CMP3B pin (TeleChem International, Inc.) as a microarray with column and row pitches of 680 mm and 320 mm, respectively. For a primary screen spot compounds at a high concentration (~1 mM) in duplicates. For a secondary screen use a concentration that is 10 fold lower than in the primary screen and spot at least 5 replicates for each compound.

2) The array is allowed to dry.

3) Perform quality control of the array on a GenePix4000b (Molecular Devices).

4) The array is aligned to a microfluidic device by hand on a SMZ1500 (Nikon) stereoscope. A large device (2400 unit cells) is used for the primary screen and a smaller one (640 unit cells) for the secondary screen.

5) The array is bonded to the device overnight in the dark on a heated plate at 40° C.

6) The device is subjected to surface patterning (see below).

7) NS4B-GFP is expressed off chip using coupled transcription/translation rabbit reticulocyte system (Promega) in the presence of 2 µL canine microsomal membranes (Promega).

8) The protein and the Cy5-labeled HCV RNA probes (at a concentration of 1.5 nM) is loaded into the chip and allowed to incubate for 5-20 min in a 50 mM Hepes KOH (pH 6.8) buffer.

9) Each unit cell is isolated by activating the sandwich valves and incubate for 30 min to allow binding of the protein to surface biotinylated anti-GFP antibodies, solvation of library compounds, and equilibration of proteins and target RNA.

10) MITOMI is performed by closing the "button" membrane as well as the chamber valves for trapping surface-bound complexes while expelling any solution phase molecules.

11) It is washed briefly with Hepes KOH (pH 6.8) buffer to remove untrapped unbound material.

12) The device is scanned on a modified array WoRxe (AppliedPrecision) microarray scanner to detect protein synthesis and the trapped molecules.

13) Imaging and data analysis: Images were analyzed with GenePix3.0 (Molecular Devices). Each unit cell generates a single data point that is consisted of the ratio of median signal of Cy5 to median signal of GFP; thus, representing the ratio of surface bound RNA to surface bound expressed protein. Data from multiple data points should be averaged and their standard deviations calculated. Normalize the results to signal measured in unit cells containing no inhibitory compound. Define cutoff (for example: greater than 90% inhibition for inhibition in the primary screen, Inhibition greater than 2.5 fold for the secondary screen).

Surface Chemistry:

All devices were driven between 10 and 15 psi in the control line and between 4 and 6 psi for the flow line. For the initial surface derivatization steps, the chamber valves remained closed to prevent liquid from entering the chambers containing the spotted RNA targets.

First, all accessible surface area was derivatized by flowing a solution of biotinylated BSA (Pierce) resuspended to 2 mg/mL in dH$_2$O for 30 min through all channels, followed by a 10 min PBS wash. Next a 500 µg/mL Neutravidin (Pierce) solution in PBS was flown for 20 min, followed by a 10 min PBS wash. Next, the "button" membrane was closed and the PBS wash continued for an additional 5 min. Then all remaining accessible surface area except for the circular area of 60 µm masked by the button was passivated with the same biotinylated solution as above for 30 min, followed by a 10 min PBS wash. Finally a 1:1 solution of biotinylated-anti-GFP antibody (Abcam) in 2% BSA in PBS was loaded for 2-5 min, after which the "button" membrane was opened and flow continued for 20 min allowing specific functionalization of the previously masked circular area. This was again followed by a 10 min PBS wash completing the surface derivatization procedure.

Thus, in an embodiment, a screening method of an embodiment of the invention involves detecting the effect, if any, of a test agent on binding of an NS4B polypeptide to a 3'UTR of an HCV RNA, the method comprising: (a) flowing one or more test agents from one or more test agent sources through one or more microfluidic channels of an analytical device fabricated in a planar substrate, where the one more microfluidic channels have at least one cross-sectional dimension in a range from about 0.1 to 500 µm; (b) contacting the one or more test agents with at least a first sample comprising an NS4B polypeptide and a nucleic acid comprising a 3'UTR of an HCV RNA; and c) detecting the effect, if any, of the test agent on binding of the NS4B polypeptide to the 3'UTR of an HCV RNA in a detection zone of the device. In some embodiments, the method further comprises one or more wash steps after contacting step (b). In an embodiment, the detecting step comprises detecting the ratio of a first detectable label associated with the NS4B polypeptide to the ratio of a second detectable label associated with the nucleic acid comprising the 3'UTR. In an embodiment, the method can use a microfluidics analytic device.

Inhibiting Agents

Embodiments of the present invention provide inhibiting agents that can be used to treat a host infected by a Flaviviridae family virus. In particular, the inhibiting agent can be used to treat hosts infected with Hepatitis C virus. The inhibiting agent can be, for example and without limitation, in one or more of the following groups: clemizole, clemizole analogs, and compounds having a clemizole scaffold; H1 antagonists, H1 receptor antagonists that share structural similarity with clemizole; cinoxacin, cinoxacin analogs, and compounds having a cinoxacin scaffold; norepinephrine, norepinephrine analogs, and compounds having a norepinephrine scaffold; glybenclamide, glybenclamide analogs, and compounds having a glybenclamide scaffold; spiradoline, spiradoline analogs, and compounds having a spiradoline scaffold; tropicamide, tropicamide analogs, and compounds having a tropicamide scaffold; any of the inhibiting agents in the various compounds described below; pharmaceutical salts of each of these compounds; isosteres of any of the foregoing; and the like. In an embodiment, the inhibiting agent is clemizole, clemizole analogs, and compounds having a clemizole scaffold. In an embodiment, the inhibiting agent is clemizole analogs and compounds having a clemizole scaffold.

Embodiments of the invention include inhibiting agents contained in compositions, pharmaceutical compositions, liquid compositions, gel compositions, and the like, including without limitation controlled release and sustained release formulations. In an embodiment, the inhibiting agent is used in combination with another agent (e.g., other inhibiting agents of the present disclosure or other agents) to treat a Flaviviridae family viral infection, and in various embodiments, each of the agents or one of the agents is in a controlled release or sustained release formulation. In some instances the term "inhibiting agent" may be referred to as an agent, a compound, an active agent or a drug.

As mentioned above, illustrative inhibiting agents useful in the methods of the invention can be in one or more of the following groups: clemizole, clemizole analogs, and compounds having a clemizole scaffold; H1 antagonists, H1 receptor antagonists that share structural similarity with clemizole; cinoxacin, cinoxacin analogs, and compounds having a cinoxacin scaffold; norepinephrine, norepinephrine analogs, and compounds having a norepinephrine scaffold; glybenclamide, glybenclamide analogs, and compounds having a glybenclamide scaffold; spiradoline, spiradoline analogs, and compounds having a spiradoline scaffold; tropicamide, tropicamide analogs, and compounds having a tropicamide scaffold; compounds noted below as having inhibitory activity and their analogs; isosteres of any of the foregoing; and the like.

In the descriptions of the compounds below, terms defined above have their defined meanings, and the definitions referred to below describe preferred embodiments of the inhibiting agents described. Reference to "the aryl group" and/or "the alkyl groups" of the preferred embodiments described in this section refers to the preferred embodiments definitions of aryl and alkyl.

The term "alkyl" refers to a group such as a methyl group, an ethyl group, an isopropyl group, an isobutyl group, and a trifluoromethyl group. In addition for these embodiments the term alkyl includes a group having one of the following structures:

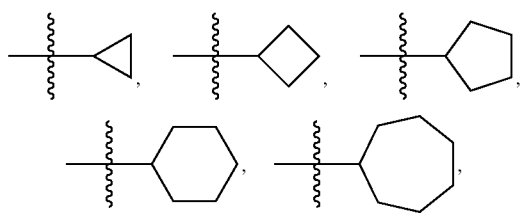

The term "aryl" refers to a group selected from the following groups A-F.

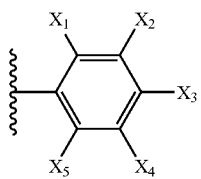

Group A

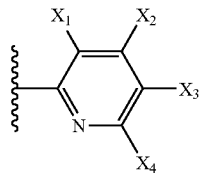

Group B

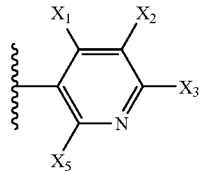

Group C where $X_1$-$X_5$ are each, when present in compounds of Groups A, B, and C, independently selected from the group consisting of:

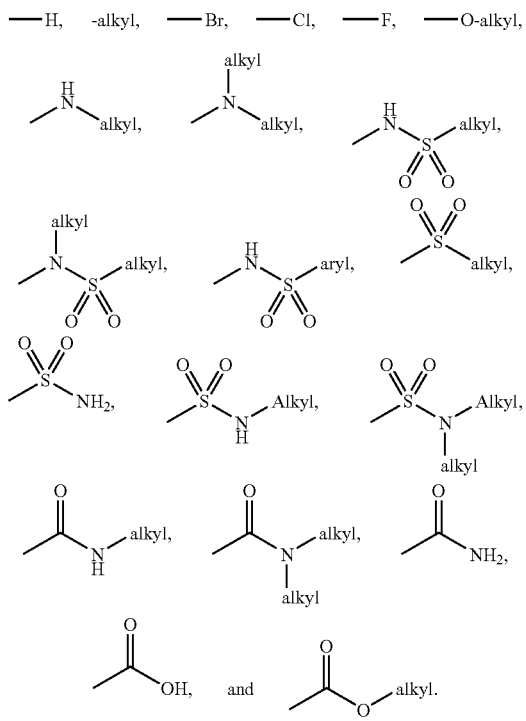

In an embodiment, at least one position of Group C ($X_1$-$X_3$ and $X_5$) is substituted (non-hydrogen).

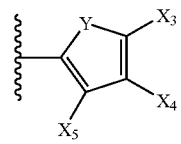

Group D

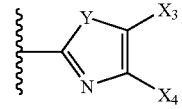

Group E

-continued

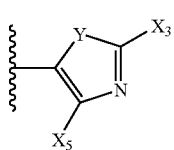
Group F where in compounds of Group D, E, and F, Y is selected from the group consisting of: —O, —S, —NH, —N-alkyl, and —N-acyl; $X_3$ is selected from the group consisting of: —H, —CH$_3$, —Cl, —F, CF$_3$ and —OCH$_3$; and $X_4$ and $X_5$ are, when present, independently selected from the group consisting of: H and CH$_3$.

As noted above, the inhibiting agent includes, but is not limited to, clemizole, a clemizole analog, and a compound having a clemizole scaffold; and isosteres of any of the compounds of any of the foregoing groups.

Accordingly, embodiments of the present invention include clemizole and inhibiting agents that have a clemizole scaffold. The structures of clemizole and compounds having a clemizole scaffold are shown below (clemizole scaffold is shown at left and clemizole at right).

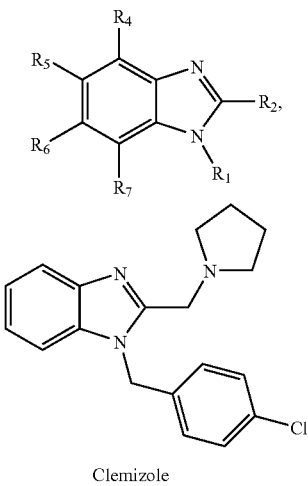

Clemizole

In an embodiment of the clemizole scaffold, $R_1$ is selected from the group consisting of: —H,

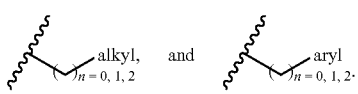

In one embodiment $R_1$ is

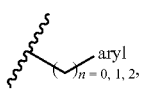

and the aryl group (Groups A-F shown above) is substituted at $X_3$. In an embodiment, the aryl and the alkyl groups can be selected from the preferred embodiments described in this section.

In an embodiment of the clemizole scaffold, $R_2$ is selected from the group consisting of: —H and

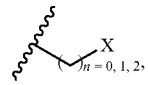

where X is selected from the group consisting of:

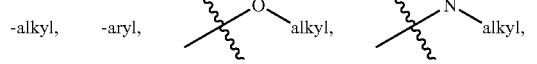

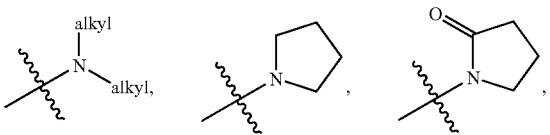

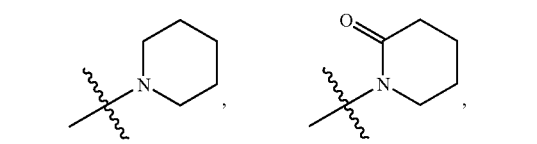

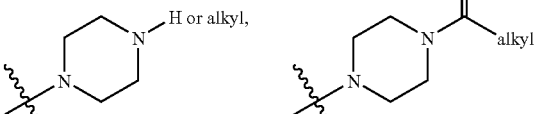

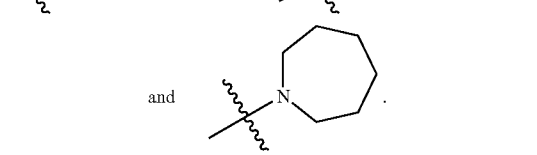

In an embodiment, the aryl and the alkyl groups can be selected from the preferred embodiments described in this section.

In an embodiment of the clemizole scaffold, each of $R_4$-$R_7$ is independently selected from the group consisting of:

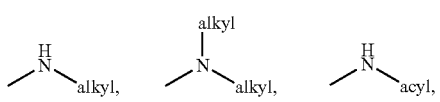

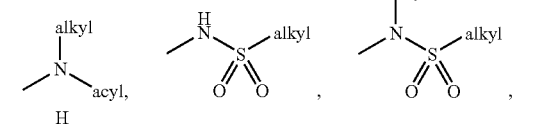

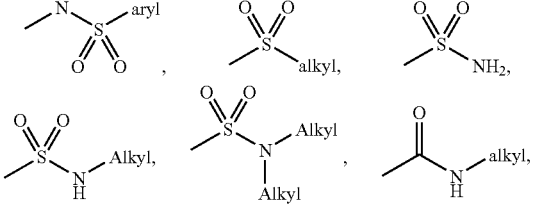

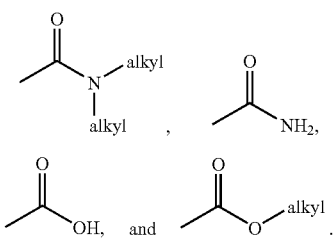

In an embodiment, the alkyl groups can be selected from the preferred embodiments described in this section. In one embodiment, only two of these positions (two of $R_4$-$R_7$) are substituted, and the substituted moiety is, for each substituted position, independently selected from the group consisting of: —Cl, —F, —CH$_3$, and —OCH$_3$, while the other positions are unsubstituted (having an —H at such position). In another embodiment, $R_5$ and $R_6$ are substituted, and the substituted moiety is, for each substituted position, independently selected from the group consisting of: —Cl, —F, —CH$_3$, and —OCH$_3$, while $R_4$ and $R_7$ are unsubstituted.

In an embodiment of the clemizole scaffold, one or more sets of adjacent groups ($R_4$ and $R_5$, $R_5$ and $R_6$, or $R_6$ and $R_7$) are connected by a ring containing between 5 and 7 atoms. In an embodiment, the ring is composed of a structure selected from the group consisting of:

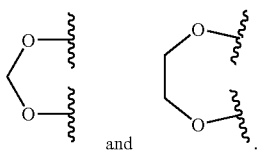 [SMILES: *OCO* ; *OCCO* ; "and" ; "."]

In an embodiment, $R_5$ and $R_6$ are connected by one of the rings having a structure selected from the group consisting of:

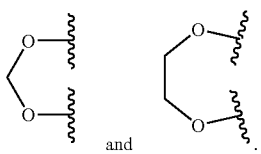 [SMILES: *OCO* ; *OCCO* ; "and" ; "."]

In an embodiment of the clemizole scaffold, $R_1$ is selected from the group consisting of

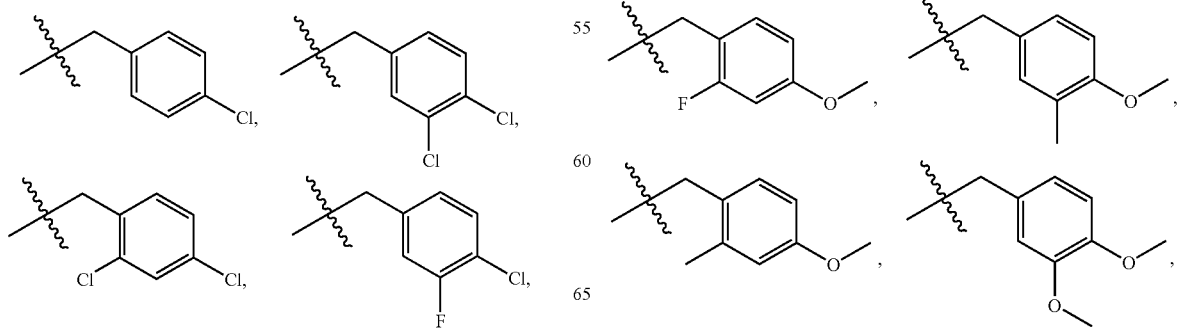

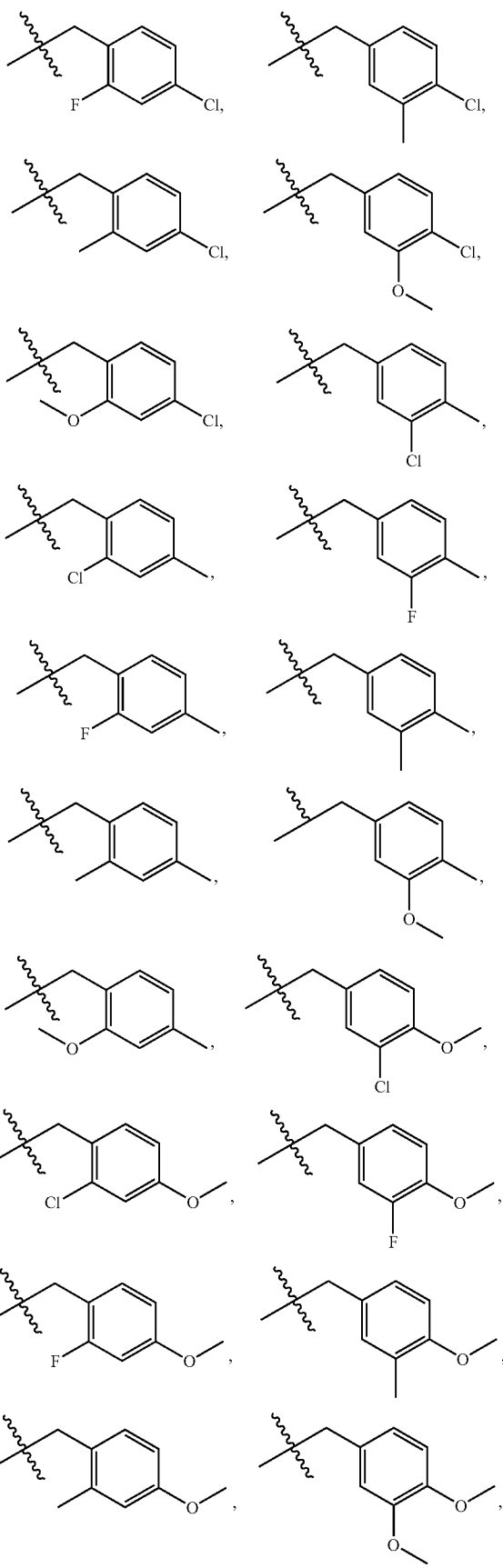

-continued

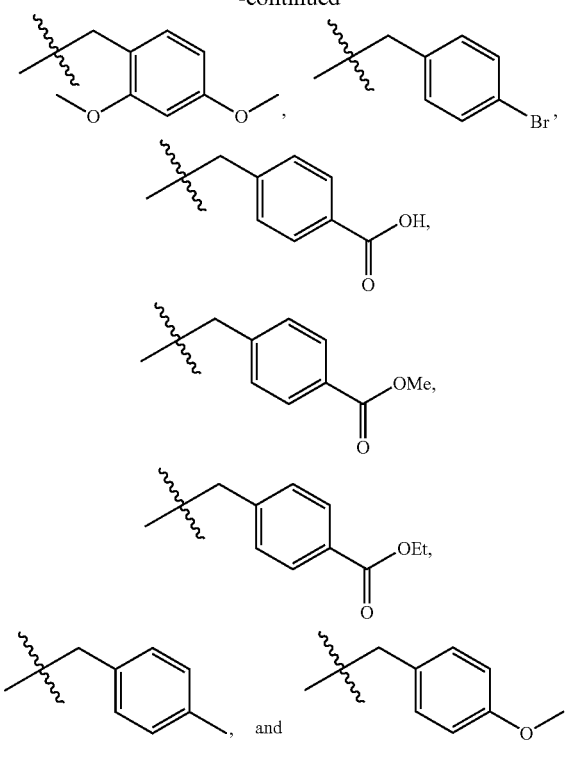

$R_2$ is selected from the group consisting of:

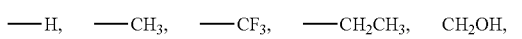

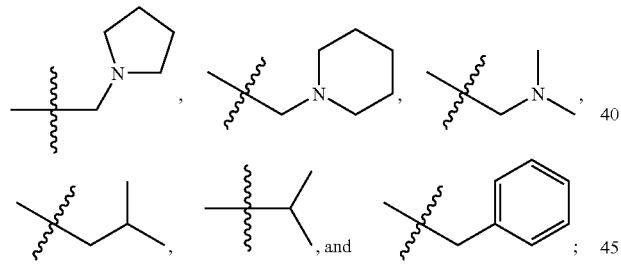

$R_4$ is selected from the group consisting of: —H and —$NH_2$; $R_5$ and $R_6$ are independently selected from the group consisting of:

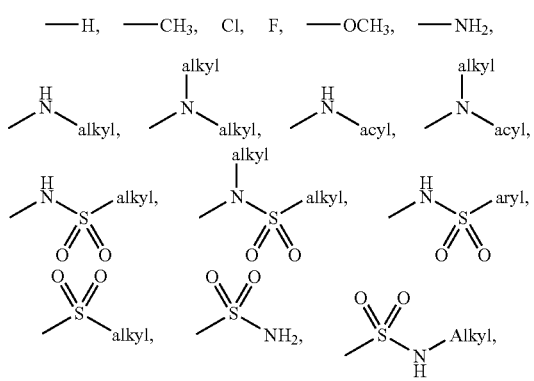

-continued

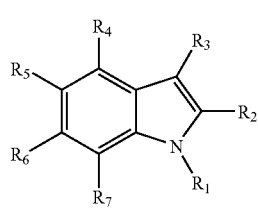

and $R_7$ is —H. In an embodiment, the alkyl groups can be selected from the preferred embodiments described in this section.

Additional embodiments of inhibiting agents of the invention include isosteres of clemizole and compounds having a clemizole scaffold. Isosteres of the benzoimidazole core structure of clemizole include the compounds defined by the structures below (the benzoimidazole core structure is shown for reference; in each of the structures $R_1$-$R_2$ and $R_4$-$R_7$ are as defined above and $R_3$ can be a group such as that described by $R_4$-$R_7$).

The following structure is a benzoimidazole core structure.

The following compound is an indazole core structure, an isostere of the benzoimidazole core structure.

The following compound is an indole core structure, an isostere of the benzoimidazole core structure.

The following compound is a benzoisoxazole core structure, an isostere of the benzoimidazole core structure.

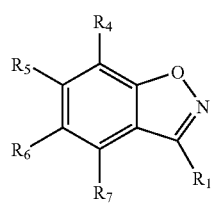

The following compounds are imidazopyridine core structures, isosteres of the benzoimidazole core structure.

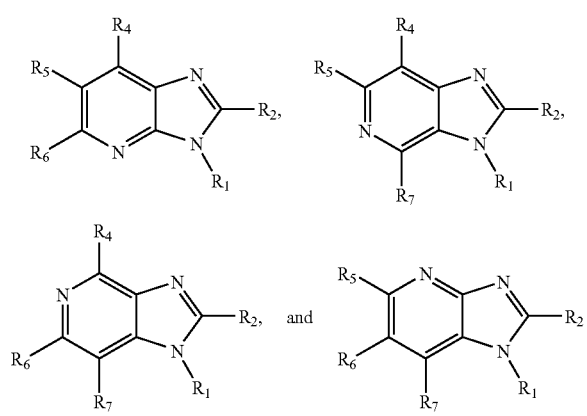

The following compounds are pyrazolopyridine core structures, isosteres of the benzoimidazole core structure.

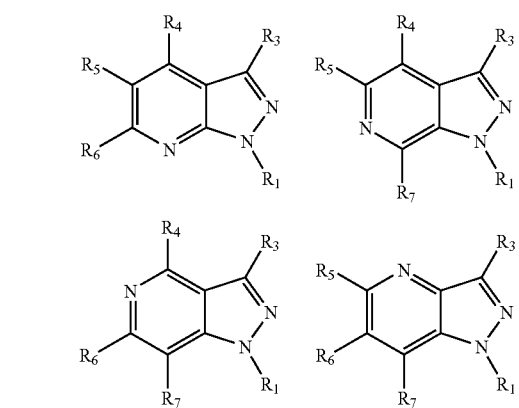

The following compounds are pyrrolopyridine (Azaindole) core structures, isosteres of the benzoimidazole core structure.

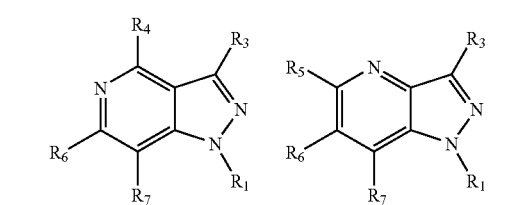

-continued

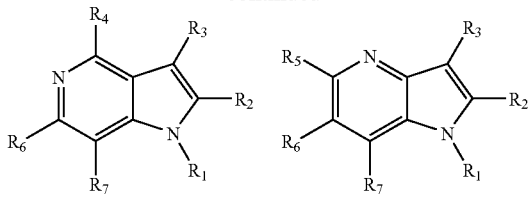

The following compounds are isoxazolopyridine core structures, isosteres of the benzoimidazole core structure.

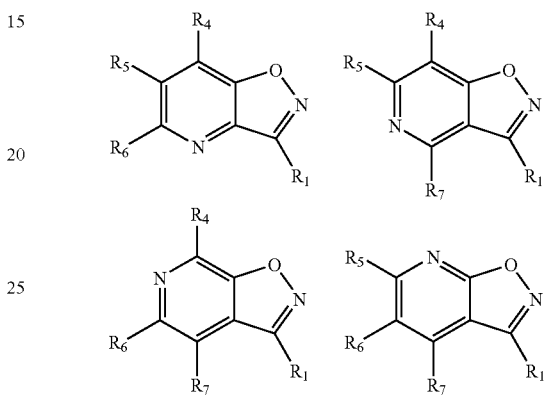

The following compound is an imidazopyrazine core structure, an isostere of the benzoimidazole core structure.

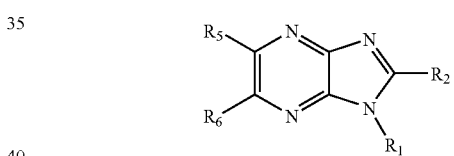

The following compound is a pyrazolopyrazine core structure, an isostere of the benzoimidazole core structure.

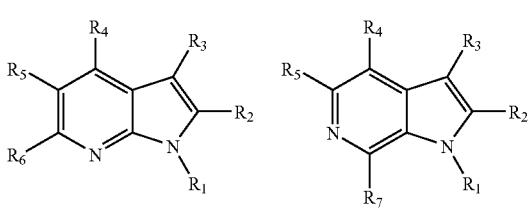

The following compound is a pyrrolopyrazine core structure, an isostere of the benzoimidazole core structure.

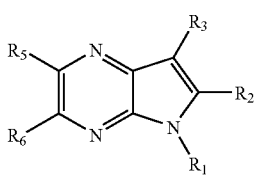

The following compound is an isoxazolopyrazine core structure, an isostere of the benzoimidazole core structure.

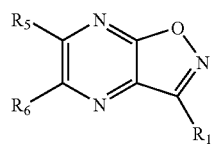

The following compound is an imidazopyrazine core structure, an isostere of the benzoimidazole core structure.

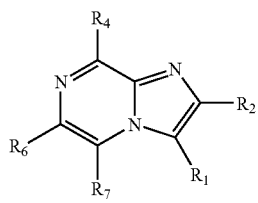

The following compounds are pyrazolopyrimidine core structures, isosteres of the benzoimidazole core structure.

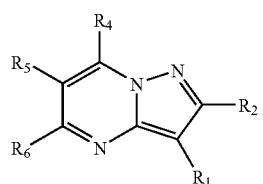

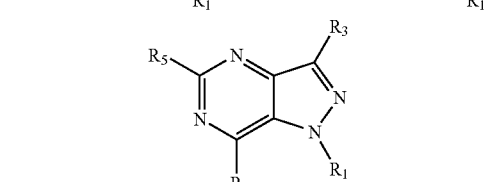

The following compounds are pyrrolopyrimidine core structures, isosteres of the benzoimidazole core structure.

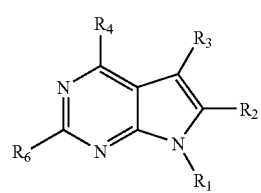

The following compounds are isoxazolopyrimidine core structures, isosteres of the benzoimidazole core structure.

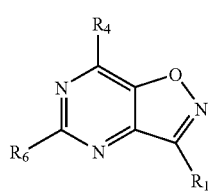

The following compounds are purine core structures, isosteres of the benzoimidazole core structure.

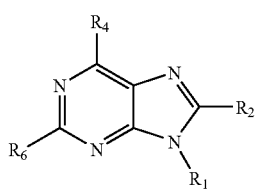

In an embodiment, the inhibiting agent is a compound having one of the following structures:

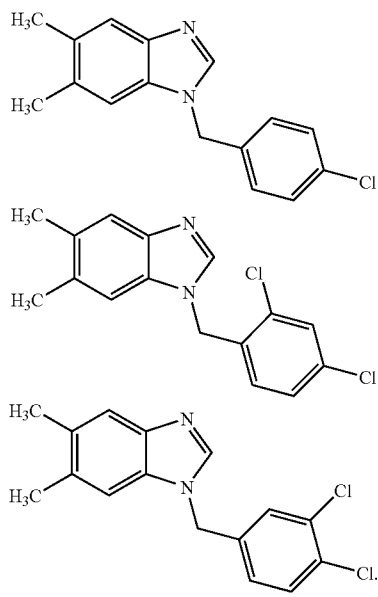

In an embodiment, the inhibiting agent is a compound having one of the following structures:

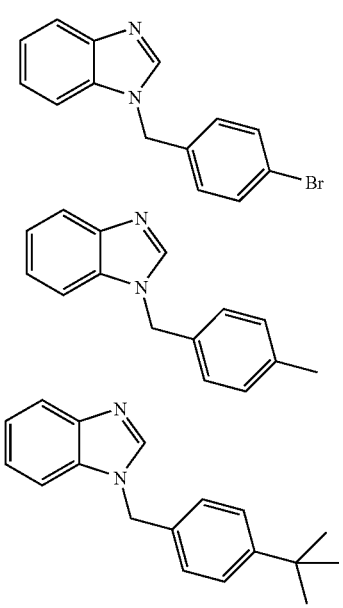

In an embodiment, the inhibiting agent includes 5,6-disubstituted clemizole compounds. In an embodiment, the inhibiting agent includes novel 5,6-disubstituted clemizole compounds, where the substitution does not include diethoxy substitutions. In an embodiment, the inhibiting agent can include 5,6-disubstituted clemizole compounds following structure:

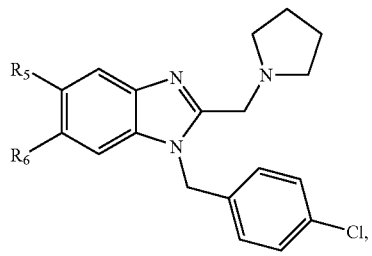

where $R_5$ and $R_6$ include the groups noted above for $R_5$ and $R_6$. In another embodiment, $R_5$ is selected from the group consisting of:

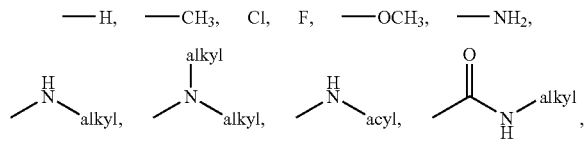

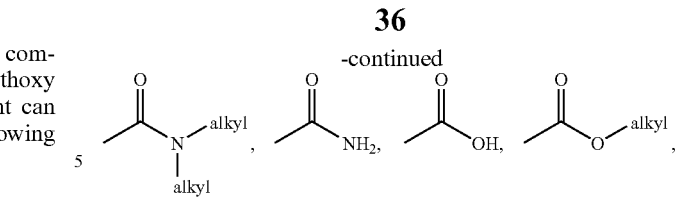

and —$SO_2CH_3$; $R_6$ is selected from the group consisting of

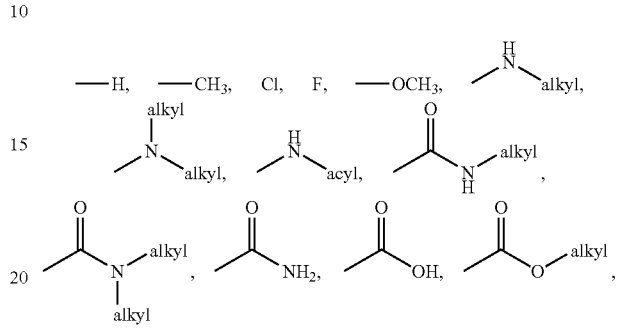

and —$NH_2$. In an embodiment, the alkyl groups can be selected from the preferred embodiments described in this section.

Table 1 shows structures of additional inhibiting agents of the invention and illustrative starting materials to prepare them.

TABLE 1

| | Structure | Illustrative Starting Materials |
|---|---|---|
| 1 | 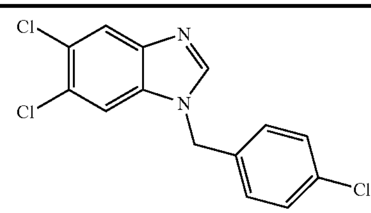 | |
| 2 | 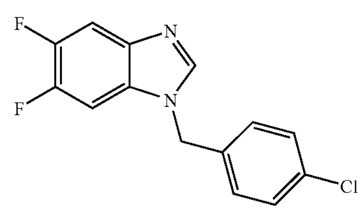 [SMILES: Fc1cc2ncn(Cc3ccc(Cl)cc3)c2cc1F] | |
| 3 | 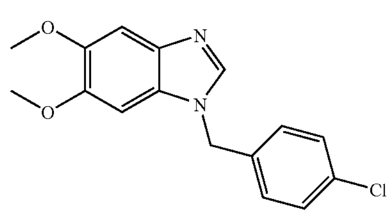 [SMILES: COc1cc2ncn(Cc3ccc(Cl)cc3)c2cc1OC] | |
| 4 | 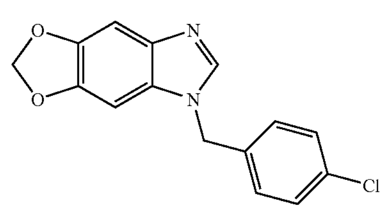 [SMILES: Clc1ccc(Cn2cnc3cc4c(cc32)OCO4)cc1] | |

TABLE 1-continued

| | Structure | Illustrative Starting Materials |
|---|---|---|
| 5 | 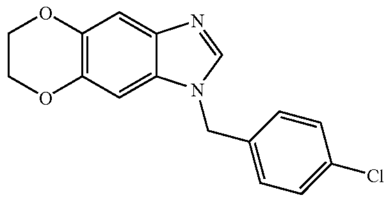 [SMILES: Clc1ccc(Cn2cnc3cc4c(cc32)OCCO4)cc1] | |
| 6 | 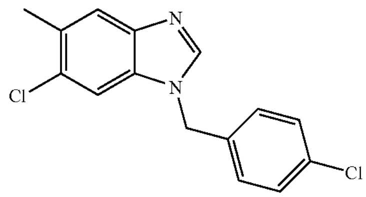 [SMILES: Cc1cc2ncn(Cc3ccc(Cl)cc3)c2cc1Cl] | |
| 7 | 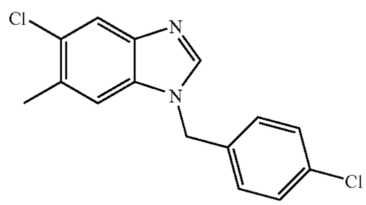 [SMILES: Cc1cc2c(cc1Cl)ncn2Cc1ccc(Cl)cc1] | |
| 8 | 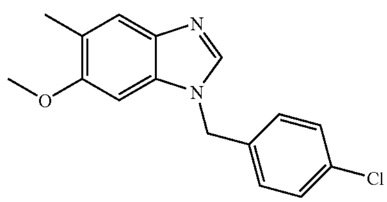 [SMILES: COc1cc2c(cc1C)ncn2Cc1ccc(Cl)cc1] | |
| 9 | 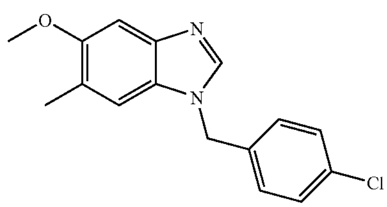 [SMILES: COc1cc2ncn(Cc3ccc(Cl)cc3)c2cc1C] | |
| 10 | 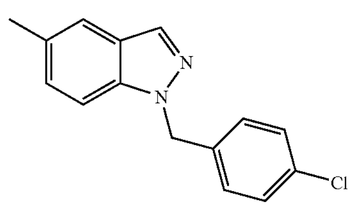 [SMILES: Cc1ccc2c(cnn2Cc2ccc(Cl)cc2)c1] | |
| 11 | 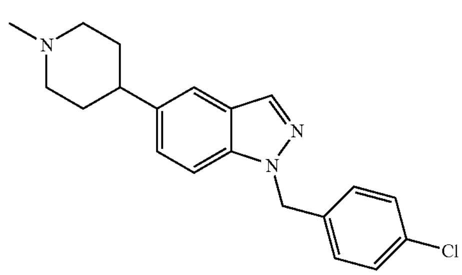 [SMILES: CN1CCC(c2ccc3c(cnn3Cc3ccc(Cl)cc3)c2)CC1] | |

TABLE 1-continued

| | Structure | Illustrative Starting Materials |
|---|---|---|
| 12 | 5-(trifluoromethyl)-1-(4-chlorobenzyl)-1H-indazole | 5-(trifluoromethyl)-1H-indazole |
| 13 | 5-cyano-6-fluoro-1-(4-chlorobenzyl)-1H-indazole | 5-cyano-6-fluoro-1H-indazole |
| 14 | 5-chloro-1-(4-chlorobenzyl)-1H-indazole | 5-chloro-1H-indazole |
| 15 | 5,6-dichloro-1-(4-chlorobenzyl)-1H-indazole | 5,6-dichloro-1H-indazole |
| 16 | 5,6-dimethyl-1-(4-chlorobenzyl)-1H-indazole | 5,6-dimethyl-1H-indazole |
| 17 | 6-methyl-1-(4-chlorobenzyl)-1H-indazole | 6-methyl-1H-indazole |
| 18 | 5-chloro-6-methyl-1-(4-chlorobenzyl)-1H-indazole | 5-chloro-6-methyl-1H-indazole |

TABLE 1-continued

| | Structure | Illustrative Starting Materials |
|---|---|---|
| 19 | 5-methoxy-6-methyl-1-(4-chlorobenzyl)-1H-indazole | 5-methoxy-6-methyl-1H-indazole |
| 20 | 5,6-dimethyl-1-(4-chlorobenzyl)-1H-indole | 5,6-dimethyl-1H-indole |
| 21 | 5,6-dimethyl-3-(4-chlorobenzyl)-3H-imidazo[4,5-b]pyridine | 5,6-dimethyl-3H-imidazo[4,5-b]pyridine |
| 22 | 3-(4-chlorobenzyl)-3H-imidazo[4,5-c]pyridine | 3H-imidazo[4,5-c]pyridine |

Table 2 shows structures of additional inhibiting agents of the invention based on the structure below:

TABLE 2

| $R_1$ | $R_2$ | $R_4$ | $R_5$ | $R_6$ | $R_7$ |
|---|---|---|---|---|---|
| 3,4-dichlorobenzyl | piperidin-1-ylmethyl | H | H | H | H |
| 3-fluoro-4-chlorobenzyl | piperidin-1-ylmethyl | H | H | H | H |

TABLE 2-continued
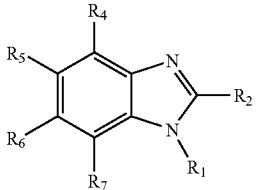
| R₁ | R₂ | R₄ | R₅ | R₆ | R₇ |
|---|---|---|---|---|---|
| 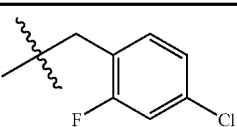 | 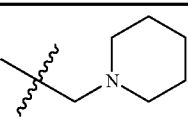 | H | H | H | H |
| 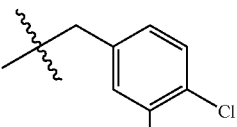 | 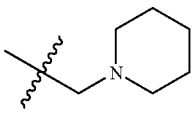 | H | H | H | H |
| 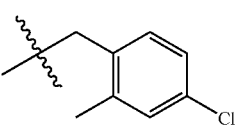 | 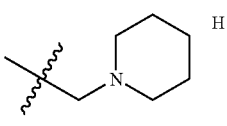 | H | H | H | H |
| 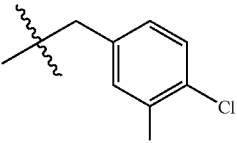 | 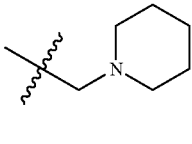 [SMILES: *CN1CCCCC1] | H | H | H | H |
| 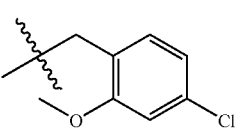 [SMILES: *Cc1ccc(Cl)cc1OC] | 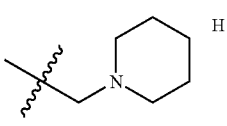 | H | H | H | H |
| 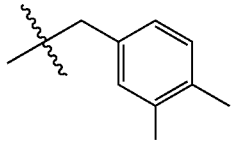 | 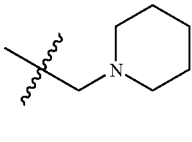 [SMILES: *CN1CCCCC1] | H | H | H | H |
| 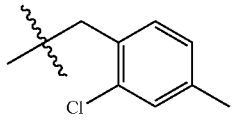 [SMILES: *Cc1ccc(C)cc1Cl] | 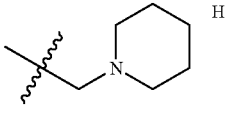 | H | H | H | H |
| 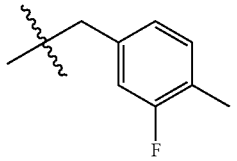 [SMILES: *Cc1ccc(C)c(F)c1] | 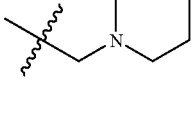 | H | H | H | H |
| 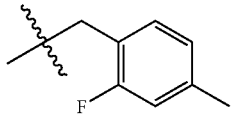 [SMILES: *Cc1ccc(C)cc1F] | 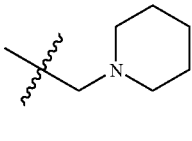 [SMILES: *CN1CCCCC1] | H | H | H | H |

TABLE 2-continued
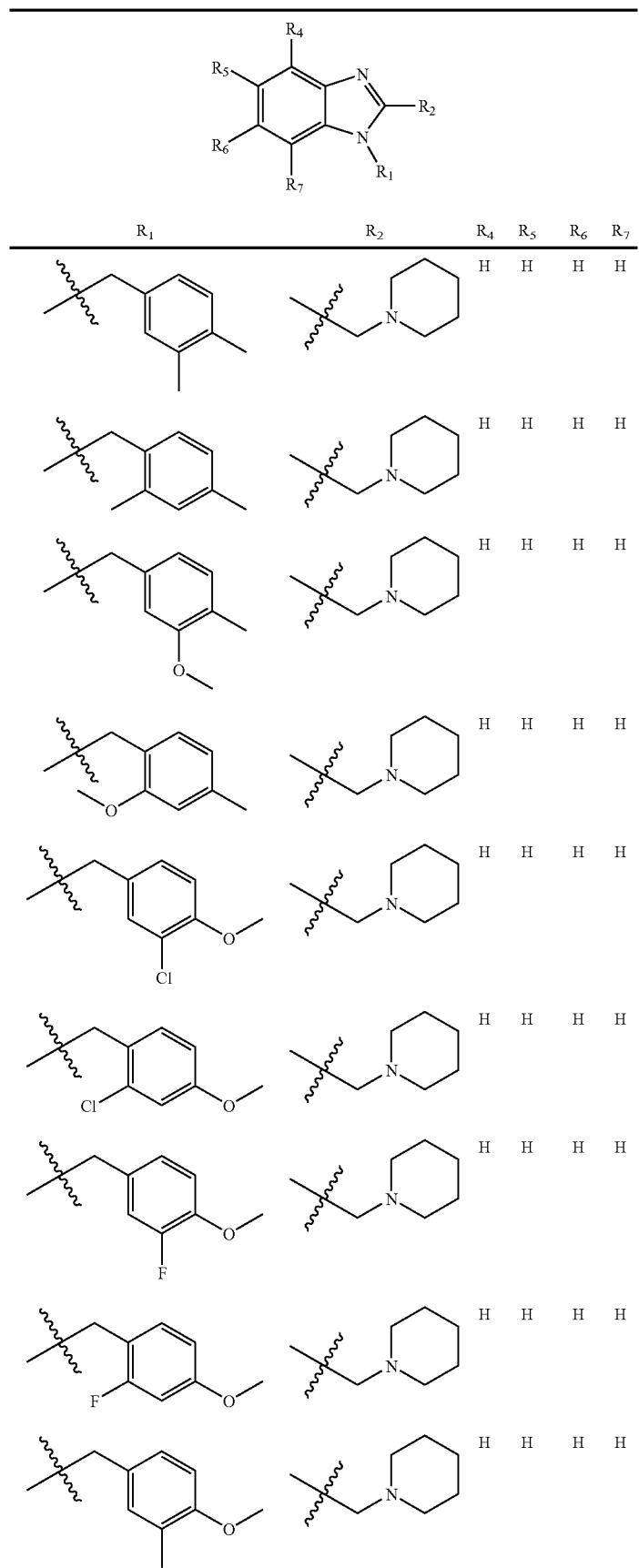

TABLE 2-continued
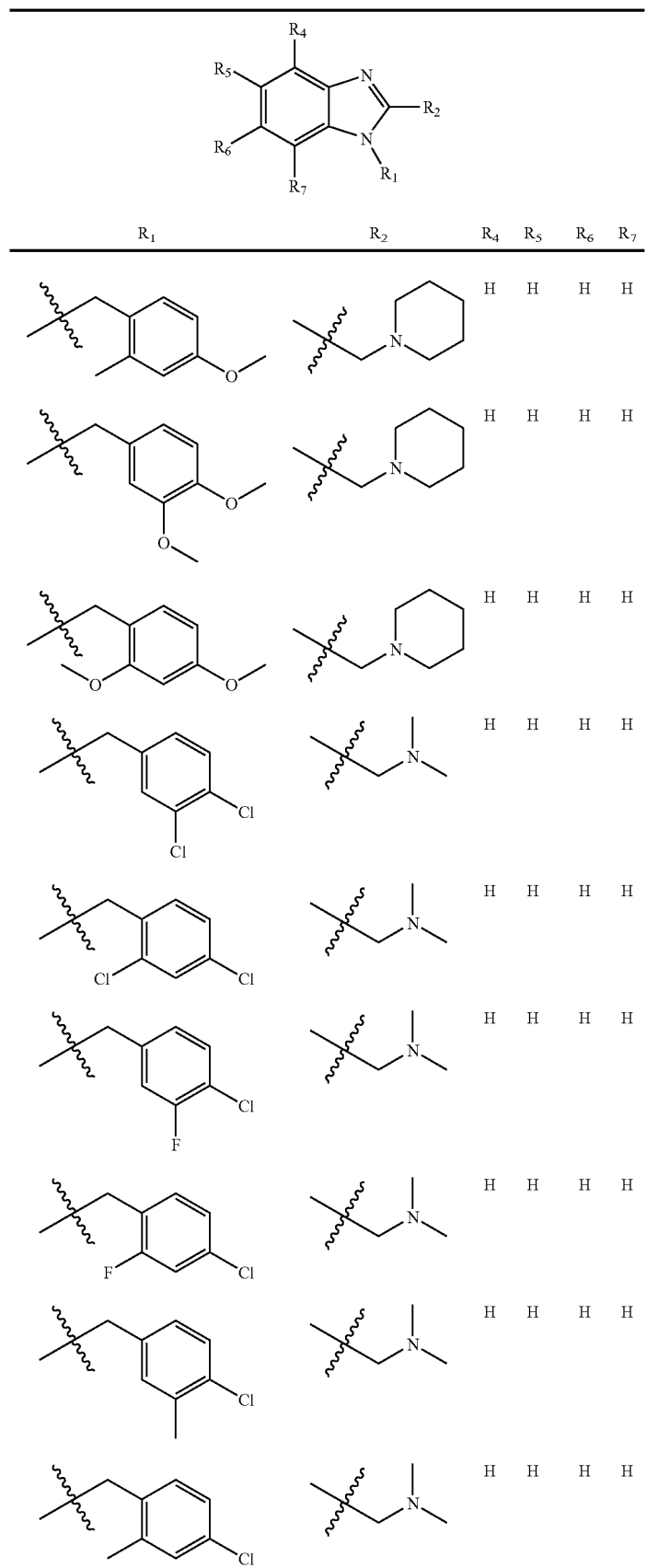

TABLE 2-continued
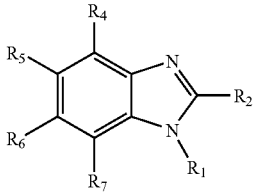

TABLE 2-continued
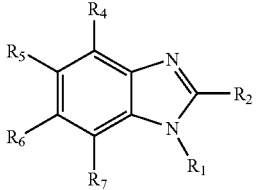
| R₁ | R₂ | R₄ | R₅ | R₆ | R₇ |
|---|---|---|---|---|---|
| 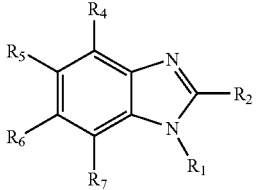 | 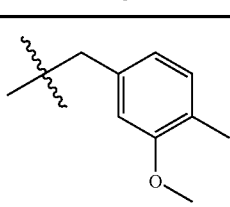 | H | H | H | H |
| 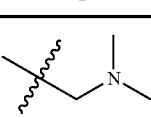 | 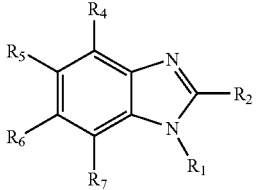 | H | H | H | H |
| 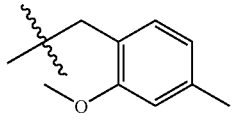 [SMILES: *Cc1ccc(C)cc1OC] | 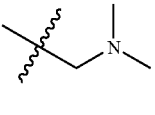 [SMILES: *CN(C)C] | H | H | H | H |
| 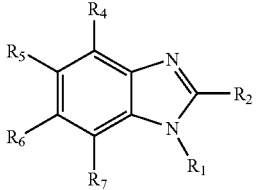 | 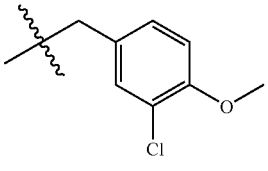 [SMILES: *Cc1ccc(OC)c(Cl)c1] | H | H | H | H |
| 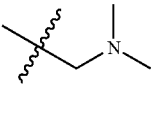 [SMILES: *CN(C)C] | 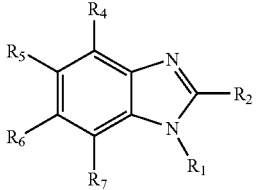 | H | H | H | H |
| 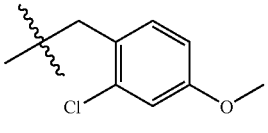 [SMILES: *Cc1ccc(OC)cc1Cl] | 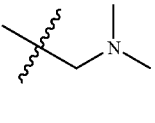 | H | H | H | H |
| 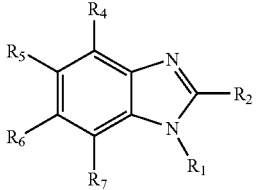 | 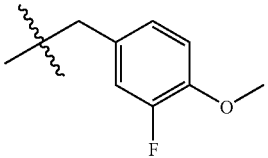 | H | H | H | H |
| 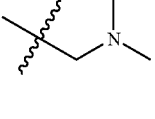 | 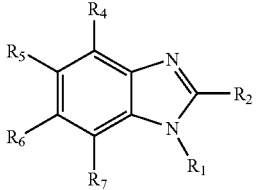 | H | H | H | H |

TABLE 2-continued
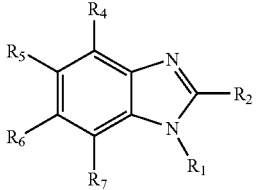
| R₁ | R₂ | R₄ | R₅ | R₆ | R₇ |
|---|---|---|---|---|---|
| 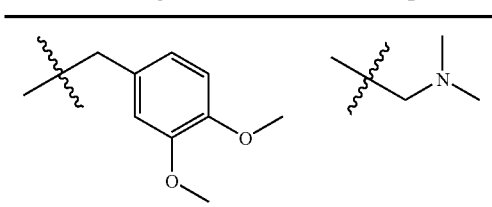 | 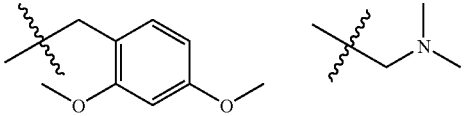 | H | H | H | H |
| 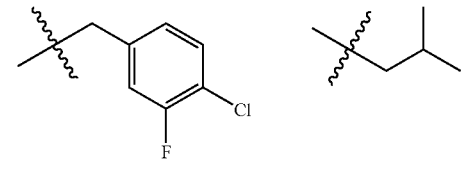 | 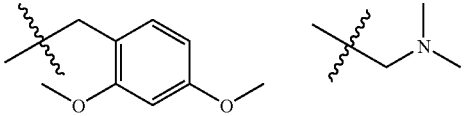 | H | H | H | H |
| 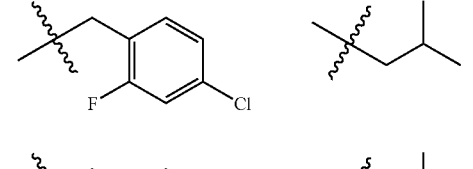 | 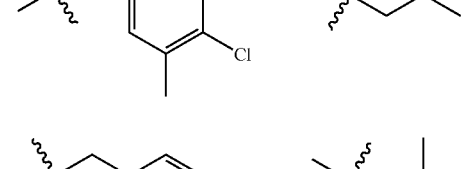 | H | H | H | H |
| 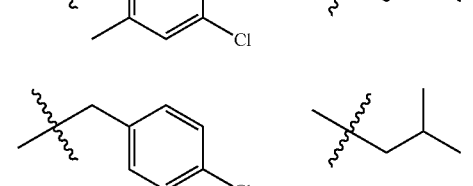 | 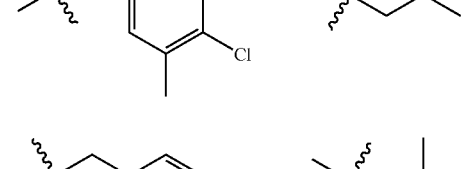 | H | H | H | H |
| 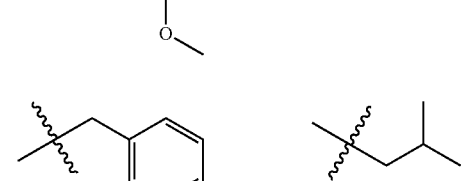 | 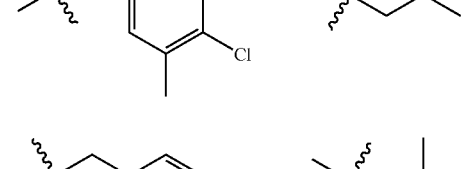 | H | H | H | H |
|  | 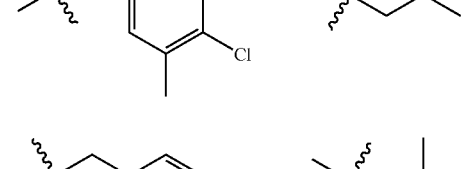 | H | H | H | H |
|  | 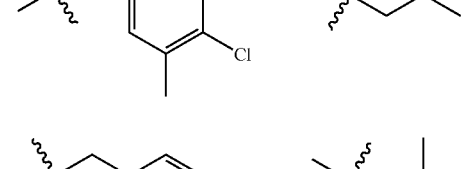 | H | H | H | H |
|  | 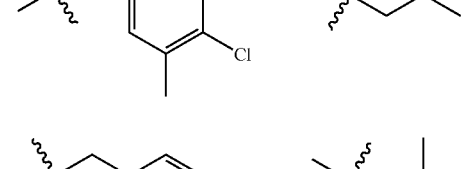 | H | H | H | H |

TABLE 2-continued
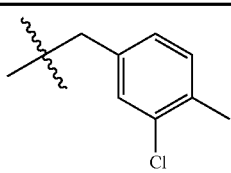
| R₁ | R₂ | R₄ | R₅ | R₆ | R₇ |
|---|---|---|---|---|---|
| 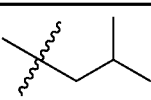 | 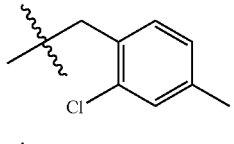 | H | H | H | H |
| 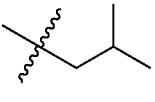 [SMILES: *CC(C)C] | 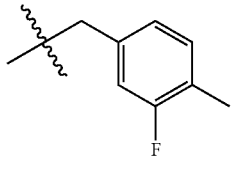 | H | H | H | H |
| 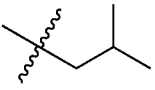 [SMILES: *CC(C)C] | 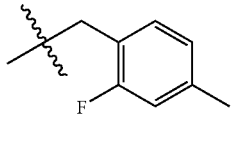 | H | H | H | H |
| 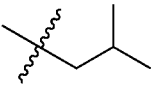 | 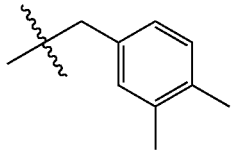 | H | H | H | H |
| 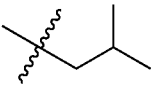 [SMILES: *CC(C)C] | 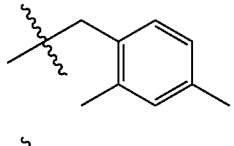 | H | H | H | H |
| 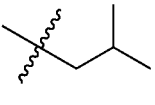 [SMILES: *CC(C)C] | 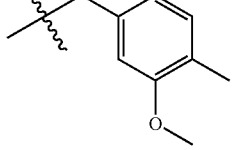 | H | H | H | H |
| 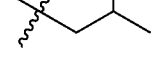 | | H | H | H | H |
| 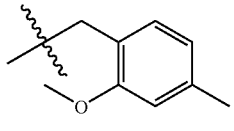 | | H | H | H | H |
| 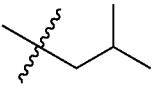 [SMILES: *CC(C)C] | | H | H | H | H |

TABLE 2-continued
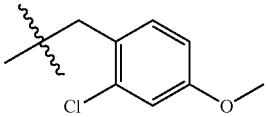 [SMILES: *Cc1ccc(OC)cc1Cl]
| R1 | R2 | R4 | R5 | R6 | R7 |
|---|---|---|---|---|---|
| 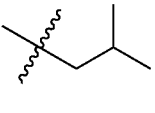 [SMILES: *CC(C)C] | 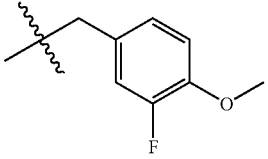 [SMILES: *Cc1ccc(OC)c(F)c1] | H | H | H | H |
| 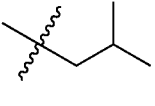 | 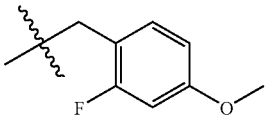 | H | H | H | H |
| 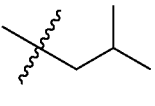 | 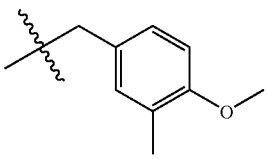 [SMILES: *Cc1ccc(OC)c(C)c1] | H | H | H | H |
| 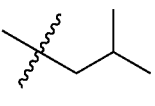 [SMILES: *CC(C)C] | 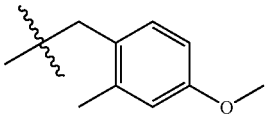 [SMILES: *Cc1ccc(OC)cc1C] | H | H | H | H |
| 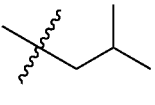 [SMILES: *CC(C)C] | 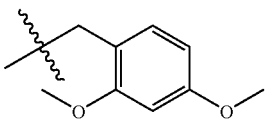 [SMILES: *Cc1ccc(OC)cc1OC] | H | H | H | H |
| 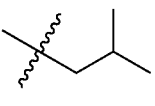 [SMILES: *CC(C)C] | 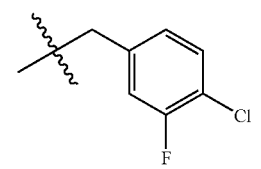 [SMILES: *Cc1ccc(Cl)c(F)c1] | H | H | H | H |
| 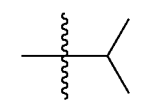 | 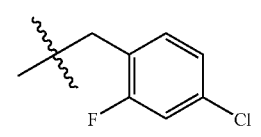 [SMILES: *Cc1ccc(Cl)cc1F] | H | H | H | H |
| 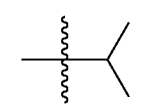 [SMILES: *C(C)C] | 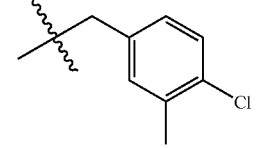 [SMILES: *Cc1ccc(Cl)c(C)c1] | H | H | H | H |
| 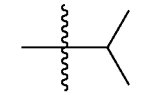 | | H | H | H | H |

TABLE 2-continued
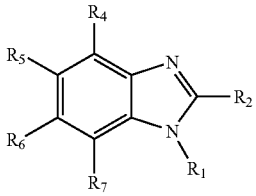
| R₁ | R₂ | R₄ | R₅ | R₆ | R₇ |
|---|---|---|---|---|---|
| 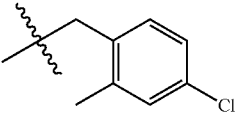 [SMILES: *Cc1ccc(Cl)cc1C] | 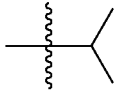 [SMILES: *C(C)C] | H | H | H | H |
| 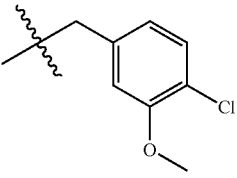 | 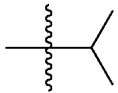 [SMILES: *C(C)C] | H | H | H | H |
| 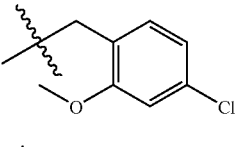 | 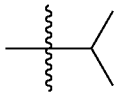 | H | H | H | H |
| 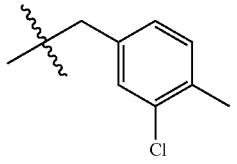 [SMILES: *Cc1ccc(C)c(Cl)c1] | 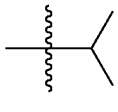 | H | H | H | H |
| 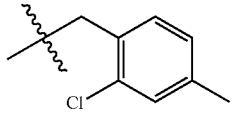 [SMILES: *Cc1ccc(C)cc1Cl] | 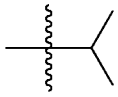 [SMILES: *C(C)C] | H | H | H | H |
| 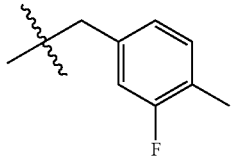 [SMILES: *Cc1ccc(C)c(F)c1] | 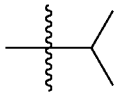 [SMILES: *C(C)C] | H | H | H | H |
| 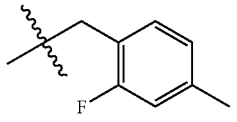 [SMILES: *Cc1ccc(C)cc1F] | 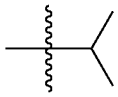 | H | H | H | H |
| 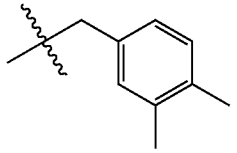 [SMILES: *Cc1ccc(C)c(C)c1] | 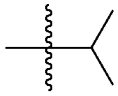 [SMILES: *C(C)C] | H | H | H | H |
| 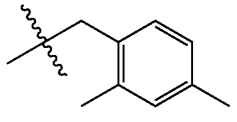 [SMILES: *Cc1ccc(C)cc1C] | 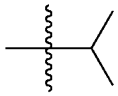 [SMILES: *C(C)C] | H | H | H | H |

TABLE 2-continued
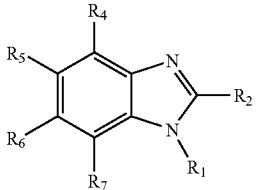
| R₁ | R₂ | R₄ | R₅ | R₆ | R₇ |
|---|---|---|---|---|---|
| 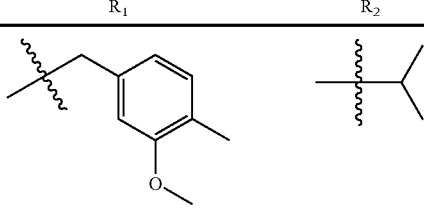 | 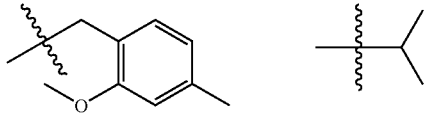 | H | H | H | H |
| 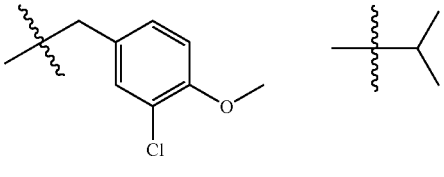 | 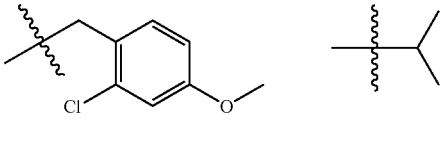 | H | H | H | H |
| 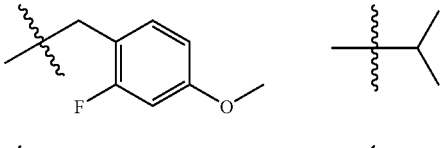 | 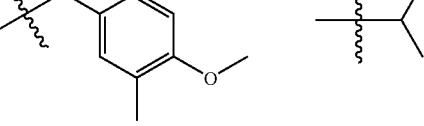 | H | H | H | H |
| 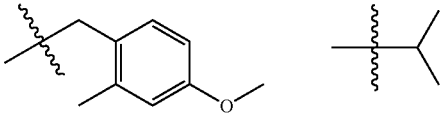 | 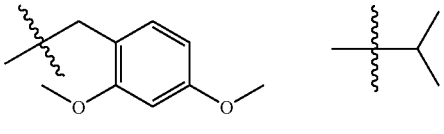 | H | H | H | H |
| 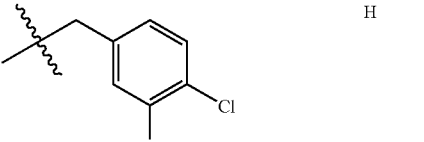 | | H | H | H | H |
| | | H | H | H | H |
| | | H | H | H | H |
| | | H | H | H | H |
| | H | H | CH₃ | CH₃ | H |

TABLE 2-continued
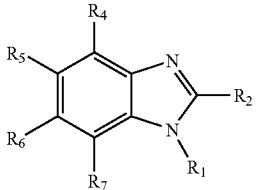
| R₁ | R₂ | R₄ | R₅ | R₆ | R₇ |
|---|---|---|---|---|---|
| 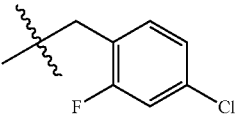 | H | H | CH₃ | CH₃ | H |
| 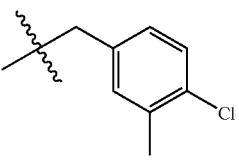 [SMILES: *Cc1ccc(Cl)c(C)c1] | H | H | CH₃ | CH₃ | H |
| 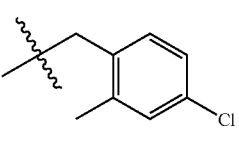 [SMILES: *Cc1ccc(Cl)cc1C] | H | H | CH₃ | CH₃ | H |
| 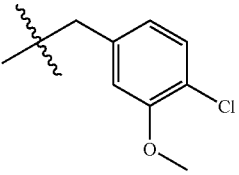 [SMILES: *Cc1ccc(Cl)c(OC)c1] | H | H | CH₃ | CH₃ | H |
| 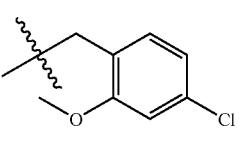 [SMILES: *Cc1ccc(Cl)cc1OC] | H | H | CH₃ | CH₃ | H |
| 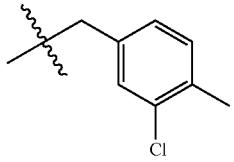 [SMILES: *Cc1ccc(C)c(Cl)c1] | H | H | CH₃ | CH₃ | H |
| 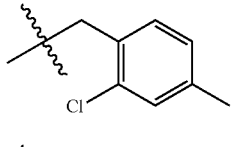 | H | H | CH₃ | CH₃ | H |
| 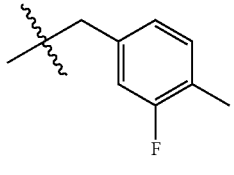 [SMILES: *Cc1ccc(C)c(F)c1] | H | H | CH₃ | CH₃ | H |
| 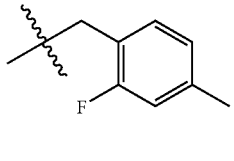 | H | H | CH₃ | CH₃ | H |

TABLE 2-continued
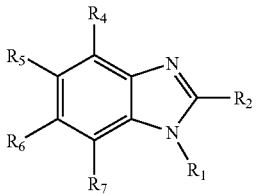
| R₁ | R₂ | R₄ | R₅ | R₆ | R₇ |
|---|---|---|---|---|---|
| 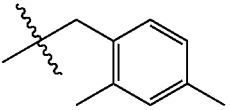 [SMILES: *Cc1ccc(C)cc1C] | H | H | CH₃ | CH₃ | H |
| 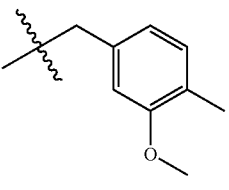 [SMILES: *Cc1ccc(C)c(OC)c1] | H | H | CH₃ | CH₃ | H |
| 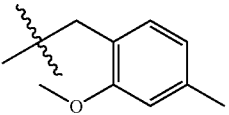 [SMILES: *Cc1ccc(C)cc1OC] | H | H | CH₃ | CH₃ | H |
| 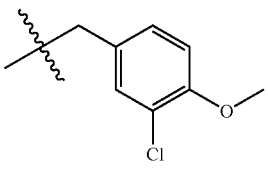 [SMILES: *Cc1ccc(OC)c(Cl)c1] | H | H | CH₃ | CH₃ | H |
| 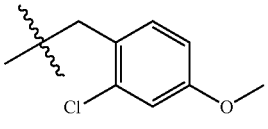 [SMILES: *Cc1ccc(OC)cc1Cl] | H | H | CH₃ | CH₃ | H |
| 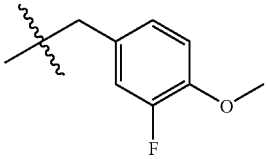 [SMILES: *Cc1ccc(OC)c(F)c1] | H | H | CH₃ | CH₃ | H |
| 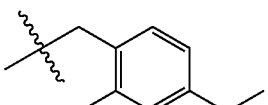 | H | H | CH₃ | CH₃ | H |
| 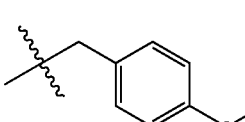 | H | H | CH₃ | CH₃ | H |
| 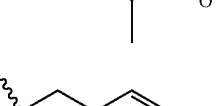 | H | H | CH₃ | CH₃ | H |

TABLE 2-continued
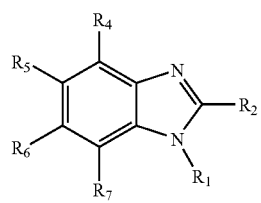
| $R_1$ | $R_2$ | $R_4$ | $R_5$ | $R_6$ | $R_7$ |
|---|---|---|---|---|---|
| 3,4-dimethoxybenzyl | H | H | $CH_3$ | $CH_3$ | H |
| 2,4-dimethoxybenzyl | H | H | $CH_3$ | $CH_3$ | H |
| 4-chloro-3-fluorobenzyl | $CF_3$ | H | H | H | H |
| 4-chloro-2-fluorobenzyl | $CF_3$ | H | H | H | H |
| 4-chloro-3-methylbenzyl | $CF_3$ | H | H | H | H |
| 4-chloro-2-methylbenzyl | $CF_3$ | H | H | H | H |
| 4-chloro-3-methoxybenzyl | $CF_3$ | H | H | H | H |
| 4-chloro-2-methoxybenzyl | $CF_3$ | H | H | H | H |

TABLE 2-continued
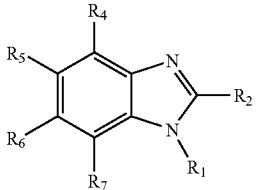
| R₁ | R₂ | R₄ | R₅ | R₆ | R₇ |
|---|---|---|---|---|---|
| 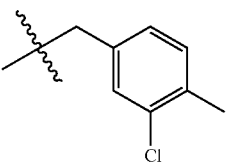 [SMILES: *Cc1ccc(C)c(Cl)c1] | CF₃ | H | H | H | H |
| 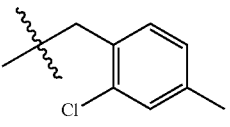 [SMILES: *Cc1ccc(C)cc1Cl] | CF₃ | H | H | H | H |
| 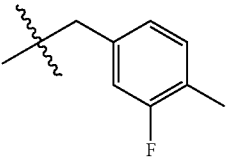 | CF₃ | H | H | H | H |
| 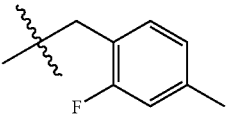 [SMILES: *Cc1ccc(C)cc1F] | CF₃ | H | H | H | H |
| 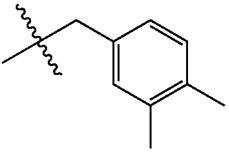 [SMILES: *Cc1ccc(C)c(C)c1] | CF₃ | H | H | H | H |
| 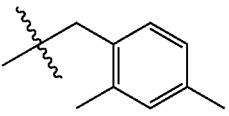 [SMILES: *Cc1ccc(C)cc1C] | CF₃ | H | H | H | H |
| 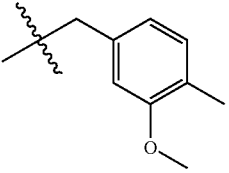 [SMILES: *Cc1ccc(C)c(OC)c1] | CF₃ | H | H | H | H |
| 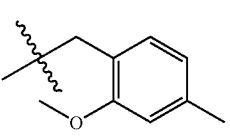 [SMILES: *Cc1ccc(C)cc1OC] | CF₃ | H | H | H | H |
| 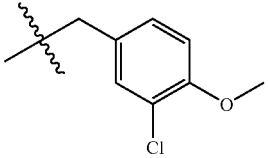 [SMILES: *Cc1ccc(OC)c(Cl)c1] | CF₃ | H | H | H | H |

TABLE 2-continued
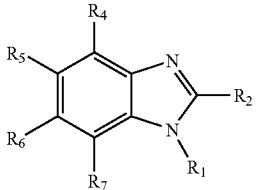
| R₁ | R₂ | R₄ | R₅ | R₆ | R₇ |
|---|---|---|---|---|---|
| 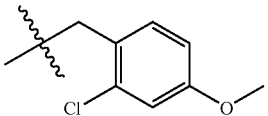 | CF₃ | H | H | H | H |
| 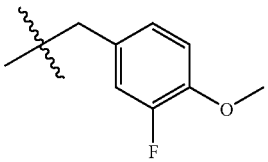 [SMILES: *Cc1ccc(OC)c(F)c1] | CF₃ | H | H | H | H |
| 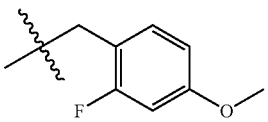 | CF₃ | H | H | H | H |
| 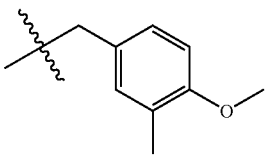 [SMILES: *Cc1ccc(OC)c(C)c1] | CF₃ | H | H | H | H |
| 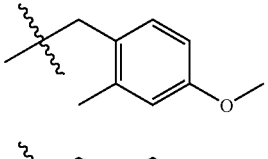 | CF₃ | H | H | H | H |
| 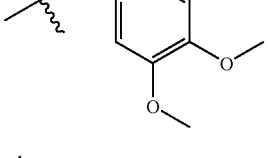 | CF₃ | H | H | H | H |
| 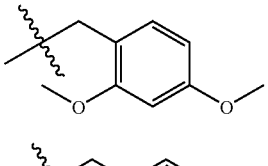 | CF₃ | H | H | H | H |
| 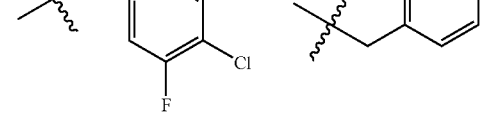 | 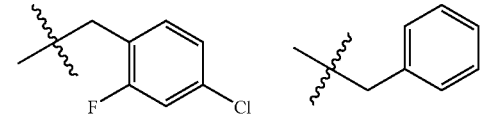 | H | H | H | H |

TABLE 2-continued
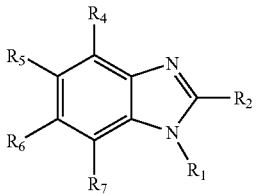

TABLE 2-continued
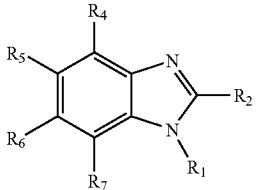
| R₁ | R₂ | R₄ | R₅ | R₆ | R₇ |
|---|---|---|---|---|---|
| 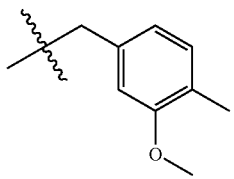 [SMILES: *Cc1ccc(C)c(OC)c1] | 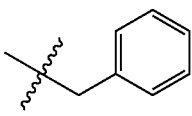 [SMILES: *Cc1ccccc1] | H | H | H | H |
| 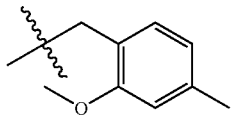 [SMILES: *Cc1ccc(C)cc1OC] | 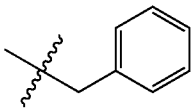 | H | H | H | H |
| 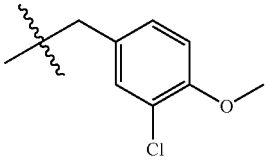 [SMILES: *Cc1ccc(OC)c(Cl)c1] | 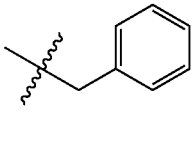 [SMILES: *Cc1ccccc1] | H | H | H | H |
| 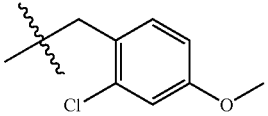 [SMILES: *Cc1ccc(OC)cc1Cl] | 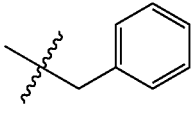 [SMILES: *Cc1ccccc1] | H | H | H | H |
| 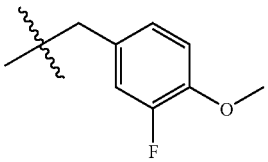 [SMILES: *Cc1ccc(OC)c(F)c1] | 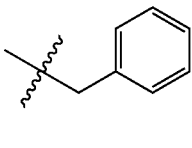 | H | H | H | H |
| 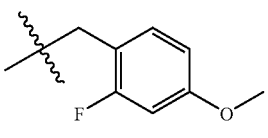 | 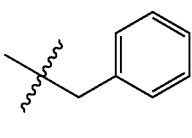 [SMILES: *Cc1ccccc1] | H | H | H | H |
| 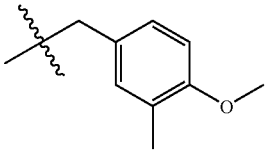 [SMILES: *Cc1ccc(OC)c(C)c1] | 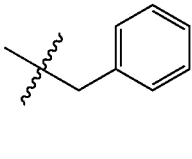 [SMILES: *Cc1ccccc1] | H | H | H | H |
| 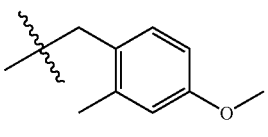 [SMILES: *Cc1ccc(OC)cc1C] | 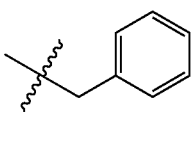 [SMILES: *Cc1ccccc1] | H | H | H | H |
| 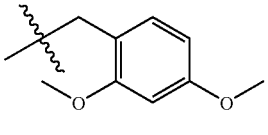 [SMILES: *Cc1ccc(OC)cc1OC] | 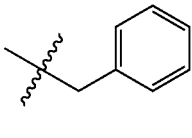 [SMILES: *Cc1ccccc1] | H | H | H | H |

TABLE 2-continued
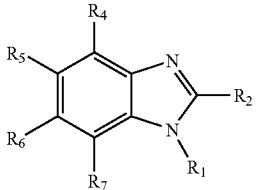
| R₁ | R₂ | R₄ | R₅ | R₆ | R₇ |
|---|---|---|---|---|---|
| 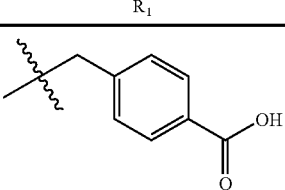 | CH₃ | H | CH₃ | CH₃ | H |
| 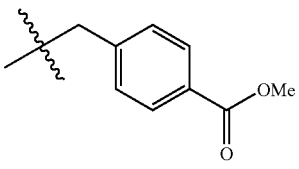 [SMILES: *Cc1ccc(C(=O)OC)cc1] | H | H | CH₃ | CH₃ | H |
| 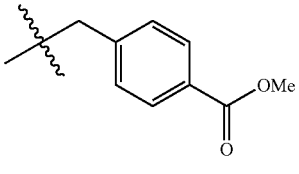 [SMILES: *Cc1ccc(C(=O)OC)cc1] | CH₃ | H | CH₃ | CH₃ | H |
| 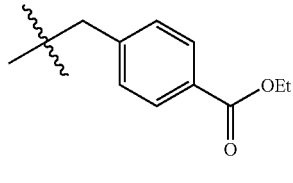 [SMILES: *Cc1ccc(C(=O)OCC)cc1] | H | H | CH₃ | CH₃ | H |
| 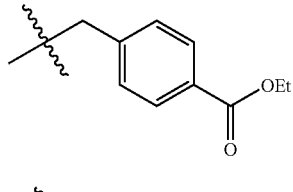 | CH₃ | H | CH₃ | CH₃ | H |
| 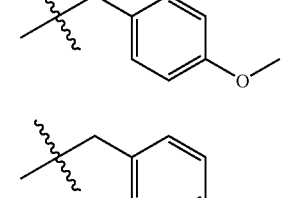 | CH₃ | H | CH₃ | CH₃ | H |
| 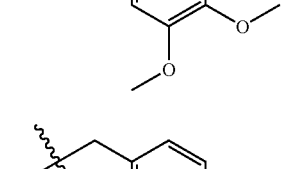 | H | H | CH₃ | CH₃ | H |
| 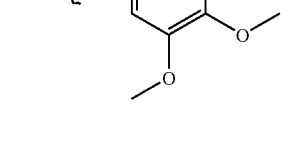 | CH₃ | H | CH₃ | CH₃ | H |

TABLE 2-continued
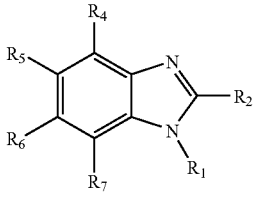
| R₁ | R₂ | R₄ | R₅ | R₆ | R₇ |
|---|---|---|---|---|---|
| 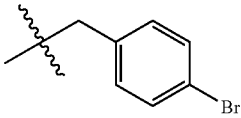 [SMILES: *Cc1ccc(Br)cc1] | H | H | Cl | Cl | H |
| 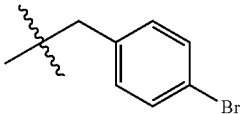 [SMILES: *Cc1ccc(Br)cc1] | CH₃ | H | Cl | Cl | H |
| 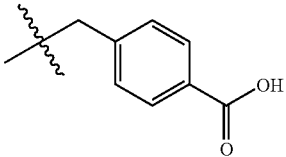 [SMILES: *Cc1ccc(C(=O)O)cc1] | H | H | Cl | Cl | H |
| 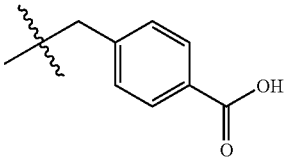 [SMILES: *Cc1ccc(C(=O)O)cc1] | CH₃ | H | Cl | Cl | H |
| 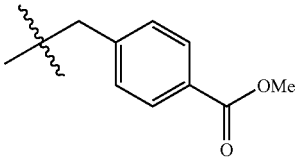 [SMILES: *Cc1ccc(C(=O)OC)cc1] | H | H | Cl | Cl | H |
| 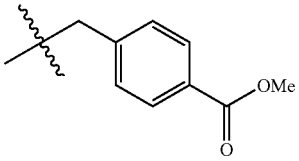 [SMILES: *Cc1ccc(C(=O)OC)cc1] | CH₃ | H | Cl | Cl | H |
| 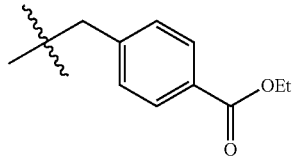 [SMILES: *Cc1ccc(C(=O)OCC)cc1] | H | H | Cl | Cl | H |
| 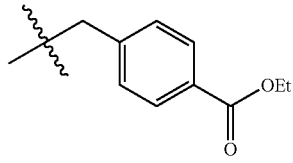 [SMILES: *Cc1ccc(C(=O)OCC)cc1] | CH₃ | H | Cl | Cl | H |

TABLE 2-continued
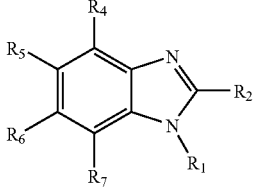
| R₁ | R₂ | R₄ | R₅ | R₆ | R₇ |
|---|---|---|---|---|---|
| 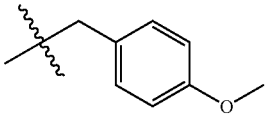 | H | H | Cl | Cl | H |
| 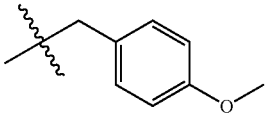 [SMILES: *Cc1ccc(OC)cc1] | CH₃ | H | Cl | Cl | H |
| 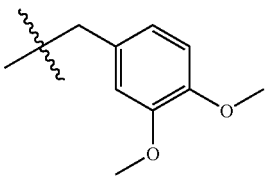 [SMILES: *Cc1ccc(OC)c(OC)c1] | H | H | Cl | Cl | H |
| 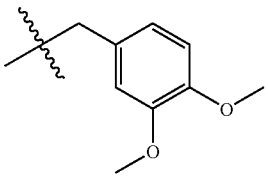 [SMILES: *Cc1ccc(OC)c(OC)c1] | CH₃ | H | Cl | Cl | H |
| 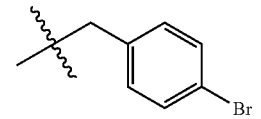 [SMILES: *Cc1ccc(Br)cc1] | H | H | OCH₃ | OCH₃ | H |
| 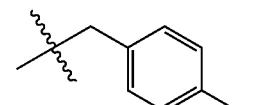 | CH₃ | H | OCH₃ | OCH₃ | H |
| 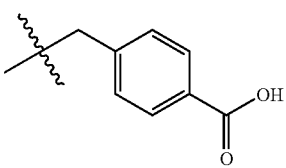 [SMILES: *Cc1ccc(C(=O)O)cc1] | H | H | OCH₃ | OCH₃ | H |
| 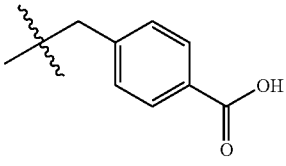 [SMILES: *Cc1ccc(C(=O)O)cc1] | CH₃ | H | OCH₃ | OCH₃ | H |

TABLE 2-continued

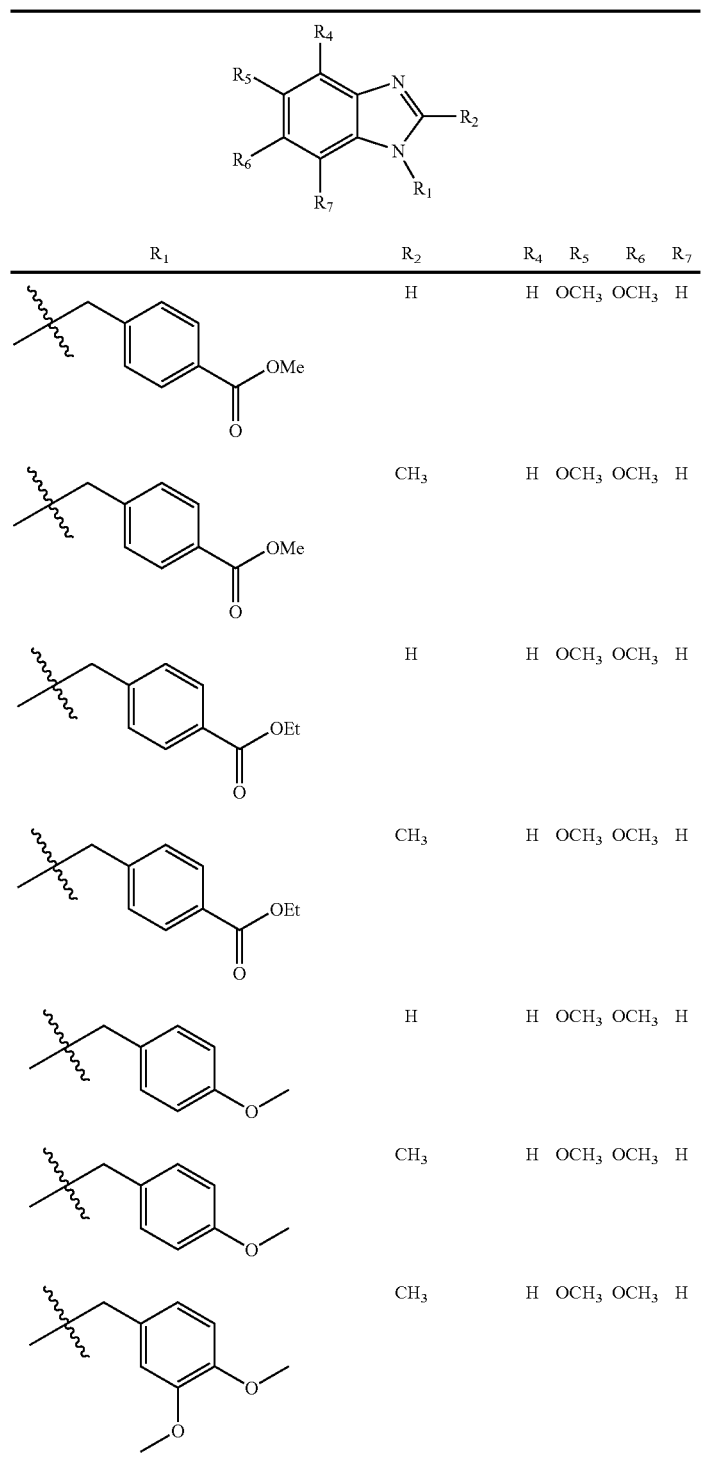

| $R_1$ | $R_2$ | $R_4$ | $R_5$ | $R_6$ | $R_7$ |
|---|---|---|---|---|---|
| (4-methoxycarbonylbenzyl) | H | H | OCH$_3$ | OCH$_3$ | H |
| (4-methoxycarbonylbenzyl) | CH$_3$ | H | OCH$_3$ | OCH$_3$ | H |
| (4-ethoxycarbonylbenzyl) | H | H | OCH$_3$ | OCH$_3$ | H |
| (4-ethoxycarbonylbenzyl) | CH$_3$ | H | OCH$_3$ | OCH$_3$ | H |
| (4-methoxybenzyl) | H | H | OCH$_3$ | OCH$_3$ | H |
| (4-methoxybenzyl) | CH$_3$ | H | OCH$_3$ | OCH$_3$ | H |
| (3,4-dimethoxybenzyl) | CH$_3$ | H | OCH$_3$ | OCH$_3$ | H |

Clemizole is an H1 receptor antagonist, and other H1 receptor antagonists that share structural similarity with clemizole may be useful in embodiments of the methods of the present invention. Illustrative H1 receptor antagonists that share structural similarity with clemizole include, but are not limited to, the compounds in the classes known as alcoholamines (e.g., diphenhydramine, carbinoxamine, and clemastine), ethylenediamines (e.g., mepyramine and tripelennamine (clemizole is in this class)), alkylamines (e.g., triprolidine and chlorpheniramine), piperazines (e.g., meclizine and homochlorcyclizine), and phenothiazines (e.g., promethazine).

Embodiments of the present invention include prodrugs of clemizole, clemizole analogs, and compounds having a clemizole scaffold, and their isosteres, that are activated by liver enzymes (e.g., cyclic-1,3-propanyl esters substituted with groups that promote an oxidative cleavage reaction by CYP3A, etc.). These modifications can render clemizole inactive or less active until activated in the liver (see, Current Opinion in Investigational Drugs 2006 Vol 7 No 2, 109-117; J. Med. Chem. 2008, 51, 2328-2345; and Nucleosides, Nucleotides, and Nucleic Acids, 24 (5-7):375-381, (2005), each of which is incorporated herein by reference for the corresponding discussion.

Clemizole was described in 1952 by Zierz and Greither (Artztliche Wochenschrift 7:30, 704-7, Clinical evaluation of Allercur, a new antihistamine), reporting on a product from Schering AG. Finkelstein et al. ((1960) J Am Pharm Assoc Am Assoc; 49:18-22) reported on the pharmacology of clemizole hydrochloride, stating that it demonstrated effective prolonged antihistamine activity and a relatively high degree of antihistaminic specificity and was very effective in antagonizing histamine aerosol bronchospasm. Spontaneous activity of isolated rabbit ileum and intestinal motility in anesthetized dogs were reportedly decreased, and there was no significant effect on histamine-induced gastric secretion in chronic gastric fistula dogs, indicating the selectivity for H1 receptors.

A. A. Jacques and V. H. Fuchs (1960, International *Record of Medicine*, "Clinical Evaluation of Clemizole in Allergic Rhinitis") reported that clemizole was made available for clinical investigation in the management of allergic disorders. They reported that the antihistaminic activity of clemizole was evaluated in the guinea pig and man and that clemizole was superior to atropine and other antihistamines in preventing histamine-induced asthma in the guinea pig. Histamine and mixtures of histamine and clemizole were compared by effects produced with subcutaneous injection in human subjects. The addition of clemizole to histamine reportedly caused a reduction in the histamine induced wheals and in the pain of injection. Clemizole was selected for this investigation on the basis of previous clinical reports of prompt relief of allergic symptoms and the remarkably low incidence of side effects, with excellent clinical results reported in more than 500 patients suffering from seasonal and perennial hay fever and various dermatological conditions (e.g., urticaria, neurodermatitis, eczema, food and drug allergies). As summarized by Jacques and Fuchs, previous clinical experience with clemizole indicated that the antihistamine is exceptionally well tolerated on prolonged administration.

Zierz and Greither reported drowsiness in only 1.3 percent of the patients treated, and Dulce observed no side reactions, even with daily doses of 120 mg. Twenty-four patients given 90 to 300 mg of clemizole daily for periods up to five days reported only slight fatigue and, less frequently, gastric pressure. Patients who had shown poor tolerance to other antihistamines were reported to have no reactions to clemizole. In children, administration of clemizole produced no signs of intolerance. Adults and children were given clemizole tannate or clemizole hydrochloride for relief of symptoms associated with allergic rhinitis, asthma, vasomotor rhinitis, and various coincident conditions. Symptoms included those commonly associated with allergy-rhinorrhea, sneezing, postnasal drip, lachrymation, and itchy nose and eyes. Three dosage forms were included in the study and generally were employed according to the age of the patient and the severity of the symptoms. Four adults received 10 mg (1 ml) of clemizole intramuscularly alone, while an additional 3 patients received a single 10 mg (1 ml) dose of clemizole hydrochloride intramuscularly, followed by 2 teaspoonfuls of the oral suspension taken four times daily for five days. Other patients received 1 or 2 tablets (20 or 40 mg total dose) of clemizole hydrochloride two to four times daily for periods of one or two weeks; 1 adult received 1 tablet six times daily for one week. Other patients received one or two teaspoonfuls (20 or 40 mg total dose of clemizole as the hydrochloride) of the oral suspension, two to four times daily for five to six days. Of the 104 subjects given clemizole in its various dosage forms, 92 responded to treatment. Clemizole was particularly effective in the relief of sneezing and rhinorrhea. It was concluded that clemizole appears to be an effective antihistamine with a remarkably low incidence of side effects. Drowsiness was the only untoward effect attributed to the use of the drug; this side reaction was evident in only 2 of the 104 patients treated and did not necessitate interruption of therapy.

B. A. Wansker (1962, *Skin*, "Clemizole Hydrochloride: A Clinical Evaluation of its Antipruritic Effect") reported on a clinical study conducted on a random selection of patients whose itching was a prominent symptom of a dermatologic disease. The criterion of effectiveness was relief of itching. Dosages of clemizole hydrochloride were individualized according to the severity of the pruritus. The majority of patients received 20 mg 3 times during the day plus 40 mg at bedtime, for a total of 100 mg during a 24-hour period. In all, dosages ranged from 40 to 160 mg daily. Duration of treatment varied from 1 to 12 weeks. Forty-three patients were treated for 2 or less weeks, and 24 were treated for more than 2 weeks. No patient was treated less than 1 week. 77 patients received either clemizole (in the form of 20 mg tablets) or placebo (identically-appearing corn starch and lactose tablets). Patients were treated with 40 to 160 mg/day (most received 100 mg). 24 patients were treated for more than 2 weeks, with some treated for up to 12 weeks. 66% reported excellent and 23% good relief of itching. Mild side effects in 4 patients (drowsiness most common) were noted. It was concluded that clemizole hydrochloride is a safe, well-tolerated drug. The compound is essentially free of clinically observable side effects and appears to act quite promptly—usually within 24 to 48 hours—in its ability to relieve itching.

Clemizole was marketed in the United States as Allercur®, a product of J. B. Roerig and Company, Div., Chas. Pfizer & Co., Inc. The trade name of J. B. Roerig & Co. Division, Chas. Pfizer & Co., Inc., for clemizole tannate was Allercur oral suspension; for clemizole hydrochloride, Alkrcur parenteral and Allercur tablets. The 1966 PDR touted clemizole's advantage as: exceptionally well tolerated. However, the drug is not currently marketed in the U.S., although the compound is readily available in pure form from Sigma-Aldrich.

In accordance with an embodiment of the present invention, a simple and convenient dosing regimen for treating patients with an HCV infection includes any regimen previously shown effective for use of clemizole as an antipruritic. In one embodiment, a BID dosing regimen is employed. In one embodiment, the regimen is 100 mg po BID. Embodiments of the invention provides novel unit dose forms of clemizole, including 25 mg, 50 mg, 75 mg, 100 mg, 125 mg, 150 mg, and 200 mg unit dose forms. In one embodiment, the unit dose form is a tablet; in another, the unit dose form is a capsule. In one embodiment, sustained release formulations of clemizole are in the tablet and capsules provided by the invention. In another embodiment, the unit dose form is a liquid.

Three patients chronically-infected with HCV (genotype 4) were treated in accordance with an embodiment of the method of the invention. All were male and had baseline ALT elevations and significant HCV viral loads ranging from 290,000-730,000 IU/ml. All experienced drops in HCV viral load when next measured at week 2 of the clemizole dosing regimen (100 mg po BID), and by week 4, all had HCV levels nearly at or below the limit of HCV detection. It is likely that, had the measurement of viral load been performed after a few more days of clemizole monotherapy treatment, all patients would have had HCV levels below the limit of detection. Following 4 weeks of clemizole monotherapy, plus 4 weeks of therapy with clemizole-standard dose pegylated interferon, all patients' HCV viral load was below the limit of detection.

Because clemizole has been demonstrated in accordance with embodiments of the methods of the invention to have anti-HCV activity against genotypes 1, 2, and 4 (which span the gamut of HCV genotypes in terms of evolutionary age and response to interferon), clemizole should be ideal for treating all patients with HCV, regardless of genotype.

Efficacious dosing of clemizole in accordance with embodiments of methods of the invention also includes dosing at 150 mg po BID, 75 mg po BID, and 50 mg po BID. The total daily dose can also be split among multiple doses, which allows for a lower dose at each administration with less potential for sedation while maintaining sufficient efficacy. Alternatively, and particularly for harder to treat cases, a more frequent dosing schedule in accordance with the methods of the invention (for example TID administration or administration every 4 or 6 hours) of a 25 mg, 50 mg, 75 mg, 150 mg or higher dose) can be used.

Similarly, the sustained release formulations of embodiments of the invention can help maintain viral-inhibiting concentrations over a longer time interval. The sustained release formulation dose is, in illustrative embodiments, 50, 75, 100, and 150 mg po BID, and 100, 150, 200, and 300 mg po qd. Clemizole can also be administered by transdermal, sublingual, intramuscular, or rectal routes in accordance with embodiments of the methods of the invention. In one embodiment, clemizole is administered to a patient with HCV but with no other condition requiring treatment with an antihistamine. In another embodiment, the patient has HCV and a condition requiring treatment with an antihistamine, and clemizole and an antihistamine other than clemizole are used in combination to treat the patient's HCV infection and condition requiring antihistamine therapy, respectively.

While, in the 3 patients described above, clemizole monotherapy was stopped at 4 weeks, it could in accordance with the methods of the invention have continued as monotherapy for up to 12, 24, 36, or 48 or more weeks to provide a sustained virologic response, and in some embodiments of the invention dosing is continued indefinitely or continued until further treatment is no longer of apparent benefit.

In the case of patients who will be undergoing liver transplantation for HCV-associated end stage liver disease (ESLD), it is known that there is a ~100% chance of the new graft becoming infected with HCV if viremia is present at the time of transplantation. It is also known, however, that effective treatment of HCV prior to transplantation can reduce or eliminate the recurrence of HCV in the new graft. Thus, treatment with clemizole monotherapy in accordance with the methods of the invention can be performed to reduce or eliminate HCV viral load prior to liver transplantation, and can help prevent the recurrence of HCV after transplantation. Moreover, often pre-transplant patients with ESLD, or post-transplant patients with HCV recurrence, cannot tolerate full doses of standard of care therapy (pegylated interferon and ribavirin). Thus, either clemizole monotherapy, or clemizole plus reduced doses of pegylated interferon and ribavirin, can be used to treat these patients in accordance with the methods of the invention. Similarly, clemizole plus nitazoxanide (or another thiazolide, or sustained formulations of either of these) can be used to treat these patients, as can clemizole plus nitazoxanide (or another thiazolide, or sustained formulations of either of these) plus standard of care medications (at reduced or regular doses, as tolerated).

The patients treated with 4 weeks of clemizole monotherapy, followed by 4 weeks of clemizole and standard dose pegylated interferon, were then further treated with nitazoxanide and pegylated interferon combination therapy. However, in accordance with the methods of the invention, the combination of clemizole and pegylated interferon could be continued for a total of 12, 24, 36, or 48 or more weeks of interferon to help promote a sustained virologic response. Similarly, ribavirin could be added to the period of treatment with pegylated interferon (or from the onset of therapy) to provide triple combination therapy during the interferon treatment interval. Alternatively, nitazoxanide could be used along with pegylated interferon, or along with pegylated interferon and ribavirin, in such treatments.

Similarly, the clemizole monotherapy period in the above-described regimens could be, for example and without limitation, 4 weeks or 12 weeks. It could also be, in other embodiments, 3 days, 7 days, or 2 weeks, or clemizole combination therapy can be initiated immediately (i.e., no clemizole monotherapy treatment phase) in accordance with the methods of the invention.

Combination therapy with clemizole in accordance with embodiments of the methods of the invention includes, for example and without limitation, treatment with clemizole plus nitazoxanide, treatment with clemizole followed by nitazoxanide, treatment with clemizole plus nitazoxanide and a NS3 protease inhibitor, treatment with clemizole plus nitazoxanide plus a NS3 protease inhibitor plus a NS5B polymerase inhibitor, treatment with clemizole plus a NS3 protease inhibitor plus a NS5B polymerase inhibitor, treatment with clemizole plus nitazoxanide plus a NS3 protease inhibitor plus a NS4B second amphipathic helix inhibitor, treatment with clemizole plus nitazoxanide plus a NS4B second amphipathic helix inhibitor, treatment with clemizole plus a NS3 protease inhibitor plus a NS4B second amphipathic helix inhibitor, and all of the above with the addition of ribavirin, clemizole plus ribavirin, clemizole followed by nitazoxanide plus ribavirin.

Nitazoxanide administration in accordance with the combination therapies of the invention can be, for illustration and without limitation, 500 mg po BID. Other doses, other thiazolides, or other formulations of nitazoxanide or another thiazolide, such as sustained release formulations, can also be used in the combination therapies of the invention.

In other methods and unit dose forms provided by embodiments of the invention, clemizole derivatives and analogs described herein are used instead of clemizole in the above treatment methods and unit dose forms.

Additional H1 receptor antagonists, which may be useful in the methods of the present disclosure, include:

Piperazines: Buclizine, Chlorocyclizine, Cinnarizine, Clocinizine, Hydroxyzine, Niaprazine, Oxatomide, Benzhydryl compounds (Cyclizine, Meclizine), Levocetirizine, and Cetirizine.

Tricyclics and Tetracyclics: Ahistan, Etymemazine, Hydroxyethylpromethazine, Isopromethazine, Isothipendyl, Mequitazine, Methdilazine, Oxomemazine, Promethazine, Thiazinamium, Azatadine, Clobenzepam, Cyproheptadine, Deptropine, Isothipendyl, Loratidine, Pimethixene, Rupatadine, Desloratidine, Ketotifen, and Alimemazine.

Others: Astemizole, Azelastine, Bepottastine, Bamipine, Cetoxine, Clemizole, Clobenztropine, Deptropine, Dimebon, Ebastine, Emedastine, Epinastine, Levocabastine, Mebhydrolin, Mizolastine, Phenindamine, Tritoqualine, Terfenadine, and Fexofenadine.

Illustrative H1 antagonists useful in the embodiments of the methods of the invention include those compounds in the classes shown below.

In an embodiment, the H1 antagonists useful in the methods of the invention can include ethanolamines/alkylamines having the general formula as described by the following structures:

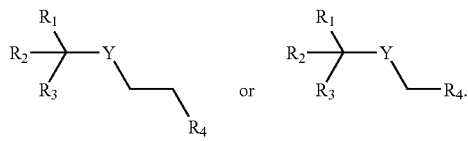

In each of the two structures shown above, $R_1$ and $R_2$ are each independently aryl (e.g., Groups A-F shown above); $R_3$ is selected from the group consisting of: —H and —CH$_3$; Y is selected from the group consisting of: —CH$_2$— or —O—; and $R_4$ is selected from the group consisting of:

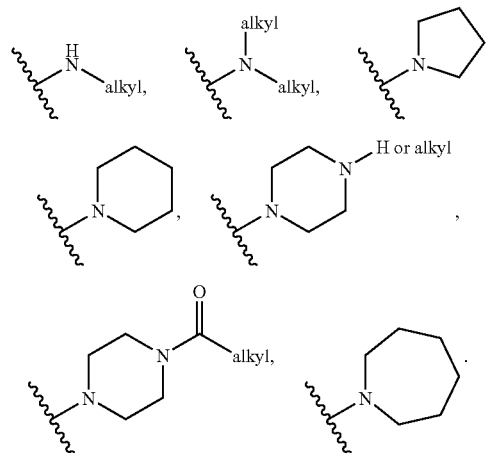

In an embodiment, the alkyl groups can be selected from the preferred embodiments described in this section.

In an embodiment, the H1 antagonists can include ethylenediamines having the general formula as described by the following structure:

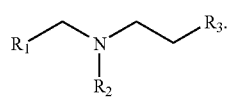

In the structure shown above, $R_1$ and $R_2$ are each independently aryl (e.g., Groups A-F shown above) and $R_3$ is selected from the group consisting of:

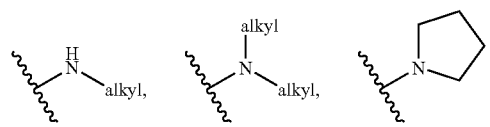

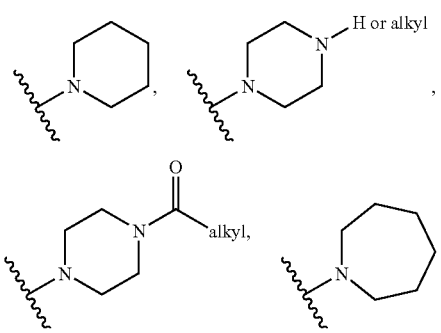

In an embodiment, the alkyl groups can be selected from the preferred embodiments described in this section.

In an embodiment, the H1 antagonists can include piperazines having the general formula as described by the following structure:

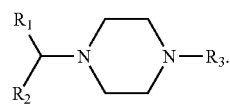

In the structure shown above, $R_1$ and $R_2$ are each independently selected from aryl (e.g., Groups A-F shown above) and $R_3$ is selected from the group consisting of the following structures:

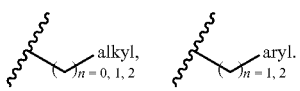

In an embodiment, the aryl and the alkyl groups can be selected from the preferred embodiments described in this section.

In an embodiment, the H1 antagonists can include compounds having the following structures:

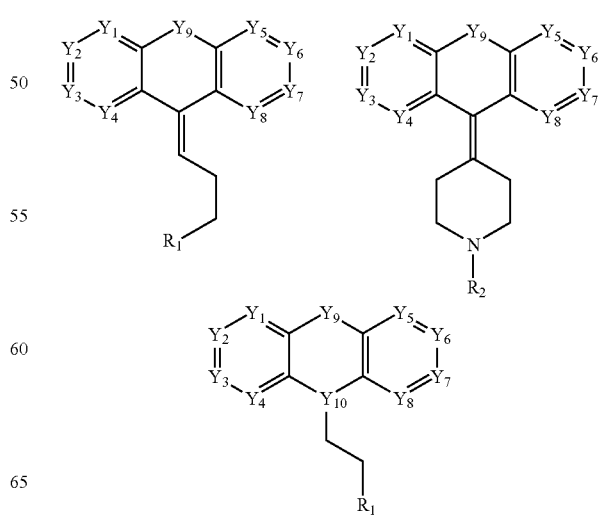

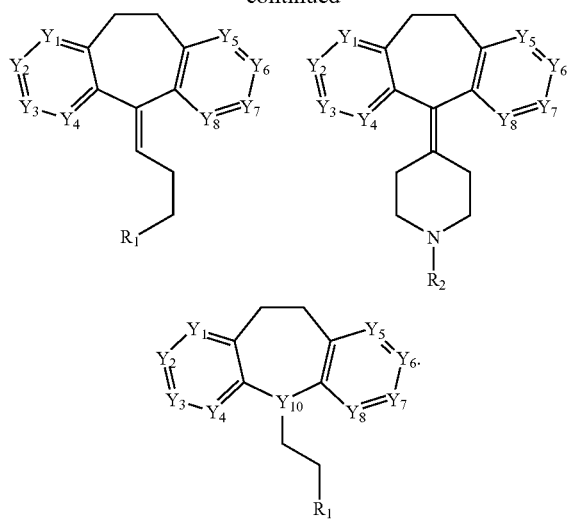

In the structures shown above, $Y_1$-$Y_4$ and $Y_5$-$Y_8$ are independently selected from the group consisting of: —N—, —CH—, and —CR, where R is selected from the group consisting of: —CH$_3$, —F, —Cl, —OCH$_3$. In an embodiment, one or fewer of $Y_1$-$Y_4$ is —N— and one or fewer of $Y_5$-$Y_8$ is —N—. $Y_9$ is selected from the group consisting of: —CH$_2$—, —O—, and —S—. $Y_{10}$ is selected from the group consisting of: —CH— and —N—. $R_2$ is alkyl (e.g., such as an alkyl shown in the preferred embodiments of this section). $R_1$ is selected from the group consisting of:

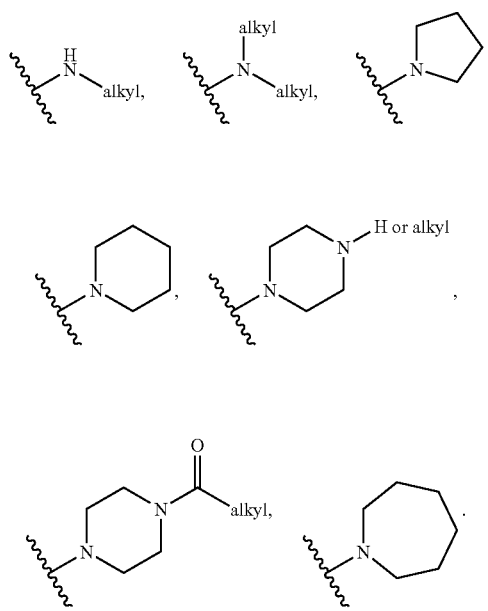

In an embodiment, the aryl and the alkyl groups can be selected from the preferred embodiments described in this section.

As described in the examples below, aurintricarboxylic acid (structure is below) is an inhibiting agent; however, it is a non-specific inhibitor of DNA:protein interactions and so not preferred for use as a drug.

[structure of aurintricarboxylic acid]

As noted above, embodiments of the inhibiting agent include compounds in one or more of the following groups: norepinephrine, norepinephrine analogs, and compounds having a norepinephrine scaffold. The following shows the general structure of a norepinephrine scaffold.

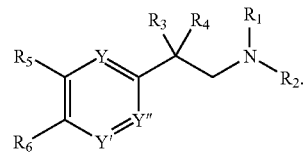

In the norepinephrine scaffold structure shown above, Y, Y', and Y'' are independently selected from the group consisting of: —N—, CH—, and —CR, where R is selected from —CH$_3$, —F—, —Cl, and —OCH$_3$; $R_1$ and $R_2$ are independently selected from the group consisting of: H and alkyl; and $R_3$ and $R_4$ are independently selected from the group consisting of: —H and one of the following: —H, —CH$_3$, —OH, and —O-alkyl, where in an embodiment the alkyl group is selected from the alkyl groups described in the preferred embodiments described in this section.

In an embodiment, $R_3$ and $R_4$ are connected by a ring containing between 3 and 7 atoms. In an embodiment, the ring is a spiro-cyclopropyl, where $R_3$ and $R_4$ are each —CH$_2$—CH$_2$—.

In an embodiment, $R_5$ and $R_6$ are each independently selected from the group consisting of: —H, —Cl, —F, -alkyl, —OH, and —O-alkyl, where in an embodiment the alkyl group is selected from the alkyl groups described in the preferred embodiments described in this section.

In an embodiment, $R_5$ is either —OH or —O-alkyl, while $R_6$ is selected from the group consisting of: —H, —Cl, —F, -alkyl, and —O-alkyl, where in an embodiment the alkyl group is selected from the alkyl groups described in the preferred embodiments described in this section.

In another embodiment, $R_6$ is either —OH or —O-alkyl, while $R_5$ is selected from the group consisting of: —H, —Cl, —F, -alkyl, or —O-alkyl, where in an embodiment the alkyl group is selected from the alkyl groups described in the preferred embodiments described in this section.

In an embodiment, $R_5$ and $R_6$, together with C atoms to which they are attached form a ring containing between 5 and 7 atoms.

In an embodiment, the ring is selected from the group consisting of following structures:

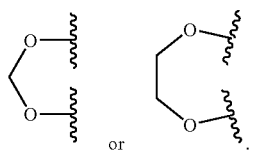 [SMILES: *OCO* ; *OCCO* ; "or" ; "."]
or

Embodiments of the inhibiting agent include compounds in one or more of the following groups: norepinephrine, norepinephrine analogs, and compounds having a norepinephrine scaffold. The norepinephrine scaffold has the following general structure:

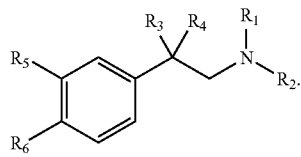

In the structure shown above, $R_1$ and $R_2$ are independently selected from the group consisting of: —H, —CH$_3$, —CH$_2$CH$_3$, —CH(CH$_3$)$_2$, and —CH$_2$CH(CH$_3$)$_2$; $R_3$ and $R_4$ are independently selected from the group consisting of: —H, —CH$_3$, —CH$_2$CH$_3$, —CH(CH$_3$)$_2$, —CH$_2$CH(CH$_3$)$_2$, —OH, and —OCH$_3$; $R_5$ and $R_6$ are independently selected from the group consisting of: —H, —CH$_3$, —CH$_2$CH$_3$, —CH(CH$_3$)$_2$, —CH$_2$CH(CH$_3$)$_2$, —OH, —OCH$_3$, Cl, F, Br, and CF$_3$.

Embodiments of the inhibiting agent include compounds in one or more of the following groups: caffeine analogs and caffeine (shown below).

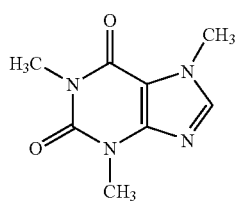

Embodiments of the inhibiting agent include compounds in one or more of the following groups: cinoxacin (structure on the right), cinoxacin analogs, and compounds having a cinoxacin scaffold. The cinoxacin scaffold has the following general structure (structure on left):

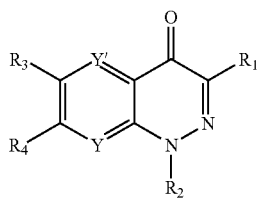

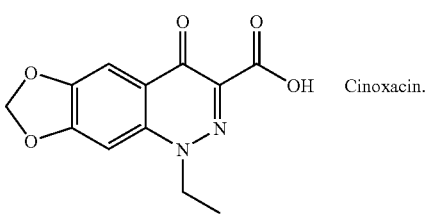
Cinoxacin.

In the cinoxacin scaffold shown above, Y and Y' are independently selected from the group consisting of: —N— or —CH—; $R_1$ is selected from the group consisting of:

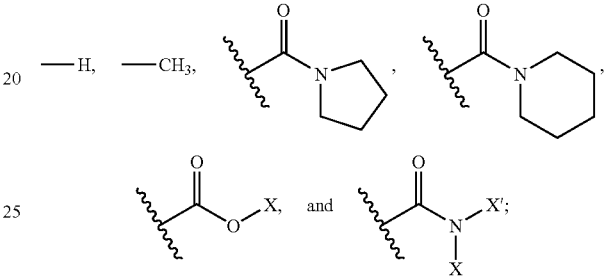

X and X' are independently the group consisting of —H and -alkyl; and $R_2$ is selected from the group consisting of:

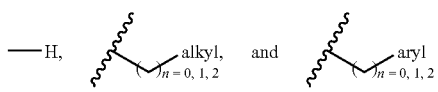

where in an embodiment the alkyl group is selected from the alkyl groups described in the preferred embodiments described in this section.

In an embodiment, $R_3$ and $R_4$ are independently selected from the group consisting of: —H, —Cl, —F, —CH$_3$, and —OCH$_3$. In another embodiment, $R_3$ and $R_4$ are each independently substituted with one group selected from the group consisting of: —Cl, —F, —CH$_3$, and —OCH$_3$.

In another embodiment, $R_3$ and $R_4$ are connected by a ring containing between 5 and 7 atoms. In an embodiment, the ring is formed from a structure selected from the group consisting of:

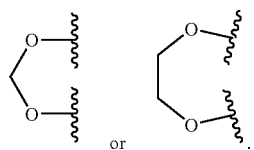 [SMILES: *OCO* ; *OCCO* ; "or" ; "."]
or

In an embodiment of the cinoxacin scaffold, Y is selected from the group consisting of: CH, CCH$_3$, N, CCl, and CF; Y' is selected from the group consisting of: CH, CCH$_3$, N, CCl, and CF; $R_1$ is selected from the group consisting of: —CO$_2$H, —CO$_2$CH$_3$, —CO$_2$CH$_2$CH$_3$, and —CONCH$_3$; and $R_2$ is selected from the group consisting of:

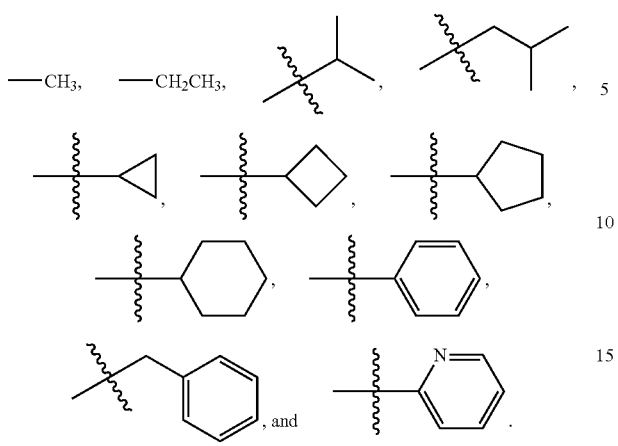

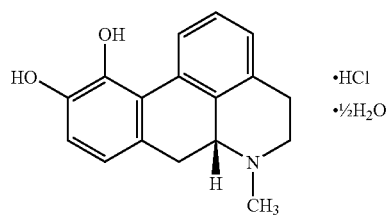

Embodiments of the inhibiting agent include compounds in one or more of the following groups: glybenclamide, glybenclamide analogs, and compounds having a glybenclamide scaffold. The structure of glybenclamide scaffold is shown on the left and the structure is of glybenclamide is shown on the right.

In an embodiment, the cinoxacin scaffold has the following general structure:

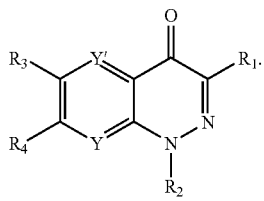

Y is selected from the group consisting of: CH, CCH$_3$, N, CCl, and CF; Y' is selected from the group consisting of: CH, CCH$_3$, N, CCl, and CF; R$_1$ is selected from the group consisting of: —CO$_2$H, —CO$_2$CH$_3$, —CO$_2$CH$_2$CH$_3$, and —CONCH$_S$; R$_2$ is selected from the group consisting of:

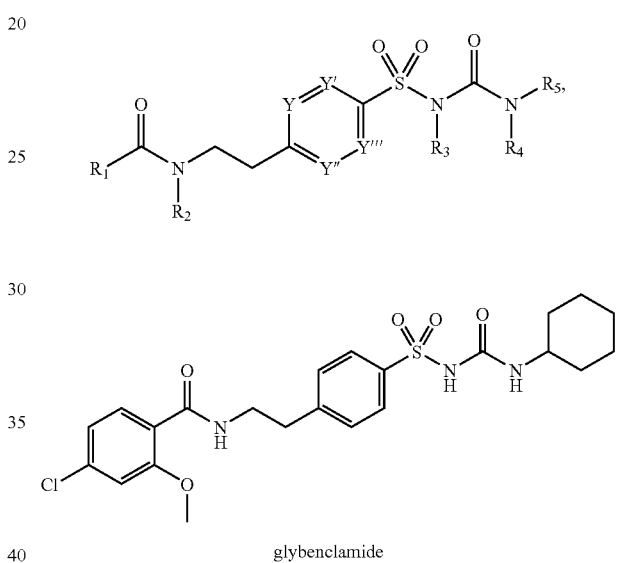

glybenclamide

In the glybenclamide scaffold shown above, Y, Y', Y", and Y'" are independently selected from the group consisting of: —N—, —CH—, and —C—X. In an embodiment, one or fewer of Y, Y', Y", and Y'" is —N— and one or fewer of Y, Y', Y", and Y'" is —C—X. X is selected from the group consisting of: —CH$_3$, —F, —Cl—, and —OCH$_3$.

R$_1$ is aryl, where in an embodiment the aryl group is selected from the aryl groups described in the preferred embodiments described in this section; and R$_2$, R$_3$, and R$_4$ are independently selected from the group consisting of: —H, —CH$_3$, —CH$_2$CH$_3$, and isopropyl. In an embodiment, two or more of R$_2$, R$_3$, and R$_4$ are —H.

R$_5$ is selected from one of the group consisting of:

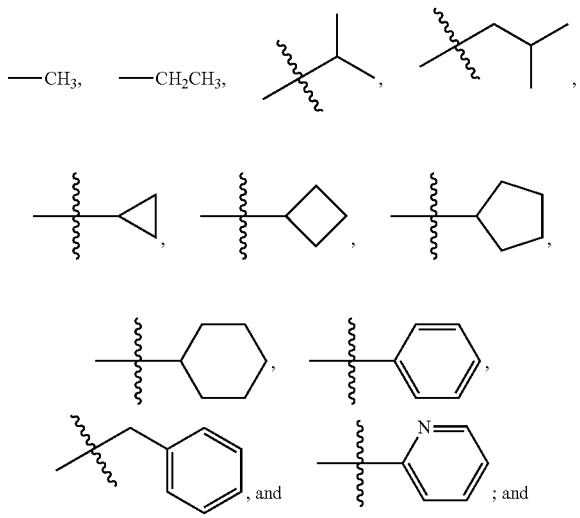

R$_3$ and R$_4$ are independently selected from the group consisting of: —OCH$_3$, —CH$_3$, Cl, and F.

Embodiments of the inhibiting agent include R-(−)-apomorphine hydrochloride hemihydrate, and R-(−)-apomorphine hydrochloride hemihydrate analogs.

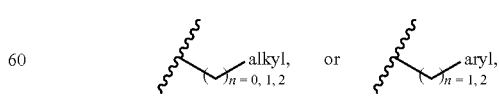

where in an embodiment the alkyl group is selected from the alkyl groups described in the preferred embodiments described in this section. In an embodiment, R$_5$ is selected from one of the group consisting of:

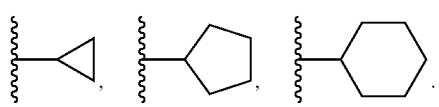

Embodiments of the inhibiting agent include glybenclamide analogs and compounds having a glybenclamide scaffold. The structure of the glybenclamide scaffold is shown below:

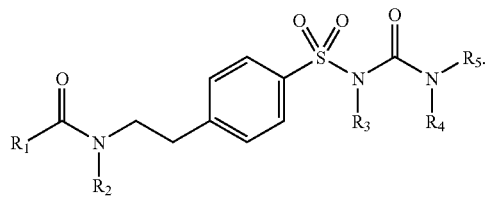

In the glybenclamide scaffold shown above, $R_1$ is selected from the group consisting of:

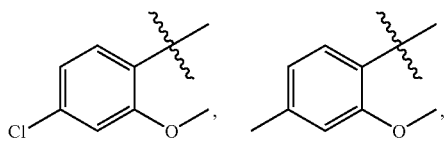

and $R_4$ are independently selected from the group consisting of: H, $CH_3$, $CH_2CH_3$, and $CH(CH_3)_2$; and $R_5$ is selected from the group consisting of:

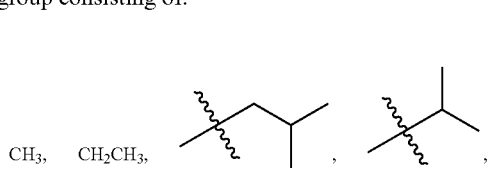

Embodiments of the inhibiting agent include R(−)-N-Allylnorapomorphine hydrobromide (shown below), and R(−)-N-Allylnorapomorphine hydrobromide analogs.

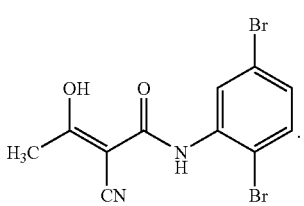 [SMILES: C/C(O)=C(\C#N)C(=O)Nc1cc(Br)ccc1Br ; "."]

Embodiments of the inhibiting agent include LFM-A13 (shown below) and LFM-A13 analogs.

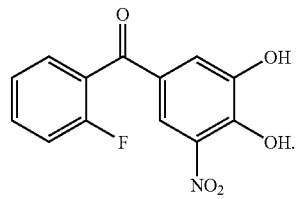 [SMILES: O=C(c1cc(O)c(O)c([N+](=O)[O-])c1)c1ccccc1F]

Embodiments of the inhibiting agent include Ro 41-0960 (shown below), and Ro 41-0960 analogs.

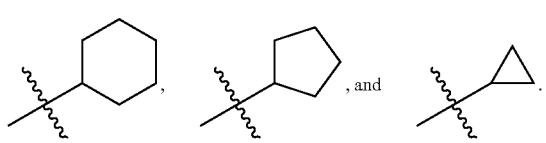

Embodiments of the inhibiting agent include compounds in one or more of the following groups: tropicamide, tropicamide analogs, and compounds having a tropicamide scaffold. The structure of the tropicamide scaffold is shown on the left and the structure of tropicamide is shown on the right.

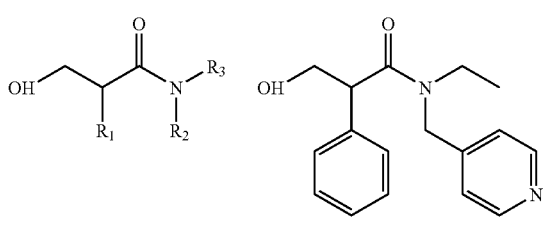

Tropicamide

In the tropicamide scaffold shown above, $R_1$ is aryl, where in an embodiment the aryl group is selected from the aryl groups described in the preferred embodiments described in this section. In an embodiment, $R_1$ is phenyl. $R_2$ is

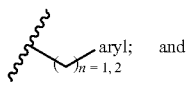

R₃ is alkyl, where in an embodiment the alkyl group and the aryl group are independently selected from the alkyl groups and aryl groups described in the preferred embodiments described in this section.

Embodiments of the inhibiting agent include (±)-thalidomide and (±)-thalidomide analogs. In one embodiment of the invention, the inhibiting agent is a compound other than thalidomide or a thalidomide analog.

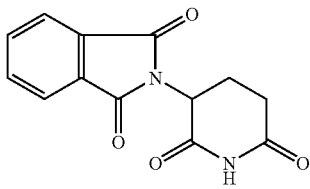 [SMILES: O=C1CCC(N2C(=O)c3ccccc3C2=O)C(=O)N1]

Embodiments of the inhibiting agent include U-62066 (shown below) and U-62066 analogs.

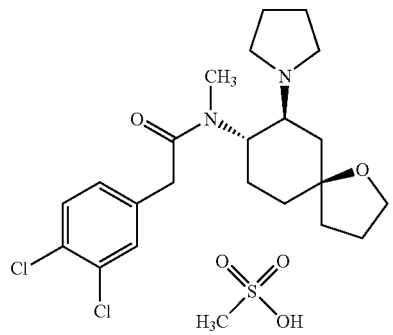

Embodiments of the inhibiting agent include ruthenium red, [(NH₃)₅RuORu(NH₃)₄ORu(NH₃)₅]Cl₆, and ruthenium red analogs. However, such compounds generally have non-specific activity and so may not be suitable for development as drugs.

Embodiments of the inhibiting agent include 4-(2-aminoethyl)benzenesulfonyl fluoride hydrochloride,

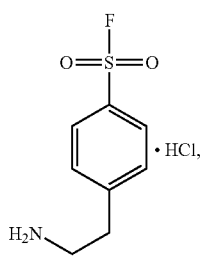

and 4-(2-aminoethyl)benzenesulfonyl fluoride hydrochloride analogs. 4-(2-aminoethyl)benzenesulfonyl fluoride hydrochloride is an irreversible serine protease inhibitor and may be a covalent modifier of protein or DNA and so may not be suitable for development as an anti-viral drug.

Embodiments of the inhibiting agent include thiothixene,

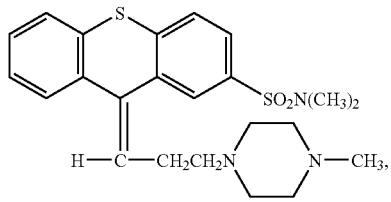

and thiothixene analogs.

Embodiments of the inhibiting agent include (±)-3-amino-1-hydroxy-2-pyrrolidone and (±)-3-amino-1-hydroxy-2-pyrrolidone analogs.

Embodiments of the inhibiting agent include S(−)-3PPP hydrochloride (Preclamol hydrochloride, marketed by Astra) and S(−)-3PPP hydrochloride (Preclamol hydrochloride) analogs.

Embodiments of the inhibiting agent include spiradoline, spiradoline analogs, and compounds having a spiradoline scaffold. The structure of the spiradoline scaffold is shown on the left and the structure of spiradoline is shown on the right.

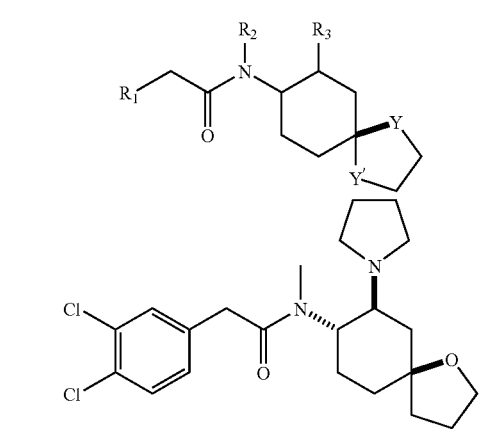

Spiradoline (U-62066)

In the spiradoline scaffold shown above, Y and Y' are independently selected from the group consisting of: —CH₂— and —O—. In an embodiment, Y is —O— and Y' is —CH₂—.

R₁ is aryl, where in an embodiment the aryl group are independently selected from the aryl groups described in the preferred embodiments described in this section. In a preferred embodiment, R₁ is

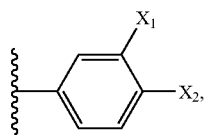

where $X_1$ and $X_2$ are each independently selected from the group consisting of: —CH₃, —F, —Cl, and —OCH₃. In an embodiment, $X_1$ and $X_2$ are each —Cl.

R₂ is selected from the group consisting of: —H and -alkyl, where in an embodiment the alkyl group is independently selected from the alkyl groups described in the preferred embodiments described in this section. In an embodiment, $R_2$ is —$CH_3$.

$R_3$ is selected from the group consisting of

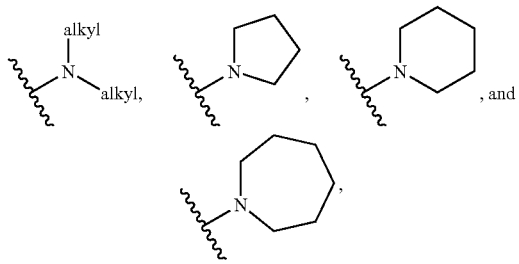

where in an embodiment the alkyl group and the aryl are independently selected from the alkyl groups and the aryl groups described in the preferred embodiments described in this section. In an embodiment, $R_3$ is:

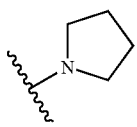

In an embodiment, the structure of the spiradoline scaffold is shown below:

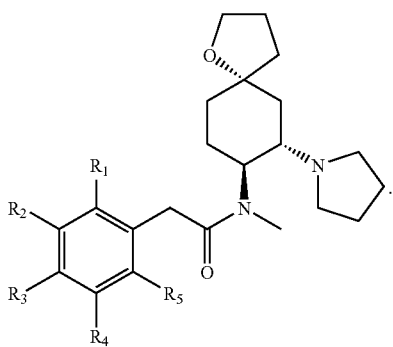

In the spiradoline scaffold shown above, $R_1$-$R_5$ are independently selected from the group consisting of: H, $CH_3$, Cl, F, and $OCH_3$.

Pharmaceutical Formulations and Routes of Administration

Embodiments of the present disclosure include one or more inhibiting agents identified herein and formulated with one or more pharmaceutically acceptable excipients, diluents, carriers and/or adjuvants. In addition, embodiments of the present invention include such inhibiting agents formulated with one or more pharmaceutically acceptable auxiliary substances. In particular, one or more inhibiting agents can be formulated with one or more pharmaceutically acceptable excipients, diluents, carriers, and/or adjuvants to provide an embodiment of a composition of the invention.

In an embodiment, an inhibiting agent that inhibits binding of an NS4B polypeptide to the 3'UTR of HCV negative strand RNA (referred generically below as an "a subject active agent" or "drug") can be formulated with one or more pharmaceutically acceptable excipients.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the invention, the inhibiting agent is administered to the host using a convenient means capable of resulting in the desired effect (e.g., reduction in viral load, reduction in liver fibrosis, increase in liver function, and the like). Thus, embodiments of the present invention provide an inhibiting agent incorporated into a variety of formulations for therapeutic administration. For example, embodiments of the present invention provide the inhibiting agent formulated into pharmaceutical compositions by combination with appropriate, pharmaceutically acceptable carriers or diluents, and formulated into preparations in solid, semi-solid, liquid or gaseous forms, such as tablets, capsules, powders, granules, ointments, solutions, suppositories, injections, inhalants and aerosols.

In pharmaceutical dosage forms of embodiments of the invention, the inhibiting agent may be present in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, the inhibiting agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the inhibiting agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the inhibiting agent can be utilized in aerosol formulation to be administered via inhalation. Embodiments of the inhibiting agent agent can be formulated into pressurized acceptable propellants such as dichlorodifluoromethane, propane, nitrogen and the like.

Furthermore, embodiments of the inhibiting agent can be made into suppositories by mixing with a variety of bases such as emulsifying bases or water-soluble bases. Embodiments of the inhibiting agent can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more inhibiting agents. Similarly, unit dosage forms for injection or intravenous administration may comprise the inhibiting agent in a composition as a solution in sterile water, normal saline or another pharmaceutically acceptable carrier.

Embodiments of the inhibiting agent can be formulated in an injectable composition in accordance with the invention. Typically, injectable compositions are prepared as liquid solutions or suspensions; solid forms suitable for solution in, or suspension in, liquid vehicles prior to injection may also be prepared. The preparation may also be emulsified or the active ingredient (inhibiting agent) encapsulated in liposome vehicles.

In an embodiment, the inhibiting agent is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the inhibiting agent can be accomplished using any of a variety of refillable, pump systems. Pumps provide consistent, controlled release over time. In some embodiments, the inhibiting agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the inhibiting agent are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the inhibiting agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Compositions of the present disclosure may be used with a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho) esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Exemplary biodegradable matrices include a polylactide matrix, a polyglycolide matrix, and a polylactide co-glycolide (co-polymers of lactic acid and glycolic acid) matrix.

In another embodiment, the pharmaceutical composition of the present invention (as well as combination compositions) is provided in a controlled release system. For example, the inhibiting agent may be administered using intravenous infusion, an implantable osmotic pump, a transdermal patch, liposomes, or other modes of administration. In one embodiment, a pump may be used (Sefton (1987). CRC Crit. Ref Biomed. Eng. 14:201; Buchwald et al. (1980). Surgery 88:507; Saudek et al. (1989). N. Engl. J. Med. 321:574). In another embodiment, polymeric materials are used. In yet another embodiment a controlled release system is placed in proximity of the therapeutic target, i.e., the brain, thus requiring only a fraction of the systemic dose. Other controlled release systems are discussed in the review by Langer (1990). Science 249:1527-1533.

In another embodiment, the compositions of the present disclosure (as well as combination compositions, whether administered as separate unit dose forms or together in a single dose form) may be impregnated into absorptive materials, such as sutures, bandages, and gauze, or coated onto the surface of solid phase materials. Other delivery systems of this type will be readily apparent to those skilled in the art.

Treatment Methods

Embodiments of the present disclosure include methods of treating an infection with a virus from the Flaviviridae family. In particular, inhibiting agents described herein or identified using the screening method of the invention can be used to treat an infection by a Flaviviridae family virus. In an embodiment, inhibiting agents can be combined with other anti-viral agents to treat a Flaviviridae family viral infection. Embodiments of the method involve administering to an individual in need thereof one or more inhibiting agents that inhibit binding of an NS4B polypeptide to the 3'UTR of HCV negative strand RNA. In an embodiment, the present invention provides methods of treating a flavivirus infection, e.g., an HCV infection, and methods of reducing liver fibrosis that may occur as sequalae of an HCV infection.

In an embodiment, the inhibiting agent can include one or more of inhibiting agents described above. In an embodiment, the inhibiting agent is clemizole hydrochloride (1-p-chlorobenzyl-2-(1-pyrrolidinyl)methylbenzimidazole hydrochloride), analog, or a derivative (analog) thereof. Additional details regarding clemizole and dosing of clemizole is described above.

In an embodiment, an effective amount of the inhibiting agent is an amount that, when administered in one or more doses to a host (e.g., human) in need thereof, reduces HCV viral load in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the viral load in the individual not treated with the inhibiting agent.

Viral load can be measured by measuring the titer or level of virus in serum. These methods include, but are not limited to, a quantitative polymerase chain reaction (PCR) and a branched DNA (bDNA) test. Quantitative assays for measuring the viral load (titer) of HCV RNA have been developed. Many such assays are available commercially, including a quantitative reverse transcription PCR(RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) Ann. Intern. Med. 123:321-329. Also of interest is a nucleic acid test (NAT) sold by Chiron Corporation under the trade name Procleix®, which NAT simultaneously tests for the presence of HIV-1 and HCV. See, e.g., Vargo et al. (2002) Transfusion 42:876-885.

In some embodiments, an effective amount of the inhibiting agent is an amount that, when administered in one or more doses to a host (e.g., human) in need thereof, increases liver function in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the liver function in the individual not treated with the inhibiting agent.

In some embodiments, an effective amount of the inhibiting agent is an amount that, when administered in one or more doses to a host (e.g., a human) in need thereof, reduces liver fibrosis in the host by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the degree of liver fibrosis in the individual not treated with the inhibiting agent.

Liver fibrosis reduction is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of a subject therapy can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

Embodiments of the present disclosure provide methods, inhibiting agents, and pharmaceutical formulations useful in the treatment of patients suffering from a viral infection. In one embodiment, the patient is infected with HCV but is not known to be infected with any other virus, including, but not limited to, HIV. In another embodiment, the patient is infected with HCV and one or more additional viruses, including, but not limited to, HIV. In one embodiment, the patient is treated for a viral infection by administering only a single inhibiting agent as described herein as useful in the treatment of HCV infection. In another embodiment, the patient is treated for a viral infection by administering both an inhibiting agent described herein as useful in the treatment of HCV infection as well as one or more additional agents known to be useful in the treatment of viral infection. In one embodiment, the one or more additional agents does not include a CCR-5 antagonist. In another embodiment, the one or more additional agents does include a CCR-5 antagonist, and the patient is infected with HCV but not known to be infected (or is not infected) with HIV.

Dosages

Embodiments of the inhibiting agent can be administered to a host in one or more doses. In an embodiment, the inhibiting agent can be administered in an amount of about 10 mg to 1000 mg per dose, e.g., about 10 mg to 20 mg, about 20 mg to 25 mg, about 25 mg to 50 mg, about 50 mg to 75 mg, about 75 mg to 100 mg, about 100 mg to 125 mg, about 125 mg to 150 mg, about 150 mg to 175 mg, about 175 mg to 200 mg, about 200 mg to 225 mg, about 225 mg to 250 mg, about 250 mg to 300 mg, about 300 mg to 350 mg, about 350 mg to 400 mg, about 400 mg to 450 mg, about 450 mg to 500 mg, about 500 mg to 750 mg, or about 750 mg to 1000 mg per dose.

In an embodiment, the amount of the inhibiting agent per dose is determined on a per body weight basis. For example, in an embodiment, the inhibiting agent can be administered in an amount of about 0.5 mg/kg to 100 mg/kg, e.g., about 0.5 mg/kg to 1 mg/kg, about 1 mg/kg to 2 mg/kg, about 2 mg/kg to 3 mg/kg, about 3 mg/kg to 5 mg/kg, about 5 mg/kg to 7 mg/kg, about 7 mg/kg to about 10 mg/kg, about 10 mg/kg to 15 mg/kg, about 15 mg/kg to 20 mg/kg, about 20 mg/kg to 25 mg/kg, about 25 mg/kg to 30 mg/kg, about 30 mg/kg to 40 mg/kg, about 40 mg/kg to 50 mg/kg per dose, about 50 mg/kg to 60 mg/kg, about 60 mg/kg to 70 mg/kg, about 70 mg/kg to 80 mg/kg, about 80 mg/kg to 90 mg/kg, or about 90 mg/kg to 100 mg/kg, or more than about 100 mg/kg.

Additional details regarding clemizole dosing are described above.

Those of skill will readily appreciate that dose levels can vary as a function of the specific inhibiting agent, the severity of the symptoms and the susceptibility of the subject to side effects. Preferred dosages for a given compound are readily determinable by those of skill in the art by a variety of means.

In an embodiment, multiple doses of the inhibiting agent are administered. The frequency of administration of the inhibiting agent can vary depending on any of a variety of factors, e.g., severity of the symptoms, and the like. For example, in an embodiment, the inhibiting agent is administered at least once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the inhibiting agent is administered continuously.

The duration of administration of the inhibiting agent, e.g., the period of time over which the inhibiting agent is administered, can vary, depending on any of a variety of factors, e.g., patient response, etc. For example, the inhibiting agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present invention provide methods for treating a viral infection comprising the administration of the inhibiting agent to a host (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent can be administered in a single dose or in multiple doses. Many of the inhibiting agents described herein are suitable for oral administration, which may be preferable for most patients.

Embodiments of the inhibiting agent can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the inhibiting agent. Where systemic delivery is desired, administration typically involves invasive or systemically absorbed topical or mucosal administration of pharmaceutical preparations.

The inhibiting agent can also be delivered to the subject by enteral administration. Enteral routes of administration include, but are not limited to, oral and rectal (e.g., using a suppository) delivery.

Methods of administration of the inhibiting agent through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

Combination Therapies

Embodiments of the present invention include methods, inhibiting agents, and pharmaceutical formulations for the treatment of viral infection. Embodiments of the inhibiting agents and pharmaceutical formulations useful in the methods of the present disclosure can be employed in combination with other anti-viral agents to treat viral infection. In an embodiment, in accordance with the methods of the present invention, an inhibiting agent that is used to treat a host infected by a Flaviviridae family viral infection is used in combination with one or more other anti-HCV agents to treat HCV infection. In an embodiment, in accordance with the methods of the present invention, an inhibiting agent that prevents the binding of NS4B to the 3'-UTR of HCV RNA (also referred to herein as an "HCV NS4B antagonist") can be used in combination with one or more other anti-HCV agents to treat HCV infection.

Current medical practice to treat HCV infection typically employs either interferon-alpha monotherapy or combination therapy with ribavirin (such as Rebetol or Copegus) and either an interferon-alpha (such as interferon alpha 2b) or pegylated interferon (such as Pegasys, marketed by Roche, or PEG-Intron, marketed by Schering Plough). In accordance with the methods of the present disclosure, an inhibiting can be used in combination with these standard therapies to treat HCV infection.

A number of HCV protease inhibitors are in development for the treatment of HCV infection, and in accordance with the methods of the present disclosure, co-administration of an inhibiting agent that prevents the binding of NS4B to the 3'-UTR of HCV RNA and an HCV protease inhibitor can be efficacious in the treatment of HCV. In one embodiment, an interferon alpha and/or a nucleoside analog such as ribavirin is/are also employed in this combination therapy. Suitable HCV protease inhibitors include, but are not limited to, telaprevir (VX-950, Vertex), BILN 2061 and BI12202 (Boehringer Ingelheim), boceprevir (SCH 503034, Schering Plough), ITMN191 (Roche/InterMune/Array BioPharma), MK-7009 (Merck), TMC435350 (Tibotec/Medivir), ACH-1095 and ACH-806 (Achillion/Gilead), and other inhibitors of NS3/NS4A protease, including, but not limited to, compounds in development by Presidio.

A number of HCV RNA polymerase (NS5B) inhibitors are in development for the treatment of HCV infection, and in accordance with the methods of the present disclosure, co-administration of an inhibiting agent that prevents the binding of NS4B to the 3'-UTR of HCV RNA and an HCV RNA polymerase inhibitor can be efficacious in the treatment of HCV. In one embodiment, an interferon alpha and/or a nucleoside analog such as ribavirin and/or an HCV protease inhibitor is/are also employed in this combination therapy. Suitable HCV RNA polymerase inhibitors include, but are not limited to, valopicitabine (NM283, Idenix/Novartis), HCV-796 (Wyeth/ViroPharma), R1626 (Roche), R7128 (Roche/Pharmasset), GS-9190 (Gilead), MK-0608 (Merck), PSI-6130 (Pharmasset), and PFE-868,554 (PFE).

A number of toll-like receptor (TLR) agonists are in development for the treatment of HCV infection, and in accordance with the methods of the present disclosure, co-administration of an NS4B antagonist that prevents the binding of NS4B to the 3'-UTR of HCV RNA and a TLR agonist can be efficacious in the treatment of HCV. In one embodiment, an interferon alpha and/or a nucleoside analog such as ribavirin and/or an HCV protease inhibitor and/or an HCV RNA polymerase inhibitor is/are also employed in this combination therapy. Suitable TLR agonists include, but are not limited to, TLR7 agonists (i.e., ANA245 and ANA975 (Anadys/Novartis)) and TLR9 agonists (i.e., Actilon (Coley) and IMO-2125 (Idera)).

A number of thiazolide derivatives are in development for the treatment of HCV infection, and in accordance with the methods of the present disclosure, co-administration of an NS4B antagonist that prevents the binding of NS4B to the 3'-UTR of HCV RNA and a thiazolide, including, but not limited to, Nitazoxanide (Alinia, or other sustained release formulations of nitazoxanide or other thiazolides, Romark Laboratories) can be efficacious in the treatment of HCV. In an embodiment, an interferon alpha and/or a nucleoside analog such as ribavirin and/or an HCV protease inhibitor and/or an HCV RNA polymerase inhibitor and/or a TLR agonist is/are also employed in this combination therapy.

In another embodiment of the methods of the present disclosure, co-administration of an inhibiting agent that prevents the binding of NS4B to the 3'-UTR of HCV RNA and a cyclophilin inhibitor (i.e., NIM-811 (Novartis) and DEBIO-025 (Debiopharm)) and/or an alpha-glucosidase inhibitor (i.e., Celgosivir (Migenix)) and/or one or more agents from one or more of the other classes of HCV therapeutic agents discussed herein is used to treat HCV infection. Moreover, there are several targets within NS4B, and compounds that interact with these other targets can, in accordance with the methods of the present disclosure, be used in combination with an NS4B antagonist that prevents the binding of NS4B to the 3'-UTR of HCV RNA and, optionally, one or more of the other classes of inhibiting agents mentioned herein, to treat HCV infection. Such additional NS4B targets include: the N-terminal amphipathic helix (see PCT publication WO 2002/089731, incorporated herein by reference), the NS4B GTPase (see PCT publication WO 2005/032329, incorporated herein by reference), the second amphipathic helix, the PIP2 binding activity of the first amphipathic helix in NS4B (see U.S. provisional patent application Ser. No. 60/057,188, incorporated herein by reference).

Other agents that can be used in combination with inhibiting agents of the present disclosure that prevent the binding of NS4B to the 3'-UTR of HCV RNA include (i) agents targeting NS5A, including, but not limited to, A-831 (Arrow Therapeutics), AZD2836 (Astra Zeneca), and agents in development by XTL/Presidio or BMS (see PCT publications WO 2006/133326 and WO 2008/021928, incorporated herein by reference); (ii) agents targeting TBC1D20 and/or NS5A's interaction with TBC1D20 (see PCT publication WO 2007/018692 and U.S. patent application Ser. No. 11/844,993, incorporated herein by reference), (iii) agents targeting NS4B's GTPase activity (see PCT publication WO 2005/032329 and US patent application publication 2006/

0199174, incorporated herein by reference); (iv) agents inhibiting membrane association mediated by the HCV amphipathic helices, such as those found in NS5A, NS4B, and NS5B (see PCT publication WO 2002/089731, supra); (v) agents targeting PIP2 or BAAPP domains in HCV proteins, such as those found in NS4B and NS5A (see U.S. provisional patent application 60/057,188, supra); (vi) agents targeting HCV entry, assembly, or release, including antibodies to co-receptors; (vii) agents targeting HCV NS3 helicase; (viii) siRNAs, shRNAs, antisense RNAs, or other RNA-based molecules targeting sequences in HCV; (ix) agents targeting microRNA122 or other microRNAs modulating HCV replication; (x) agents targeting PD-1, PD-L1, or PD-L2 interactions or pathway (see US patent application publications 20080118511, 20070065427, 20070122378, incorporated herein by reference); and (xi) agents targeting HCV amphipathic helix function, such as AH2 inhibitors.

In another embodiment of the present disclosure, an inhibiting agent that prevents the binding of NS4B to the 3'-UTR of HCV RNA is used in combination with one or more drugs capable of treating an HIV infection to treat a patient that is co-infected with HIV and HCV. In another embodiment of the present disclosure, an inhibiting agent that prevents the binding of NS4B to the 3'-UTR of HCV RNA is used in combination with one or more drugs capable of treating an HBV infection to treat a patient that is co-infected with HBV and HCV. In an embodiment, an inhibiting agent that prevents the binding of NS4B to the 3'-UTR of HCV RNA is used in combination with a PD-L1 inhibitor to treat a viral infection.

As mentioned above, embodiments of the present include the administration of an inhibiting agent identified herein (or by using an embodiment of the screen of the invention) in conjunction with at least one additional therapeutic agent to treat a viral infection. Suitable additional therapeutic agents include, but are not limited to, ribavirin; a nucleoside analog (e.g., levovirin, viramidine, etc.); an NS3 inhibitor; an NS5 inhibitor; an interferon; and a side effect management agent.

In an embodiment, the at least one additional suitable therapeutic agent includes ribavirin. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. The disclosure also contemplates use of derivatives of ribavirin (see, e.g., U.S. Pat. No. 6,277,830).

In an embodiment, the at least one additional suitable therapeutic agent includes levovirin. Levovirin is the L-enantiomer of ribavirin, and exhibits the property of enhancing a Th1 immune response over a Th2 immune response. Levovirin is manufactured by ICN Pharmaceuticals.

In an embodiment, the at least one additional suitable therapeutic agent includes viramidine. Viramidine is a 3-carboxamidine derivative of ribavirin, and acts as a prodrug of ribavirin. It is efficiently converted to ribavirin by adenosine deaminases.

Nucleoside analogs that are suitable for use in a combination therapy include, but are not limited to, ribavirin, levovirin, viramidine, isatoribine, an L-ribofuranosyl nucleoside as disclosed in U.S. Pat. No. 5,559,101 and encompassed by Formula I of U.S. Pat. No. 5,559,101 (e.g., 1-β-L-ribofuranosyluracil, 1-β-L-ribofuranosyl-5-fluorouracil, 1-β-L-ribofuranosylcytosine, 9-β-L-ribofuranosyladenine, 9-β-L-ribofuranosylhypoxanthine, 9-β-L-ribofuranosylguanine, 9-β-L-ribofuranosyl-6-thioguanine, 2-amino-α-L-ribofuranl[1',2':4,5]oxazoline, O2,O2-anhydro-1-α-L-ribofuranosyluracil, 1-α-L-ribofuranosyluracil, 1-(2,3,5-tri-O-benzoyl-α-ribofuranosyl)-4-thiouracil, 1-α-L-ribofuranosylcytosine, 1-α-L-ribofuranosyl-4-thiouracil, 1-α-L-ribofuranosyl-5-fluorouracil, 2-amino-β-L-arabinofurano[1',2':4,5]oxazoline, O2,O2-anhydro-β-L-arabinofuranosyluracil, 2'-deoxy-β-L-uridine, 3'5'-Di-O-benzoyl-2'deoxy-4-thio β-L-uridine, 2'-deoxy-β-L-cytidine, 2'-deoxy-β-L-4-thiouridine, 2'-deoxy-β-L-thymidine, 2'-deoxy-β-L-5-fluorouridine, 2',3'-dideoxy-β-L-uridine, 2'-deoxy-(3-L-5-fluorouridine, and 2'-deoxy-β-L-inosine); a compound as disclosed in U.S. Pat. No. 6,423,695 and encompassed by Formula I of U.S. Pat. No. 6,423,695; a compound as disclosed in U.S. Patent Publication No. 2002/0058635, and encompassed by Formula 1 of U.S. Patent Publication No. 2002/0058635; a nucleoside analog as disclosed in WO 01/90121 A2 (Idenix); a nucleoside analog as disclosed in WO 02/069903 A2 (Biocryst Pharmaceuticals Inc.); a nucleoside analog as disclosed in WO 02/057287 A2 or WO 02/057425 A2 (both Merck/Isis); and the like.

In an embodiment, the at least one additional suitable therapeutic agent can include HCV NS3 inhibitors. Suitable HCV non-structural protein-3 (NS3) inhibitors include, but are not limited to, a tri-peptide as disclosed in U.S. Pat. Nos. 6,642,204, 6,534,523, 6,420,380, 6,410,531, 6,329,417, 6,329,379, and 6,323,180 (Boehringer-Ingelheim); a compound as disclosed in U.S. Pat. No. 6,143,715 (Boehringer-Ingelheim); a macrocyclic compound as disclosed in U.S. Pat. No. 6,608,027 (Boehringer-Ingelheim); an NS3 inhibitor as disclosed in U.S. Pat. Nos. 6,617,309, 6,608,067, and 6,265,380 (Vertex Pharmaceuticals); an azapeptide compound as disclosed in U.S. Pat. No. 6,624,290 (Schering); a compound as disclosed in U.S. Pat. No. 5,990,276 (Schering); a compound as disclosed in Pause et al. (2003) J. Biol. Chem. 278:20374-20380; NS3 inhibitor BILN 2061 (Boehringer-Ingelheim; Lamarre et al. (2002) Hepatology 36:301A; and Lamarre et al. (Oct. 26, 2003) Nature doi: 10.1038/nature02099); NS3 inhibitor VX-950 (Vertex Pharmaceuticals; Kwong et al. (Oct. 24-28, 2003) 54th Ann. Meeting AASLD); NS3 inhibitor SCH$_6$ (Abib et al. (Oct. 24-28, 2003) Abstract 137. Program and Abstracts of the 54th Annual Meeting of the American Association for the Study of Liver Diseases (AASLD). Oct. 24-28, 2003. Boston, Mass.); any of the NS3 protease inhibitors disclosed in WO 99/07733, WO 99/07734, WO 00/09558, WO 00/09543, WO 00/59929 or WO 02/060926 (e.g., compounds 2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224-226 in WO 02/060926); an NS3 protease inhibitor as disclosed in any one of U.S. Patent Publication Nos. 2003019067, 20030187018, and 20030186895; and the like.

In an embodiment, the NS3 inhibitor used in a combination therapy of the invention is a member of the class of specific NS3 inhibitors, e.g., NS3 inhibitors that inhibit NS3 serine protease activity and that do not show significant inhibitory activity against other serine proteases such as human leukocyte elastase, porcine pancreatic elastase, or bovine pancreatic chymotrypsin, or cysteine proteases such as human liver cathepsin B.

In an embodiment, the at least one additional suitable therapeutic agent includes NS5B inhibitors. Suitable HCV non-structural protein-5 (NS5; RNA-dependent RNA polymerase) inhibitors include, but are not limited to, a compound as disclosed in U.S. Pat. No. 6,479,508 (Boehringer-Ingelheim); a compound as disclosed in any of International Patent Application Nos. PCT/CA02/01127, PCT/CA02/01128, and PCT/CA02/01129, all filed on Jul. 18, 2002 by Boehringer Ingelheim; a compound as disclosed in U.S. Pat. No. 6,440,985 (ViroPharma); a compound as disclosed in WO 01/47883, e.g., JTK-003 (Japan Tobacco); a dinucleotide analog as disclosed in Zhong et al. (2003) Antimicrob. Agents Chemother. 47:2674-2681; a benzothiadiazine compound as disclosed in Dhanak et al. (2002) J. Biol. Chem. 277(41): 38322-7; an NS5B inhibitor as disclosed in WO 02/100846 A1 or WO 02/100851 A2 (both Shire); an NS5B inhibitor as disclosed in WO 01/85172 A1 or WO 02/098424 A1 (both Glaxo SmithKline); an NS5B inhibitor as disclosed in WO 00/06529 or WO 02/06246 A1 (both Merck); an NS5B inhibitor as disclosed in WO 03/000254 (Japan Tobacco); an NS5B inhibitor as disclosed in EP 1 256,628 A2 (Agouron); JTK-002 (Japan Tobacco); JTK-109 (Japan Tobacco); and the like.

In an embodiment, the NS5 inhibitor used in the combination therapies of the invention is a member of the class of specific NS5 inhibitors, e.g., NS5 inhibitors that inhibit NS5 RNA-dependent RNA polymerase and that lack significant inhibitory effects toward other RNA dependent RNA polymerases and toward DNA dependent RNA polymerases.

In an embodiment, the at least one additional therapeutic agent is an interferon, e.g., interferon-alpha (IFN-α). Any known IFN-α can be used in the treatment methods of the invention. The term "interferon-alpha" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α; essentially any IFN-α that has antiviral properties, as described for naturally occurring IFN-α.

Suitable alpha interferons include, but are not limited to, naturally-occurring IFN-α (including, but not limited to, naturally occurring IFN-α2a, IFN-α2b); recombinant interferon alpha-2b such as Intron-A interferon available from Schering Corporation, Kenilworth, N.J.; recombinant interferon alpha-2a such as Roferon interferon available from Hoffmann-La Roche, Nutley, N.J.; recombinant interferon alpha-2C such as Berofor alpha 2 interferon available from Boehringer Ingelheim Pharmaceutical, Inc., Ridgefield, Conn.; interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain; and interferon alpha-n3 a mixture of natural alpha interferons made by Interferon Sciences and available from the Purdue Frederick Co., Norwalk, Conn., under the Alferon tradename.

The term "IFN-α" also encompasses consensus IFN-α. Consensus IFN-α (also referred to as "CIFN" and "IFN-con" and "consensus interferon") encompasses, but is not limited to, the amino acid sequences designated IFN-con1, IFN-con2 and IFN-con3 which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-con1 is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods. In an embodiment, the at least one additional therapeutic agent is CIFN.

In an embodiment, fusion polypeptides comprising an IFN-α and a heterologous polypeptide can also be used in the combination therapies of the invention. Suitable IFN-α fusion polypeptides include, but are not limited to, Albuferon-alpha™ (a fusion product of human albumin and IFN-α; Human Genome Sciences; see, e.g., Osborn et al. (2002) J. Pharmacol. Exp. Therap. 303:540-548). Also suitable for use in the present disclosure are gene-shuffled forms of IFN-α. See, e.g., Masci et al. (2003) Curr. Oncol. Rep. 5:108-113. Other suitable interferons include Multiferon (Viragen), Medusa Interferon (Flamel Technology), Locteron (Octopus), and Omega Interferon (Intarcia/Boehringer Ingelheim).

The term "IFN-α" also encompasses derivatives of IFN-α that are derivatized (e.g., are chemically modified relative to the naturally occurring peptide) to alter certain properties such as serum half-life. As such, the term "IFN-α" includes glycosylated IFN-α; IFN-α derivatized with polyethylene glycol ("PEGylated IFN-α"); and the like. PEGylated IFN-α, and methods for making same, is discussed in, e.g., U.S. Pat. Nos. 5,382,657; 5,981,709; and 5,951,974. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.).

In an embodiment, the IFN-α polypeptides can be modified with one or more polyethylene glycol moieties, i.e., PEGylated. The PEG molecule of a PEGylated IFN-α polypeptide is conjugated to one or more amino acid side chains of the IFN-α polypeptide. In an embodiment, the PEGylated IFN-α contains a PEG moiety on only one amino acid. In another embodiment, the PEGylated IFN-α contains a PEG moiety on two or more amino acids, e.g., the IFN-α contains a PEG moiety attached to two, three, four, five, six, seven, eight, nine, or ten different amino acid residues. IFN-α may be coupled directly to PEG (i.e., without a linking group) through an amino group, a sulfhydryl group, a hydroxyl group, or a carboxyl group.

To determine the optimum combination of an inhibiting agent, such as clemizole, with other anti-HCV agents, HCV replication assays and/or animal studies can be performed in the presence of various combinations of the various anti-HCV agents. Increased inhibition of replication in the presence of an additional agent (above that observed with monotherapy) is evidence for the potential benefit of the combination therapy.

Figure 1B:
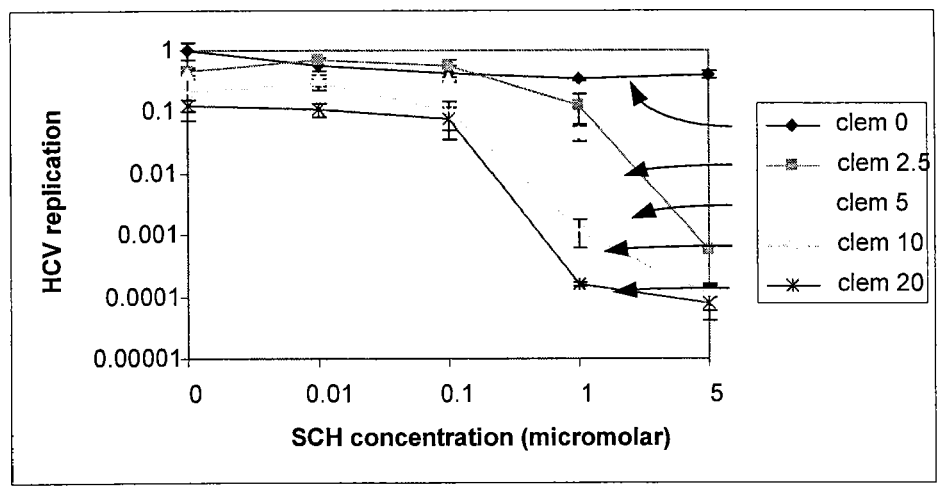

For example, HCV replication assays employing a luciferase reporter-linked HCV genome in the presence of various combinations of clemizole and an NS3 protease inhibitor (SCH503034) are shown in FIGS. 1A and 1B. In such assays, luciferase activity is directly proportional to HCV RNA genome replication. In this method, Huh 7.5 cells were electroporated with a wild-type luciferase reporter-linked HCV genome, and plated replicates were cultured in the presence of the indicated concentrations of clemizole and SCH503034 (SCH) for 72 hours, followed by lysis and determination of luciferase activity, essentially as described (Nature Biotechnology 26, 1019-1027 (2008), which is included herein in its entirety by reference). The results can be plotted on a linear or log scale as a function of drug concentrations to generate replication inhibition curves. The inhibition curve for the NS3 inhibitor shows significantly more inhibition in the presence of increasing concentrations of clemizole. In particular, at low micromolar concentrations of SCH503034 (such as 1-5 micromolar), addition of clemizole can increase the inhibition of HCV replication in a dose-dependent manner by up to several logs. Similarly increased efficacy of combination therapy (over monotherapy) is expected in accordance with the methods of the invention when an NS4B antagonist is co-administered with other NS3 protease inhibitors, and with other anti-HCV agents that have a mechanism of action distinct from NS4B antagonists that have the same mechanism of action as clemizole. These results not only provide clear evidence for the benefit of combination therapy of clemizole and SCH503034, but also demonstrate that improved efficacy and likely decreased resistance can be expected following in vivo therapy with this and similar combination therapies provided by the present disclosure. Moreover, these results demonstrate that one skilled in the art can readily perform assays to determine optimal combination therapies with the NS4B antagonists useful in embodiments of the methods of the present invention and other anti-HCV agents in view of the disclosure herein.

In an embodiment, side effect management agents can be used in the treatment methods of the invention, and these include agents that are effective in pain management; agents that ameliorate gastrointestinal discomfort; analgesics, anti-inflammatories, antipsychotics, antineurotics, anxiolytics, and hematopoietic agents. In addition, embodiments of the invention contemplate the use of any compound for palliative care of patients suffering from pain or any other side effect in the course of treatment with a subject therapy. Exemplary palliative agents include acetaminophen, ibuprofen, other NSAIDs, H2 blockers, and antacids.

Hosts Suitable for Treatment

Hosts suitable for treatment with an embodiment of the inhibiting agent or an embodiment of the method include hosts who are infected with a flavirivirus. As used herein, the term "flavivirus" includes any member of the family Flaviviridae, including, but not limited to, Dengue virus, including Dengue virus 1, Dengue virus 2, Dengue virus 3, Dengue virus 4 (see, e.g., GenBank Accession Nos. M23027, M19197, A34774, and M14931); Yellow Fever Virus; West Nile Virus; Japanese Encephalitis Virus; St. Louis Encephalitis Virus; Bovine Viral Diarrhea Virus (BVDV); and Hepatitis C Virus (HCV); and any serotype, strain, genotype, subtype, quasispecies, or isolate of any of the foregoing. Where the flavivirus is HCV, the HCV is any of a number of genotypes, subtypes, or quasispecies, including, e.g., genotype 1, including 1a and 1b, 2, 3, 4, 6, etc. and subtypes (e.g., 2a, 2b, 3a, 4a, 4c, etc.), and quasispecies.

Hosts suitable for treatment with embodiments of the present invention include treatment failure patients. The term "treatment failure patients" (or "treatment failures") as used herein generally refers to HCV-infected patients who failed to respond to previous therapy for HCV (referred to as "non-responders") or who initially responded to previous therapy, but in whom the therapeutic response was not maintained (referred to as "relapsers"). The previous therapy generally can include treatment with any anti-viral agent other than an inhibiting agent of the present disclosure.

Hosts suitable for treatment with embodiments of the present disclosure include individuals who have been clinically diagnosed as infected with HCV. Individuals who are infected with HCV can be identified by detecting HCV RNA in their blood, and/or having an anti-HCV antibody in their serum.

Individuals who are clinically diagnosed as infected with HCV include naïve individuals (e.g., individuals not previously treated for HCV).

Hosts suitable for treatment with embodiments of the present disclosure include individuals who have an HCV titer of at least about 105, at least about 5×105, or at least about 106, genome copies of HCV per milliliter of serum. The patient may be infected with any HCV genotype (genotype 1, including 1a and 1b, 2, 3, 4, 6, etc. and subtypes (e.g., 2a, 2b, 3a, etc.)), particularly a difficult to treat genotype such as HCV genotype 1 and particular HCV subtypes and quasispecies.

Also suitable for treatment are HCV-positive hosts (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment, or who have a contraindication to therapy with a known anti-viral agent.

In an embodiment, HCV-positive hosts with stage 3 or 4 liver fibrosis according to the METAVIR scoring system are suitable for treatment with the methods of the present disclosure. In another embodiment, hosts suitable for treatment with embodiments of the present disclosure are patients with decompensated cirrhosis with clinical manifestations, including patients with far-advanced liver cirrhosis, including those awaiting liver transplantation. In still another embodiment, hosts suitable for treatment with embodiments of the present disclosure include patients with milder degrees of fibrosis including those with early fibrosis (stages 1 and 2 in the METAVIR, Ludwig, and Scheuer scoring systems; or stages 1, 2, or 3 in the Ishak scoring system).

In an embodiment of the present disclosure, to help optimally select patients most likely to benefit from therapy, as well as to monitor efficacy of therapy—especially in the face of potential drug resistant mutant viruses—the use of appropriate diagnostic tests provided by the present invention can be of great benefit. For example, assessing the sensitivity of the specific virus found in a given patient to the contemplated therapy can help identify the best match between candidate patient and the corresponding appropriate therapy. In the case of clemizole, clemizole analogs, compounds having a clemizole scaffold, or other inhibiting agents identified herein, this can be done by isolating the NS4B sequence from a given patient's HCV isolate and determining the efficacy of the drug's inhibition of RNA binding by the patient's NS4B isoform. This is especially important, because there currently is no efficient way of studying the drug sensitivity of a given patient's virus, because patient-derived inoculums cannot be readily cultured. The value of using such diagnostic assays to guide therapy has been extensively validated in HIV.

Replication Assay Protocol

In an embodiment, the replication assay protocol can include the following stages. It should be noted that the following replication assay protocol is non-limiting, and presented as an illustrative embodiment of a replication assay protocol.

Stage 1: RNA Transcription

1) Linearize the FL-J6/JFH-5'C19Rluc2AUbi plasmid with XbaI at 37° C. for 2 hrs, and run on 1% agarose gel to check completeness of digestion.

2) Digest the 5' overhangs by treatment with mung bean nuclease at 30° C. for 30 min.

3) For linearization of the Bart79I-luc plasmid (similar to Bart79I plasmid as described in Elazar et al. J. Virol. 2003, 77(10):6055-61 except that the neomycinphosphotransferase gene has been replaced with the gene encoding firefly luciferase) use ScaI restriction endonuclease, then examine the linearized template DNA on a gel to confirm that cleavage is complete, follow this with proteinase k digestion.

4) Purify templates by digestion with proteinase K for 30 min, phenol-chloroform extraction, ethanol precipitation, and then resuspend at 1 μg/μl.

5) For the transcription reaction, use 1 μg of purified template by using the T7 Megascript kit for FL-J6/JFH- 5'C19Rluc2AUbi (Ambion, Austin, Tex.) or the RiboMax™ kit for Bart79I-luc (Promega, Madison, Wis.). Incubate reactions at 37° C. for 4 h.

6) Add DNAse for 15 min.

7) Extract with an equal volume of phenol/chloroform and then with an equal volume of chloroform. Recover aqueous phase and transfer to new tube.

8) Precipitate the RNA by adding 1 volume of isopropanol and mixing well.

9) Chill the mixture for at least 15 min at −20° C. Centrifuge at 4° C. for 15 min at maximum speed to pellet the RNA.

10) Carefully remove the supernatant solution and resuspend the RNA in RNAse/DNase-free Water at 1 μg/μl.

11) Run on a gel and check RNA concentration.

12) Make aliquots and store in −80° C.

Stage 2: Electroporating Huh7.5 Cells

1) Wash cells once with PBS, trypsinize.

2) Resuspend cells in a total volume of 5 ml per 10 cm plate of complete medium (pull all together) in 50 ml tubes.

3) Pellet cells at 1000×RPM for 5 min at 4° C. Aspirate sup and resuspend in 10 ml ice cold RNAse free filtered 1×PBS (BioWhitaker)—pipette up and down ~5 times gently to get rid of cell clumps.

4) Pellet cells again at 1000×RPM as before and again resuspend in 10 ml ice cold PBS (BioWhitaker).

5) Remove a 10 μl aliquot to determine cell concentration.

6) Pellet cells again and resuspend in a final concentration of $1.5 \times 10^7$ cells/ml in ice cold RNAse free-PBS.

Need: $6 \times 10^6$ cells in 0.4 ml per each electroporation (ep) and 5 μg of FL-J6/JFH-5'C19Rluc2AUbi RNA or Bart79I-luc RNA 7) Place 5 μg RNA aliquot in an eppendorf tube (1 tube per ep)

8) Remove 0.4 ml of the cell suspension and add to the RNA. Mix twice by pipetting.

9) Immediately transfer 0.4 ml to a 2 mm gap ep cuvette

10) Pulse the cells: 820 v, 5 pulses, 99 μsec, 220 ms interval, unipolar.

11) Allow cells to rest for 15 min.

12) Transfer cells using the Pasteur pipette in the cuvette package to medium. Make a common stock from all tubes.

13) Plate 10,000 cells/well in 96 well plates.

14) Rotate plate a little for even cell plating.

15) Incubate for 24 hr before treatment.

Stage 3: Treating Plates

1) About 24 hr following electroporation prepare medium with the desired concentration of the drug.

2) Aspirate the medium and add 100 μl of fresh medium and drug. Leave untreated wells at the beginning and again at the end.

3) Repeat daily for 2 more days.

Stage 4: Harvesting (Day 5 from Electroporation)

1) Alamar blue assay— a) Include medium for background subtraction (and also for seeing change in color easily).

b) Aspirate medium.

c) Make a stock of medium plus 10% Alamar blue. Total volume per well is 100 μl.

d) Incubate for 2-2.5 hrs at 37° C. (or until there is a color change).

c) Read plates at flex station.

2) *Renilla* Luciferase assay— a) Aspirate medium with Alamar blue.

b) Wash with 1×PBS.

c) Aspirate completely (aspirate, then tilt and aspirate remainders of buffer again).

d) Make sure which lysis buffer is needed: firefly or *renilla*.

e) Add 30 μl of 1× lysis buffer (add 1 volume of 5× lysis buffer to 4 volumes of sterile water).

f) Shake the plate for 15 min.

g) Freeze at −80° C. At this point, one can stop or continue to the next phase.

Stage 5: Reading by Luminometer a) Thaw the plate.

b) Leave plate on ice until ready to read.

c) Prepare substrate reagent you need; for the *renilla*: thaw *renilla* buffer, make 1 volume 100× *Renilla* luc substrate plus 100 vol luc assay buffer+2 ml for priming luminometer. (e.g., for 4 ml *Renilla* lucsubstrate, add 40 ul assay buffer). For the firefly; thaw 10 ml firefly buffer and add to the luciferase reagent.

d) Read plates using a standard luminometer according to the manufacturer's directions.

EXAMPLES

The following examples are put forth so as to provide those of ordinary skill in the art with a complete disclosure and description of how to make and use the present disclosure, and are not intended to limit the scope of the disclosure nor are they intended to represent that the experiments below are all or the only experiments performed. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Over 150 million people are infected with Hepatitis C Virus (HCV) worldwide. Unfortunately, many of these individuals are unable to clear their infection with the current standard of care, which consists of a combination of interferon and ribavirin[1] (see the numbered list of references at the end of this example). Moreover, this treatment is associated with significant side effects, precluding its use by many individuals. Thus, current therapies are inadequate for the majority of the patients[1], and there is a pressing need for new HCV drugs[1].

The 9.6-kb positive single-stranded RNA HCV genome encodes a 3,000-amino-acid polyprotein which is proteolytically processed into structural proteins, which are components of the mature virus, and nonstructural proteins (NS), which are involved in replicating the viral genome[2]. Like other positive strand RNA viruses[3], HCV appears to replicate in association with intracellular membrane structures. In the case of HCV, the structures are termed the membranous web[4] and are believed to be induced by the NS4B protein. NS4B is also required to assemble the other viral NS proteins within the apparent sites of RNA replication[5]. It is not known how viral RNA, especially the negative strand template required for production of progeny genomes, might be incorporated or maintained at these replication sites.

NS4B and HCV RNA have been shown to colocalize to the membranous web[6,7] suggesting that NS4B is in intimate contact with viral RNA in the context of authentic viral RNA replication. The hepatitis A and polio picornaviruses have proteins termed 2C which are required for replication, bind RNA[8,9], and have an N-terminal amphipathic helix and a nucleotide binding motif[8-10]. NS4B contains the same structural features, and both of them are required for HCV replication[5,11]. The methods of the invention arose in part from the discoveries that NS4B similarly binds RNA that this interaction is critical for the HCV life cycle, and that RNA binding by NS4B is amenable to pharmacologic disruption. The present invention provides an in vitro RNA binding assay in a format enabling simultaneous analysis of multiple conditions, mutants, and replicates, quantitative dissociation constant (Kd) measurements, and high-throughput screening for potential pharmacologic inhibitors.

Like the majority of drug targets[12], NS4B is a membrane protein (SEQ ID No: 13), as shown in FIG. 7b. Membrane proteins are notoriously difficult to express and characterize biochemically, especially in the quantities required for pharmaceutical screening. Moreover, solubilization by detergents can alter their natural membrane associated topology. To ameliorate these problems, the present invention provides microfluidic tools to perform binding assays with nanoliter protein consumption. This enables use of an in vitro cell lysate expression system, which is supplemented with microsomal membranes to create more natural folding conditions, under which the best NS4B topology data available to date has been obtained[13]. The reduced yield relative to conventional expression methods is offset by low sample consumption.

Previous microfluidic tools to measure drug interactions have been limited to enzymatic targets which can catalyze formation of a fluorescent substrate[14]. In an embodiment of the invention, binding constants are directly measured by using mechanical trapping of molecular interactions (MITOMI), a microfluidic affinity assay that has previously been used to measure interactions between transcription factors and DNA[15]. Results obtained using the methods of the invention show that MITOMI can be used both to measure binding constants of membrane protein-RNA interactions and to measure inhibition of such interactions by small molecules in a high throughput screen. The latter point is particularly surprising in that the elastomer used to fabricate the device is known to have limitations in chemical compatibility[16,17]; here we show that this does not prevent its use in a drug screen nor does it prevent discovery of a small molecule with the desired pharmacological properties. Taken together, the results obtained using these methods of the invention reveal a novel HCV target and constitute the first demonstration that microfluidic technology can be used to discover a new pharmaceutical, thereby successfully consummating more than a decade of effort to apply microfluidic tools to drug discovery[18,19].

Results

The use of the microfluidic platform for RNA binding was validated by studying two human proteins from the embryonic lethal abnormal visual system (ELAV) family, the RNA binding activity of which has been previously well-characterized. This methodology was then applied to study RNA interactions with the transmembrane HCV NS4B protein. This platform was used to (i) test the hypothesis that HCV NS4B binds RNA, (ii) determine the Kd for this interaction, (iii) study the substrate specificity of this binding, (iv) determine the amino acids within NS4B required for RNA binding, and (v) screen a compound library for pharmacologic inhibitors of NS4B RNA binding and HCV replication.

Microfluidic Assay Validation: HuD Binding to RNA.

Figure 5:
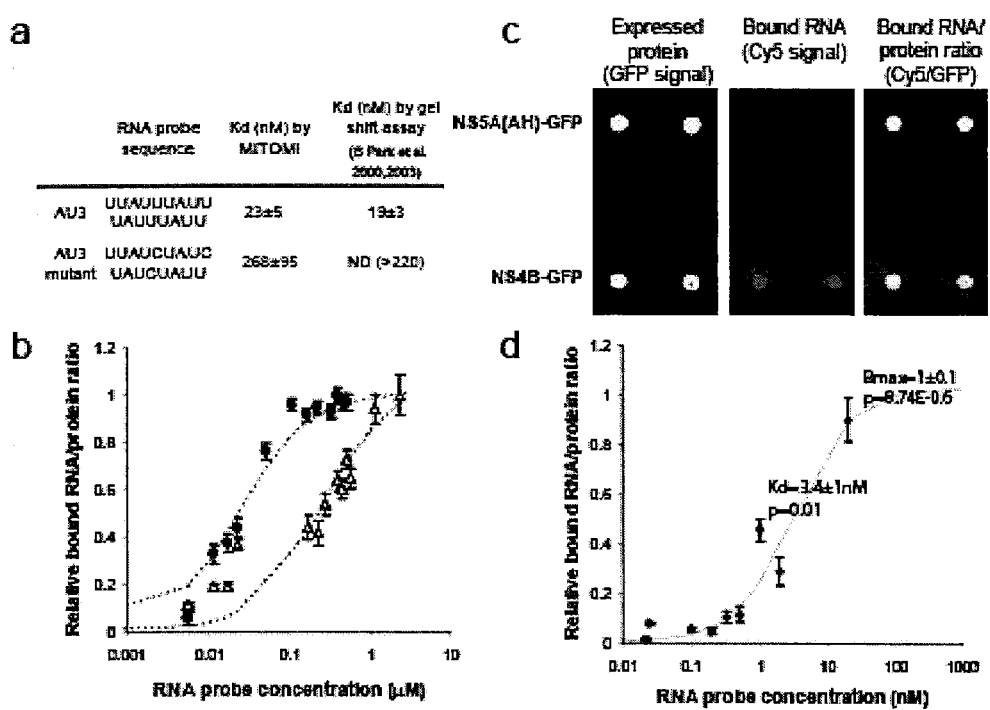
FIGS. 5a-5d illustrate results from protein-RNA interactions measured on a microfluidic platform.
Figure 10:
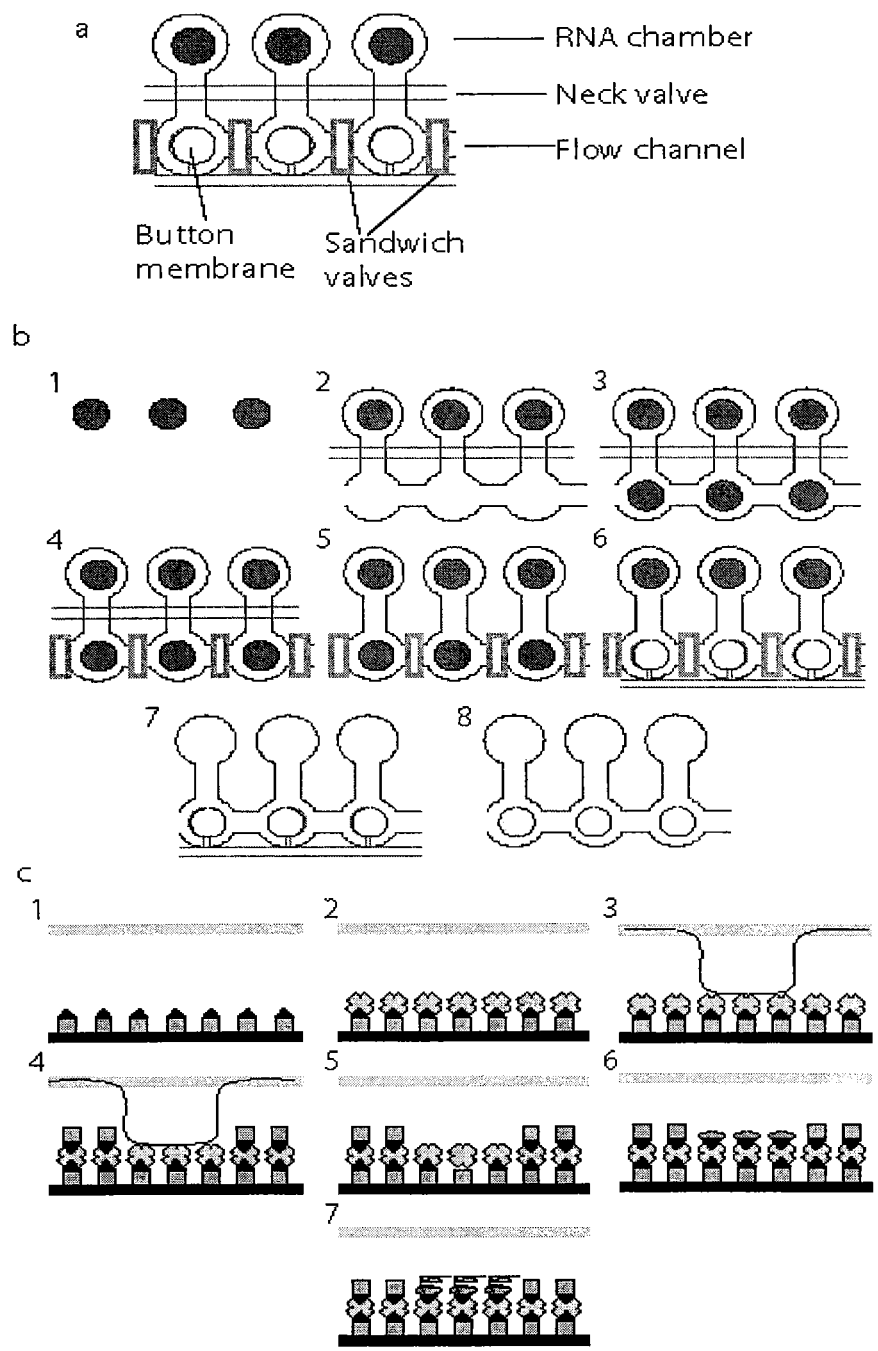
FIGS. 10a-10c illustrate schematics of the microfluidic based RNA binding assay.

HuD is a host cell protein from the ELAV-like family with well characterized RNA binding activity[20-22]. It is a cytoplasmic protein that contains 3 conserved RNA recognition motifs through which it binds AU-rich elements (ARE) in the 3' UTR (un-translated region) of genes such as those encoding cytokines and proto-oncogenes. Binding was tested against two Cy3-labeled RNA probes: AU3 and a known AU3 mutant to which HuD binding is impaired[21,22] (FIG. 5). RNA binding experiments with MITOMI were performed essentially as described by Maerkl and Quake[15], except that in this case RNA was used instead of DNA (FIG. 10).

Briefly, a microarray of target RNA sequences labeled with Cy3 was spotted onto an epoxy-coated slide. These arrays were used to program the microfluidic devices by aligning each spot in the array to a unit cell in the device. After bonding the microfluidic device to a microarray, it was subjected to surface patterning that resulted in a circular area coated with biotinylated anti-histidine antibodies within each unit cell. The device was then loaded with in vitro transcription/translation mixture containing DNA templates coding for HuD fused in frame with a C-terminal V5-6 histidine tag (HuD-V5-his) or Gus protein fused in frame with a C-terminal 6 histidine tag (Gus-his). Bodipy-labeled tRNA$_{Lys}$ was added for protein labeling. Each unit cell was then isolated using micromechanical valves followed by an incubation to allow protein synthesis, binding of the synthesized protein to the surface biotinylated anti-his antibodies, solvation of target RNA, and equilibration of proteins and target RNA. MITOMI was then performed by actuation of a "button" membrane to trap surface-bound complexes while expelling any solution phase molecules. After a brief wash to remove untrapped unbound material, the trapped molecules and expressed protein were subsequently detected with an array scanner. The ratio of bound RNA to expressed protein was calculated for each data point by measuring the median signal of Cy3 to median signal of bodipy.

Figure 11:
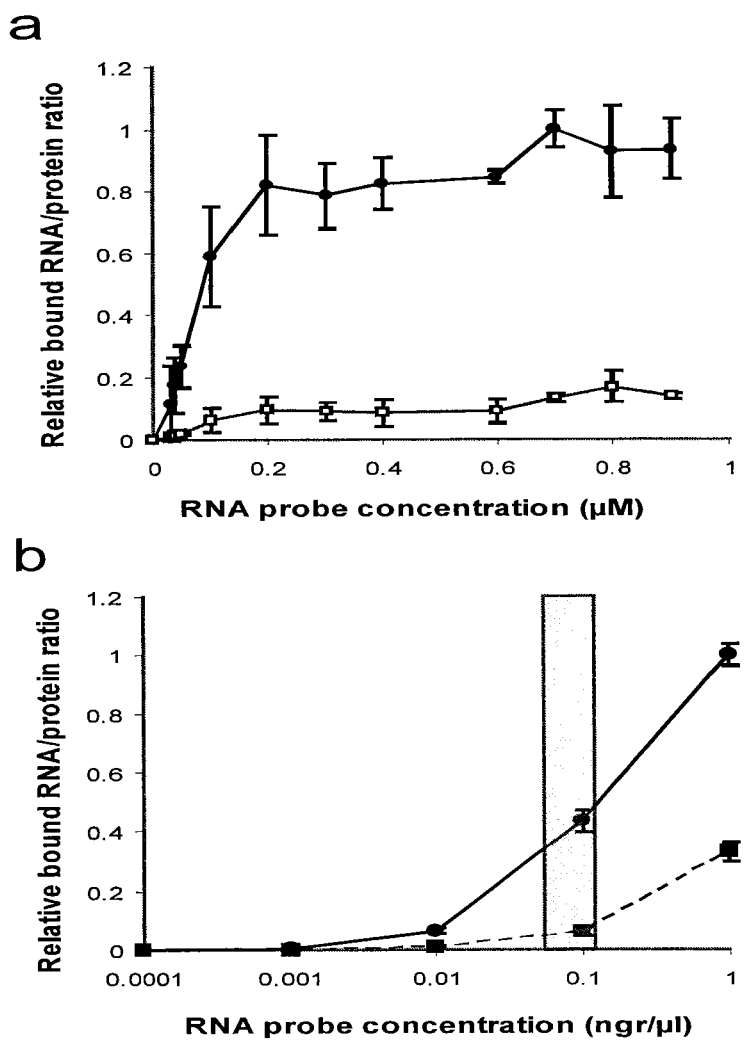
FIGS. 11a-11b illustrate a graph showing the signal to noise ratio in an RNA binding assay.
Figure 12:
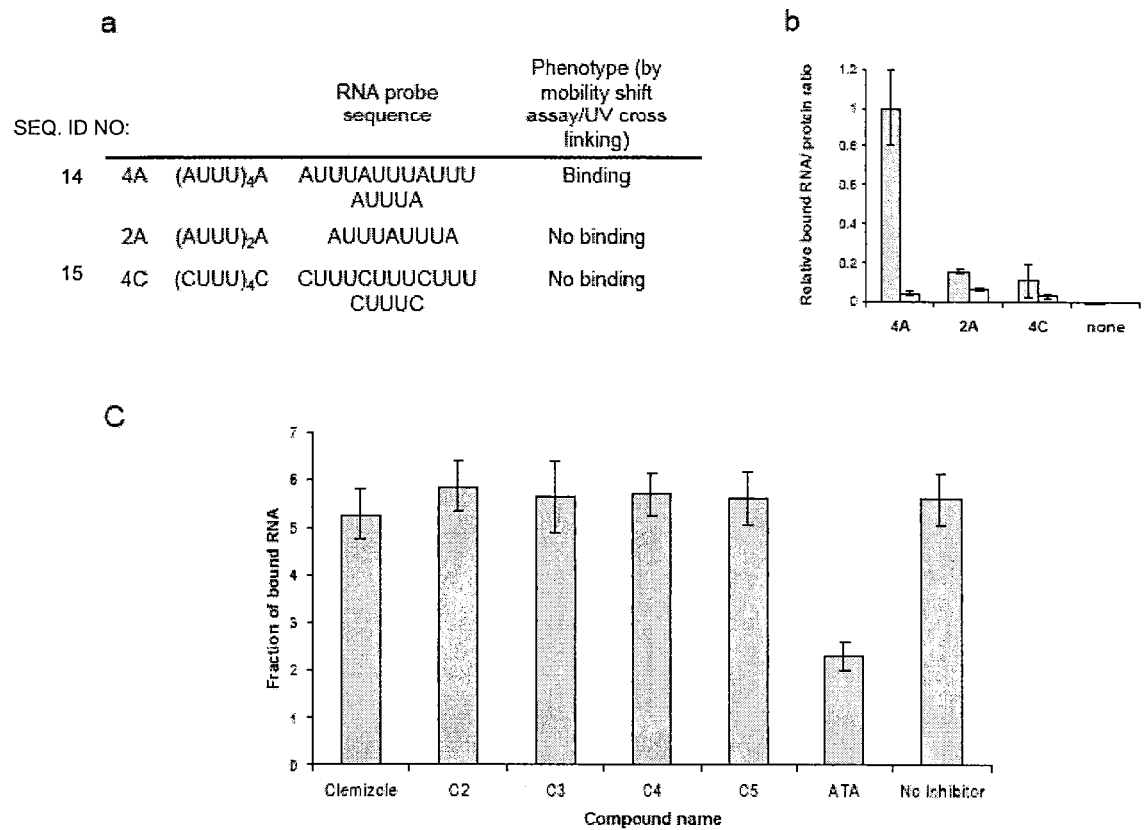
FIGS. 12a-12c illustrate results from the microfluidics-based analysis of RNA binding by another human protein from the ELAV-like family, HuR (ELAV L1).

As shown in FIG. 5a, the assay detected strong binding of HuD to the AU3 RNA probe; background binding by Gus-his was 7-16 fold lower than the HuD signal. This background level did not increase with RNA probe concentration and was subtracted from all chambers (FIG. 11). The binding affinity of HuD to the AU3 probe was much greater than to the AU3 mutant probe: the Kd for the AU3 binding was determined to be 23±5 nM and for the AU3 mutant 268±95 nM (FIG. 5a). These values agree with previous measurements in a gel shift assay[21,22] and serve to validate the MITOMI microfluidic affinity assay for RNA-protein interactions. RNA binding analysis of another protein from the ELAV-like family, HuR, is shown in FIG. 12.

NS4B Binds HCV RNA and Determination of Kd by Microfluidics.

Figure 13:
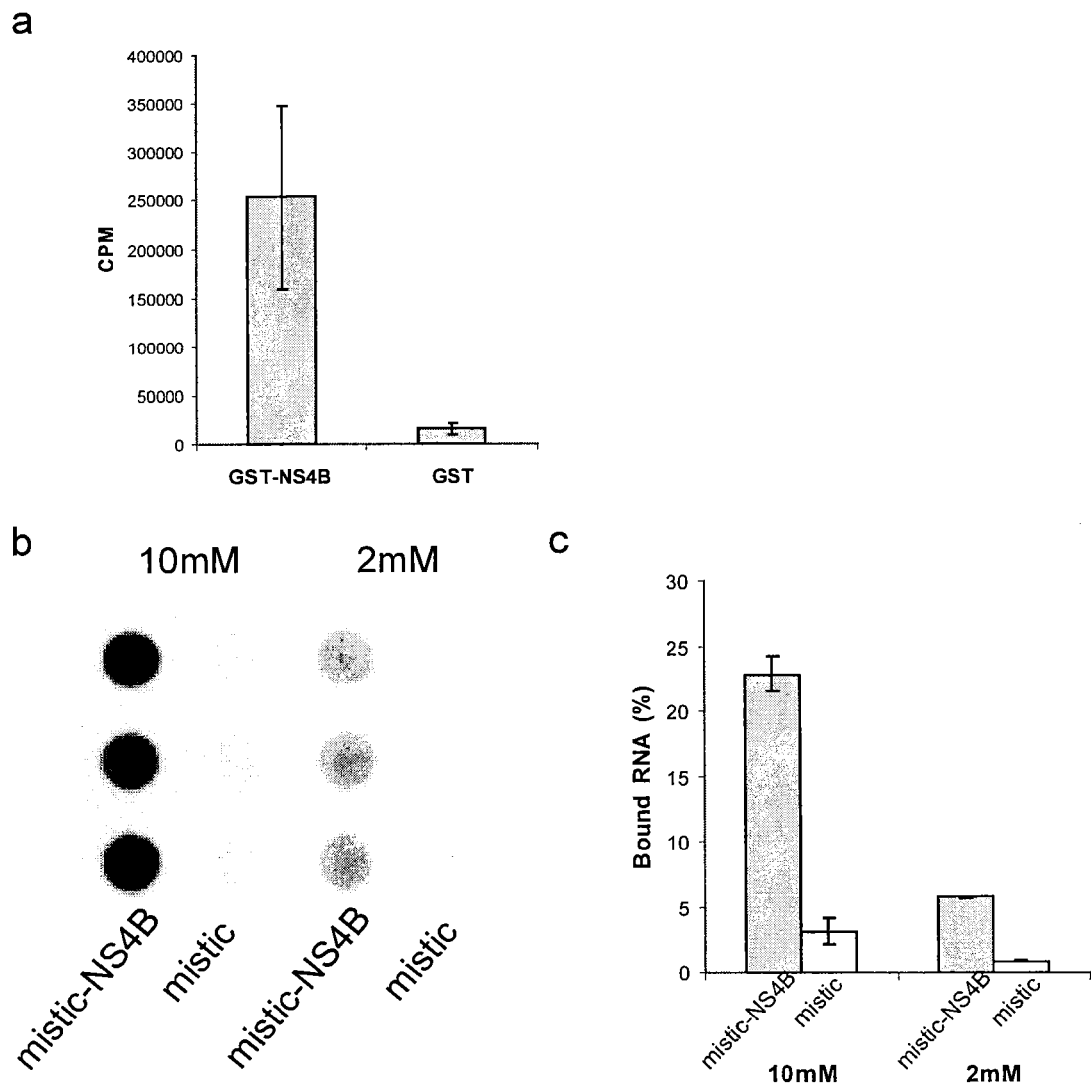
FIGS. 13a-13c illustrate results relating to the binding of NS4B to HCV RNA.

This system was then used to test whether HCV NS4B binds RNA. Because NS4B is important in viral RNA replication, and initiation of positive-strand RNA synthesis is likely to start at the 3' terminus of the negative-strand RNA, binding of NS4B to this region was tested first, using a probe designated 3' negative terminus. A fusion of the amphipathic helix (AH) of NS5A to the N-terminus of GFP[5] was used as a negative control. This protein also binds to membranes and can thus anchor the microsomal membranes to the device surface via the interaction of GFP with anti-GFP (FIG. 5c). The Kd of NS4B binding to the 3' terminus of the HCV negative strand RNA was measured at 3.4±1.0 nM (FIG. 5d). This appears to be the first evidence that HCV NS4B binds RNA. Conventional GST pull down assays and RNA filter binding assays using recombinant forms of purified NS4B expressed in E. coli confirmed this finding (FIG. 13), although these were less convenient and amenable to the types of analyses and high throughput format provided by the methods of the invention.

NS4B Specifically Binds the 3' Terminus of the Negative Viral Strand.

Figure 6:
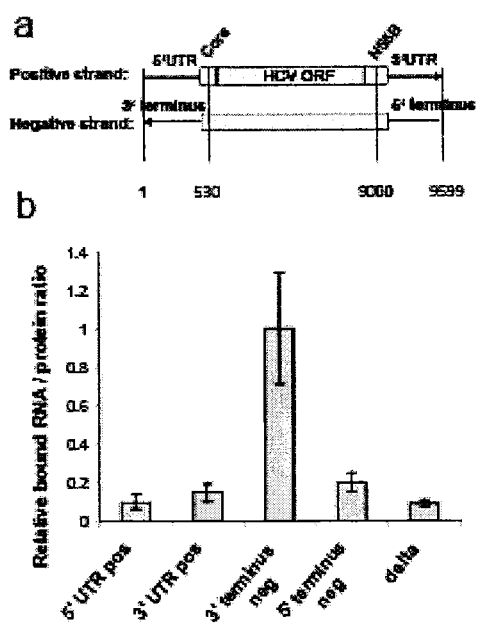
FIGS. 6a and 6b illustrate results that show that NS4B binds specifically to the 3' terminus of the HCV negative strand RNA.

The substrate specificity of the observed NS4B-HCV RNA interaction was measured using three additional HCV probes (FIG. 6a). The probes, designated 5' UTR pos and 3' UTR pos, correspond to the 5' UTR and 3' UTR sequences of the positive viral strand, respectively, and 5' negative terminus corresponds to the 5' terminus of the negative strand. The RNA binding experiment was repeated and binding of NS4B to equimolar concentrations (3 nM) of the various probes was compared. As shown in FIG. 6b, while NS4B binds all four HCV probes, its apparent affinity to the 3' negative terminus probe is 5-12 fold greater than to the other three HCV RNA regions tested or to an unrelated delta virus RNA genome sequence[23,24] (see FIG. 6b). These findings support a conclusion that it is the RNA sequence, and likely the secondary RNA structure, that determines the specificity of NS4B binding to the 3' terminus of the negative strand.

An Arginine Rich-Like Motif in NS4B is Essential for RNA Binding and for HCV Replication.

Various structural motifs responsible for the interaction between proteins and RNA have been reported[25]. One of these is the arginine rich motif (ARM). ARMs were originally defined as short (10 to 20 amino acids) arginine-rich sequences found in viral, bacteriophage, and ribosomal proteins (FIG. 7a)[9,25,26]. There is little identity between ARM sequences, other than the preponderance of arginine residues. Subsequently, ARM-like motifs, consisting of longer sequences containing fewer arginines were identified[9,26]. Inspection of the primary sequence of NS4B reveals the presence of multiple positively-charged amino acids (see FIG. 7b). The majority of these arginine residues are within the last 71 amino acids, in the C-terminal region of NS4B (FIGS. 7b and 7c). This region is predicted to form a cytoplasmic segment based on empirical topology studies using glycosylation markers[13]. Elements of this region conform with previously described ARM-like motifs.

Figure 16:
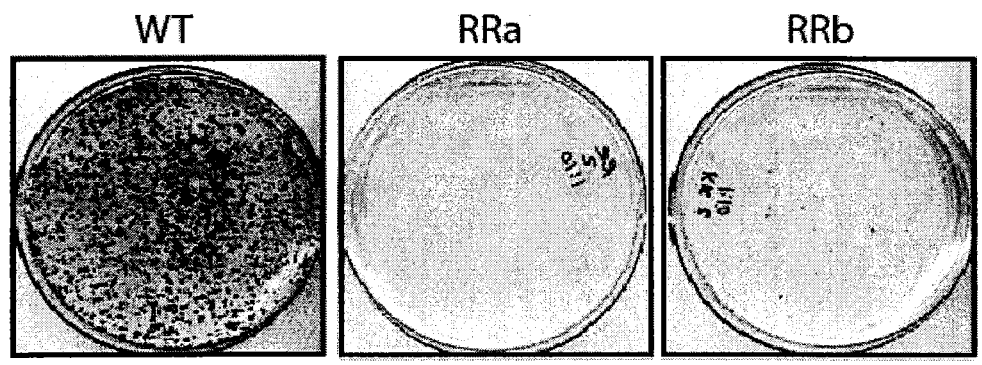
FIG. 16 is a digital image that shows that the RRb mutation decreased replication by ~45 fold, and the replicon harboring the RRa mutation was completely defective in RNA replication.

Using a series of point mutations, we tested if RNA binding by NS4B is mediated by some of its positively-charged residues. A substitution of Arg-Arg in positions 192-193 with Ala-Ala was termed "RRa mutant" and a similar substitution in positions 247-248 was designated "RRb mutant". As shown in FIG. 7d, while the RRb mutant decreased binding by NS4B to the 3' negative terminus probe by 5 fold, RNA binding activity to the RRa mutant was completely eliminated at the same probe concentration (1.5 nM). These results support a hypothesis that the tested arginine residues mediate RNA binding by NS4B in vitro. To test the hypothesis that these positively charged residues are also important for HCV replication, these mutations were introduced into high efficiency subgenomic HCV replicons and those replicons assayed in standard replicon colony formation assays. As shown in FIG. 16, while the RRb mutation decreased replication by ~45 fold, the replicon harboring the RRa mutation was completely defective in RNA replication. Moreover, the degree of replication inhibition correlated with the degree of NS4B RNA binding impairment caused by the various mutations (see FIG. 7d). Furthermore, control experiments suggested that the dramatic effect on replication was not the result of altered expression or mislocalization of the protein. Rather, these subtle mutations appear to be affecting a key regulatory site in NS4B. These results support a conclusion that efficient binding of HCV RNA is required for viral replication in vitro. Alignment of the sequences of natural HCV isolates currently available in databases reveals that these positively-charged residues are highly conserved across all HCV genotypes. This conservation support a conclusion that there is a requirement for the RNA binding residues for productive viral infection in vivo.

High-Throughput Screening for Inhibitory Compounds.

Figure 8:
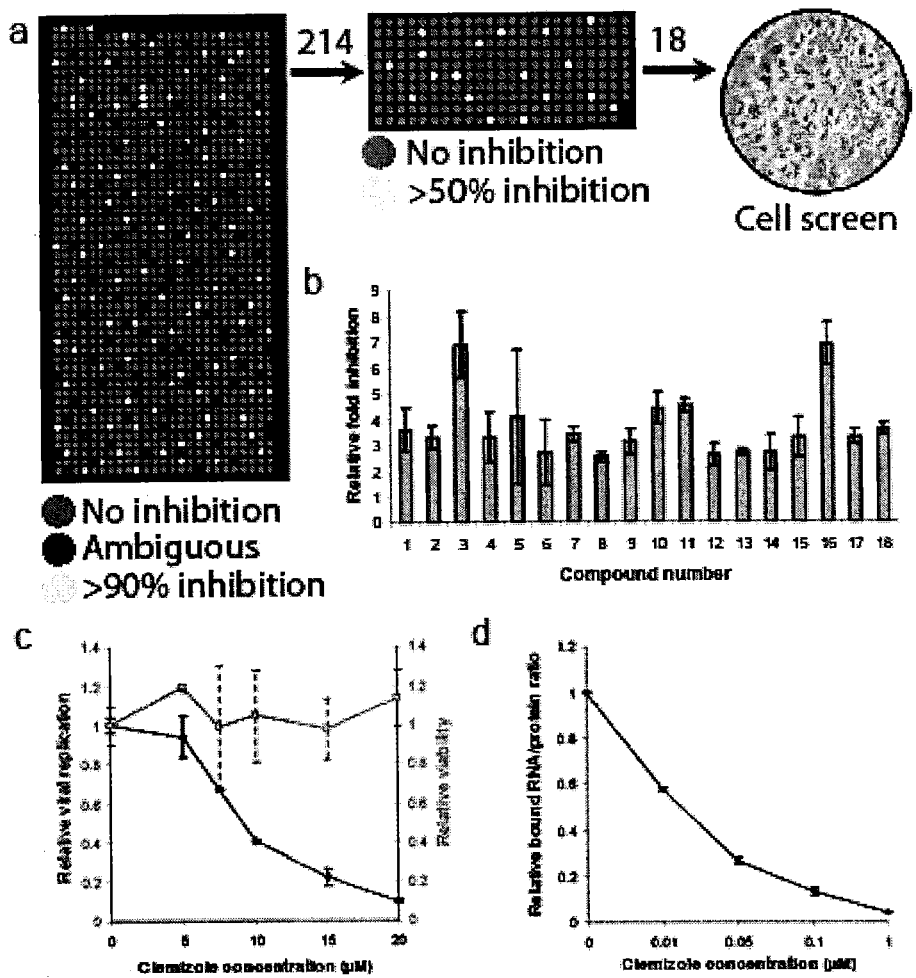
FIGS. 8a-8d illustrates that a small molecule screen reveals that clemizole hydrochloride inhibits RNA binding by NS4B and in vivo HCV RNA replication.

A compound library was screened in accordance with the methods of the invention to identify small molecules that could inhibit the RNA-NS4B interaction. As shown in FIG. 8a, 1280 compounds from a small molecular library were spotted on epoxy-coated slides as a microarray. The array was allowed to dry, and was then aligned and bonded to a microfluidic device as described above. The rest of the assay was performed as before, except that the device was loaded with NS4B-GFP followed by Cy5-labeled 3' terminus negative RNA probe. In the primary screen, the compounds were spotted at a concentration of ~1 mM. The entire library was screened in duplicate using only two microfluidic devices. Out of 1280 compounds, 104 were found to have an inhibitory effect (>90% inhibition) on RNA binding by NS4B. In addition, there were 110 compounds for which there was a significant discrepancy between the two tested replicates or to which one or two of the measurements were disrupted due to technical reasons.

The 214 compounds (104+110) identified in the primary screen were subjected to a secondary screen (FIG. 8a). This was done in a similar manner except that a smaller device was used, the spotted compound concentration was 10 fold lower than in the primary screen and 5 replicates were spotted for each compound. Eighteen compounds were confirmed to significantly inhibit RNA binding by NS4B out of the 214 compounds tested (FIG. 8b). Most of the identified compounds did not inhibit binding of HuR protein to its own 4A target RNA sequence (FIG. 12) nor did they inhibit HuR binding to its previously described HCV RNA target: the 3' terminus of the negative viral strand[27], suggesting that these hits are specific. This data and additional data supporting the validity of the screen are presented in FIG. 14.

Inhibitors of HCV RNA Replication.

Figure 15:
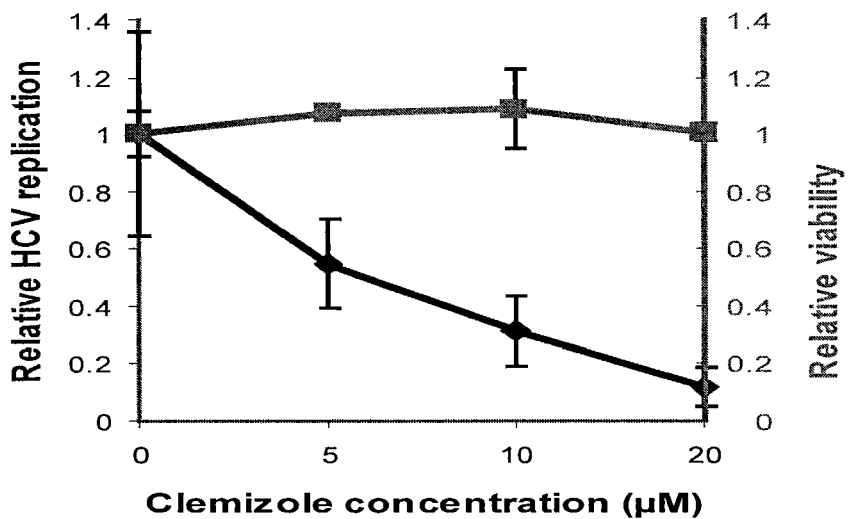
FIG. 15 illustrates results that show that clemizole inhibits HCV replication as evidenced by real-time PCR assays. Real-time PCR assay of HCV replication levels show that clemizole inhibits HCV replication (left axis ◆ (bottom curve)) with no measurable toxicity to the cell (right axis, ■ (top curve)).

The in vivo antiviral effect on HCV RNA replication of the inhibitory compounds identified in the above screen was measured. Following electroporation with a full-length HCV RNA genome harboring a Luciferase reporter gene[28], Huh7.5 cells were grown in the presence of increasing concentrations of these compounds. Luciferase assays were performed at 72 hr. In parallel, the viability of cells in the presence of the compounds was assessed by an Alamar Blue-based assay. Six of the compounds showed some antiviral effect above that solely attributable to cellular toxicity. Clemizole hydrochloride (1-p-Chlorobenzyl-2-(1-pyrrolidinyl) methylbenzimidazole hydrochloride), an H1 histamine receptor antagonist, was found to significantly inhibit HCV replication. A tenfold decrease in viral replication was measured at 20 µM concentration of the drug, with an EC50 of ~8 µM (FIG. 8c). At these concentrations, there was no measurable cellular toxicity (FIG. 8c). Similar results were obtained by real-time PCR assays performed in clemizole-treated Huh7.5 cells infected with the infectious HCV clone (J6/JFH)[29] (FIG. 15). The in vitro IC50 of clemizole for RNA binding by NS4B is ~24±1 nM (FIG. 8d).

Figure 17:
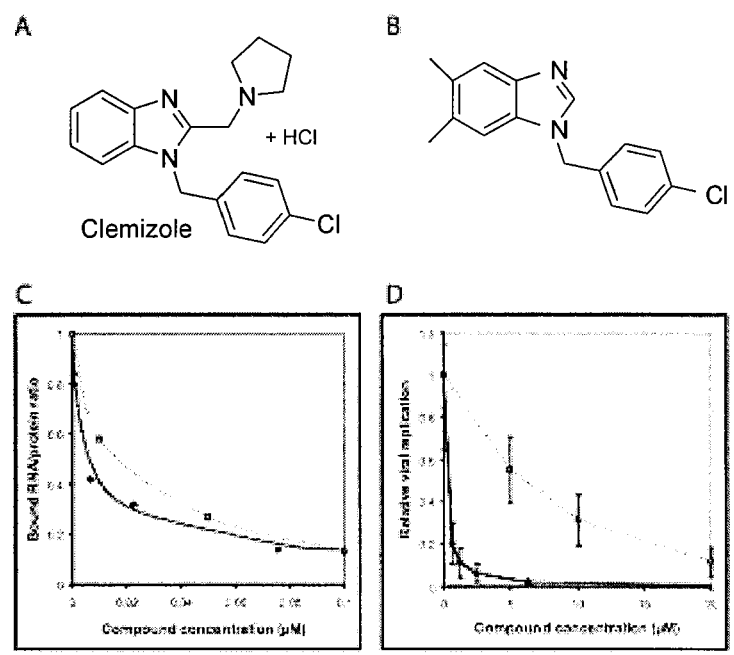
FIG. 17A shows the chemical structure of clemizole hydrochloride.
FIG. 17B shows the chemical structure of a clemizole derivative molecule with increased potency and efficacy.
FIG. 17C illustrates a graph that shows the in vitro inhibition curve of a Clemizole derivative molecule (●) and the parental Clemizole hydrochloride compound (□), as measured by microfluidics (bound RNA/protein ratio vs compound concentration (µM)).
FIG. 17D illustrates a graph that shows a dose response curve of HCV replication in the presence of increasing concentrations of a Clemizole derivative molecule (●) and the parental Clemizole hydrochloride compound (□), as measured by a real-time PCR assay in HCV-infected cells (relative viral replication vs compound concentration (µM)).

Increased Potency and Efficacy of a Clemizole Hydrochloride Derivative Molecule:

Screening conducted using the methods described herein this application to identify a clemizole analog with increased potency. An example of one such molecule is shown in FIG. 17, which has the following data:

FIG. 17A-*Chemical* structure of Clemizole hydrochloride.
FIG. 17B-*Chemical* structure of a Clemizole derivative molecule with increased potency and efficacy.

FIG. 17C—In vitro inhibition curve of Clemizole derivative molecule (●) and the parental Clemizole hydrochloride compound (□), as measured by microfluidics.

FIG. 17D—A dose response curve of HCV replication in the presence of increasing concentrations of Clemizole derivative molecule (●) and Clemizole hydrochloride (□), as measured by a real-time PCR assay in HCV-infected cells.

Bars represent standard deviation.

As can be seen, this derivative compound has increased in vitro potency (IC50 of 6 nM vs 24 mM for Clemizole) (FIG. 17C). Importantly, this compound also demonstrated a higher antiviral activity against HCV replication in cells with an EC50 of 1 μM (versus 8 μM for Clemizole) (FIG. 178D).

Taken together, the above data combined with the analysis of resistant mutants provides compelling genetic, biochemical, and pharmacologic evidence for Clemizole's mechanism of action. Moreover these data demonstrate that more potent inhibitory molecules can be identified using the methods of the invention.

Clemizole-Resistant Mutants.

The mechanism of action of clemizole's antiviral activity was further substantiated by selecting for clemizole resistant HCV mutants. Established HCV replicon-harboring cells and Huh7 cells electroporated de novo with a genotype 1b subgenomic HCV replicon (Bart 79I)[30] were passaged in the presence of the drug, yielding ~60 colonies that were able to grow in the presence of the compound. 11 individual colonies were successfully expanded, passaged 5-10 times and the HCV RNA replicating in the cells was subjected to sequence analysis. In addition, RNA from a pool of clemizole-resistant colonies was isolated and subjected to a similar analysis. Three colonies were found to harbor replicons with mutations that mapped to the NS4B region, and 6 colonies were found to harbor replicons with mutations that mapped to the negative strand 3' terminus RNA region. (Of note, the location of resistance mutations selected in the presence of the clemizole derivative molecule of FIG. 17B mapped to similar locations within the HCV genome). In addition, there was one colony with mutations that mapped to both NS4B and the negative strand 3' terminus, and one where the location of the mutation conferring resistance to clemizole was not yet identified. No such mutations were identified in 10 replicon colonies that were passaged in parallel in the absence of the drug.

Figure 9:
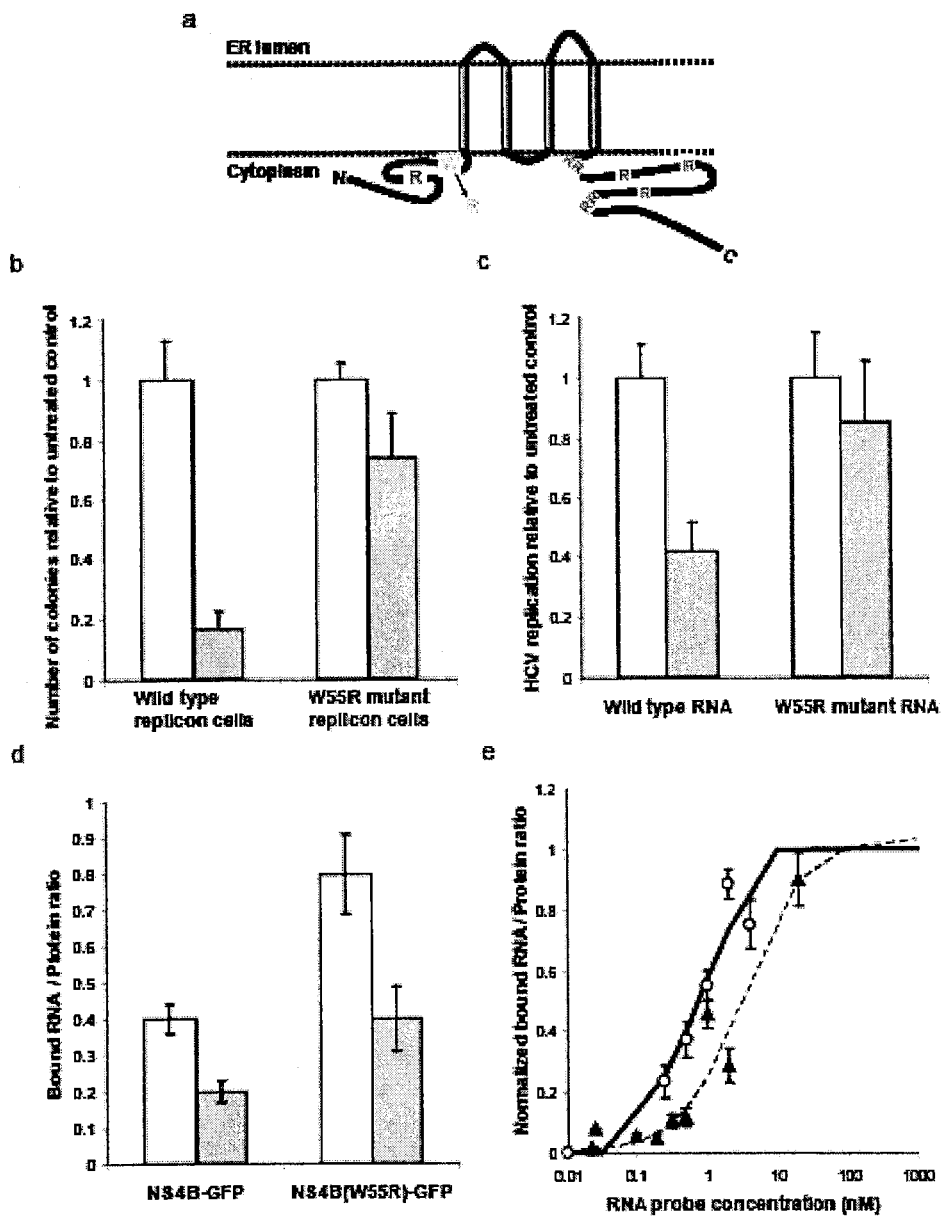
FIGS. 9a-9e illustrate results relating to clemizole-resistant mutants.

Two of the clemizole-resistant NS4B mutants were characterized in detail. The first, W55R is depicted in FIG. 9a. It involves the substitution of an arginine for the tryptophan at amino acid 55 within a predicted cytoplasmically-oriented segment of NS4B. This mutation is sufficient to confer a clemizole-resistant phenotype in cells: Huh7.5 cells transfected with either whole cell RNA extracted from the W55R mutant cells (FIG. 9b) or with in vitro-transcribed J6/JFH RNA encoding this point mutation and a linked luciferase reporter gene (FIG. 9c) were unaffected by 10 μM clemizole. EC50 of clemizole on the W55R mutant J6/JFH RNA was ~18 μM (2.25 times the EC50 on the wild type RNA). Similar to other HCV mutants resistant to an NS3 protease inhibitor[31], the absolute level of replication of the W55R mutant was lower than that of the wild type genome, indicating that the drug-resistant mutation comes at the cost of impaired replication fitness.

This mutation was also introduced into the NS4B-GFP vector and the resulting vector tested for its RNA binding activity using the in vitro microfluidic assay of the invention. Although both mutant and wild type NS4B proteins experienced ~ a 2 fold reduction of RNA binding in the presence of 10 nM clemizole, because the baseline RNA binding of the mutant is higher, the residual amount of RNA bound by the mutant in the presence of clemizole was comparable to that bound by the wild type in the absence of clemizole (FIG. 9d). Furthermore, as shown in FIG. 9e, this mutant demonstrates greater apparent affinity to the viral RNA with a Kd of 0.75 nM (vs 3.4 nM for wild type NS4B).

The second clemizole-resistant mutation, termed R214Q, was identified in a resistant colony as well as in pooled resistant cells. It involves the substitution of a glutamine for the arginine at amino acid 214 within the cytoplasmic C-terminal segment of NS4B. Similar results to the first mutation were obtained in cellular and in vitro analyses done on this mutation, with an EC50 of 40.3 μM (~5 times higher than the EC50 on the wild type RNA) in the luciferase reporter linked replication assay and a Kd of 0.6 nM in the in vitro binding assay. Presumably, both of these mutations alter the conformation of NS4B so as to increase its affinity for the viral RNA. Indeed the Kd's measured by the in vitro RNA binding assay reflect this. Taken together, the above data provides compelling genetic and biochemical evidence for clemizole's mechanism of action.

Discussion

The above results demonstrate that HCV NS4B binds RNA, and that this binding is specific for the 3' terminus of the negative strand of the viral genome. Because the in-vivo specificity of this interaction has not yet been determined quantitatively, one should use the usual caution in extrapolating the numerical value of the in vitro results reported here. An arginine rich-like motif in NS4B is essential for RNA binding and for HCV replication. Clemizole hydrochloride was found to have a significant in vivo antiviral effect on HCV RNA replication mediated by its inhibition of NS4B's RNA binding, with little toxicity for the host cell.

Because NS4B is associated with membranes[5] and is known to induce membrane replication sites[4], its RNA binding activity offers a mechanism to incorporate the viral genome into the HCV replication compartment. This may facilitate the initiation of synthesis of nascent positive strand from the membrane anchored negative strand. NS4B may also act by recruiting the polymerase complex to the HCV RNA, via its interaction with the NS5B polymerase or other components of the replication complex[32].

The in vitro IC50 of clemizole for RNA binding by NS4B is ~24±1 nM, whereas its EC50 for viral replication is ~8 μM. It is possible that poor cellular permeability accounts for the ~400 fold difference between the IC50 measured for in vitro RNA binding by NS4B and the EC50 measured for the antiviral effect in cells. Improved drug delivery and optimization of the compound following structure-activity relationship (SAR) analysis are expected to provide more potent antiviral agents, and the microfluidic system and screening methods of the invention can facilitate this process.

This study also demonstrates the utility of a microfluidic approach. The microfluidic affinity assay has several important advantages over currently used methods which make it a promising and general tool for drug discovery, especially against membrane bound targets. First, protein synthesis by mammalian reticulocyte lysates in the presence of microsomal membranes provides the natural conditions required for protein folding. Second, the microfluidic assay eliminates the need for a high level of protein expression and purification, a problem faced by currently used methods. Third, this assay is capable of detecting transient and low affinity interactions[15]. Fourth, the microfluidic device is capable of making many parallel measurements, and therefore can be used for high throughput screening. Finally, and in spite of known chemical compatibility issues with the elastomer used to fabricate the device, one can successfully screen and discover small molecules with desired pharmacological properties using the device and method.

As with HIV and tuberculosis, effective pharmacologic control of HCV will likely best be achieved by a cocktail of multiple drugs against independent virus-specific targets. Combination of even a moderate NS4B inhibitor with existing and/or other emerging anti-HCV agents represents an attractive paradigm for increasing current virologic response rates. Although more potent inhibitors than clemizole can be obtained, because clemizole has already been extensively used in humans (albeit for a different indication), it can find immediate use as an anti-HCV therapeutic and serve as a critical component of next generation anti-HCV strategies in accordance with the present invention.

Methods

Plasmids:

Standard recombinant DNA technology was used to construct and purify all plasmids. All regions that were amplified by PCR were analyzed by automated DNA sequencing. Plasmid DNAs were prepared from large-scale bacterial cultures and purified by a Maxiprep kit (Marligen Biosciences). Restriction enzymes were purchased from New England Biolabs.

The open reading frames (ORF) of HuR and HuD were obtained from the ORFeome library of cDNA clones (Open biosystems). These ORFs were inserted into the expression vector pcDNA-Dest 40 vector (Invitrogen) by the use of gateway technology (Invitrogen) allowing addition of a C-terminal V5-his tag.

The plasmid pcDNA-NS4B-GFP encoding NS4B of genotype 1a fused in frame with a C-terminal GFP was previously described[5]. The mutations RRa, RRb and W55R were introduced into this plasmid by site-directed mutagenesis (using the QuikChange kit (Stratagene)). The plasmid NS5A(AH) GFP was constructed as previously reported. Gus-his vector was obtained from Roche.

The plasmids pcDNA3.1-5' UTR pos which encodes the 5' UTR of the positive viral strand, was generated by amplification of the 5' UTR positive sequence from the Bart79I plasmid[33] with primers containing EcoRV restriction sites, digestion with EcoRV and ligation into the corresponding site in pcDNA3.1 (Invitrogen). The plasmid pcDNA3.1-3' negative terminus which encodes the 3' terminal region of the negative RNA strand was generated the same way except that the EcoRV-flanked insert was ligated in an inverse orientation.

The plasmids pcDNA3.1-3' UTR pos and 5' negative terminus were similarly generated except that the inserted gene was flanked by HindIII and XhoI restriction sites.

The vector encoding the delta virus genomic RNA sequence was cloned by inserting NheI flanked HDV sequence into a pSPT19 vector (Roche Diagnostics) cut with XbaI[23,24].

The plasmid FL-J6/JFH-5'C19Rluc2AUbi that consists of the full-length HCV genome and expresses Renilla luciferase was a gift from Dr. Charles M. Rice[28]. The W55R mutation was introduced into this plasmid by site-directed mutagenesis (using the QuikChange kit (Stratagene)).

In Vitro RNA Transcription and Fluorescent and Radioactive Labeling.

Plasmid DNA of the 5' and 3' terminal regions of the negative and positive viral strands were linearized with XbaI. The plasmid DNA of the delta genomic sequence was linearized with XbaI. Linearized plasmids were then treated with proteinase K, followed by phenol-chloroform extraction and precipitation with ethanol. The DNA was resuspended in RNase free water to a final concentration of 1 µg/µl. 4 µgs of DNA were used as a template for transcription with the T7 MEGAscript (Ambion) according to the manufacturer's protocol. The template DNA was digested by the addition of 5 U of RQ1 DNase (Ambion) and a 15-min incubation at 37° C. The unincorporated ribonucleotides were removed by size exclusion with a Micro Bio-Spin P-30 column (Bio-Rad), and the transcribed RNA was extracted with phenol-chloroform, followed by precipitation in ethanol. The RNA pellet was washed with 70% ethanol and resuspended in $H_2O$. Determination of the RNA concentration was performed by measurement of the optical density at 260 nm. The integrity of the RNA and its concentration were confirmed by 1% agarose gel electrophoresis and ethidium bromide staining.

The RNA sequences were labeled with Cy5 by using Label IT kit (Minis) according to the manufacturer protocol followed by purification on a microspin column (Mirus) and ethanol precipitation. The number of fluorescent labels per RNA molecule was determined by measuring the spectrophotometric absorbance of the nucleic-dye conjugate at 260 nm and the $\lambda_{MAX}$ for Cy5 (650 nm). This was proportional to the probe's length and was used to adjust binding experiments results.

Cy3-labeled RNA probes used to study RNA binding by HuR and HuD were purchased from IDT.

Radioactive labeling of RNA probes with 32P was done as previously described[34].

Device Design:

Device fabrication and design was done essentially as described[15]. In brief, a "control" layer, which harbors all channels required to actuate the valves, is situated on top of a "flow" layer, which contains the network of channels being controlled. All biological assays and fluid manipulations are performed on the flow layer. A valve is created where a control channel crosses a flow channel. The resulting thin membrane in the junction between the two channels can be deflected by hydraulic actuation. Using multiplexed valve systems allows a large number of elastomeric microvalves to perform complex fluidic manipulations within these devices. Introduction of fluid into these devices is accomplished through steel pins inserted into holes punched through the silicone. Computer-controlled external solenoid valves allow actuation of multiplexors, which in turn allow complex addressing of a large number of microvalves. Each unit cell is controlled by three micromechanical valves as well as a "button" membrane (FIG. 10). The "button membrane" of each unit cell masks a circular area within the flow channel between two "sandwich" valves. Aligning and bonding a microarray to the device, allows positioning of the spotted material (RNA probes or inhibitory compounds) within the "RNA chamber" of each unit cell. This chamber can then be opened to the flow channel by the control of a "neck valve". The used devices had either 640 or 2400 unit cells.

RNA Binding Assay.

The approach used was a modification of the previously described method for protein-DNA interactions[15] (FIG. 10).

1. Soluble Proteins: A. RNA Arraying and Device Alignment.

First, a dilution series of Cy3-labeled target RNA sequences (IDT) was spotted as a microarray onto epoxy coated glass substrates slide (CEL Associates) by OmniGrid Micro (GeneMachines) microarrayer using a CMP3B pin (TeleChem International, Inc.) with column and row pitches of 680 mm and 320 mm, respectively. Each sample solution contained 1% BSA in $dH_2O$ to prevent covalent linkage of the target RNA to the epoxy functional groups as well as for visualization during alignment. After spotting, the arrays were quality controlled on a GenePix4000b (Molecular Devices). The arrays were then aligned to a microfluidic device by hand on a SMZ1500 (Nikon) stereoscope and bonded overnight in the dark on a heated plate at 40° C.

B. Surface Chemistry (FIG. 10c).

All devices were driven between 10 and 15 psi in the control line and between 4 and 6 psi for the flow line. For the initial surface derivatization steps the chamber valves remained closed to prevent liquid from entering the chambers containing the spotted RNA targets. First, all accessible surface area was derivatized by flowing a solution of biotinylated BSA (Pierce) resuspended to 2 mg/mL in $dH_2O$ for 30 min through all channels, followed by a 10 min PBS wash. Next a 500 µg/mL Neutravidin (Pierce) solution in PBS was flowed over the surface for 20 min, followed by a 10 min PBS wash. Next, the "button" membrane was closed and the PBS wash continued for an additional 5 min. Then all remaining accessible surface area except for the circular area of 60 µm masked by the button was passivated with the same biotinylated solution as above for 30 min, followed by a 10 min PBS wash. Finally, a 1:1 solution of biotinylated-5-histidine antibody (Qiagen) in 2% BSA in PBS was loaded for 2-5 min, after which the "button" membrane was opened and flow continued for 20 min, allowing specific functionalization of the previously masked circular area. This was again followed by a 10 min PBS wash, completing the surface derivatization procedure.

C. Protein Synthesis and MITOMI.

Next a standard 25 µL TNT T7 coupled wheat germ extract mixture (Promega) was prepared and spiked with 1 µL tRNALys-bodipy-fl (Promega) and 2 µL of plasmid DNA template coding for the appropriate protein (HuR, HuD or Gus). The mixture was immediately loaded into the device and flushed for 5 min, after which the chamber valves were opened allowing for dead end filling of the chambers with wheat germ extract. The chamber valves were again closed and flushing continued for an additional 5 min. Next the segregation valves separating each unit cell were closed, followed by opening of the chamber valves allowing for equilibration of the unit cell by diffusion. The entire device was heated to 30° C. on a temperature controlled microscope stage and incubated for up to 90 min to complete protein synthesis, binding of protein to the surface bound biotinylated-5-histidine antibody, solvation of target RNA, and equilibration of proteins and target RNA. MITOMI was then performed by closing the "button" membrane as well as the chamber valves allowing trapping surface-bound complexes while expelling any solution phase molecules. Radial closure prevents solvent pockets from forming between the two interfaces and effectively creates zero dead volume while preserving the equilibrium concentrations of the molecular interactions to be detected. This was followed by a 5 min PBS wash to remove untapped unbound material. The device was then imaged on a modified array WoRxe (AppliedPrecision) microarray scanner to detect protein synthesis and the trapped molecules.

D. Image and Data Analysis.

All images were analyzed with GenePix3.0 (Molecular Devices). For each experiment, an image was taken after MITOMI and the final PBS wash. This was used to determine the concentration of surface bound protein (FITC channel) as well as surface bound target RNA (Cy3 channel). Each unit cell generated a single data point that consisted of the ratio of median signal of Cy3 to median signal of bodipy; thus, representing the ratio of surface bound RNA to surface bound expressed protein. Data from multiple data points were averaged, and their standard deviations calculated. Results were then normalized to 1. Between 10-20 replicates were included for each probe tested. A control protein, Gus-his (Roche) was included in each experiment and subjected to the same analysis. When present, detected signal with Gus-his was used for background subtraction.

2. For Membrane-Associated Proteins.

Detection of RNA binding by NS4B was done similarly to the process described above except for the following modifications. NS4B was expressed before loading into the microfluidic device by using coupled transcription/translation rabbit reticulocyte system (Promega). 2 µL canine microsomal membranes (Promega) were added to the reaction mixture to allow appropriate protein folding. An NS4B-GFP construct was used, thus eliminating the need for $tRNA_{Lys-bodipy-fl}$ in the reaction mixture. A biotinylated anti-GFP antibody (Abcam) was used to specifically functionalize the protected circular area defined by the button. The protein was anchored to the chip via its interaction with the surface bound anti-GFP antibodies. The surface bound protein and the Cy5-labeled HCV RNA probes were loaded into the chip and allowed to incubate for 5-20 min in a 50 mM Hepes KOH (pH 6.8) buffer. Next, MITOMI was performed followed by a brief wash in Hepes KOH (pH 6.8) buffer. The device was then scanned and results quantified as described above. NS4B-GFP mutants and NS5A(AH)-GFP were assayed the same way. Signal detected with NS5A(AH)-GFP was used for background subtraction.

Screening of Inhibitory Compound Library.

The 1280 compounds of the Lopac library (Sigma) solubilized in Dimethyl sulfoxide (DMSO) were spotted onto epoxy coated glass substrates slide (CEL Associates) using an OmniGrid Micro (GeneMachines) microarrayer and a CMP3B pin (TeleChem International, Inc.) as a microarray. For the primary screen, compounds were spotted at a high concentration (~1 mM) in duplicates. The array was allowed to dry, and was then aligned and bonded to a microfluidic device. Two large devices (2400 unit cells per device) were used for the primary screen. The rest of the procedure was done similarly to the procedure described above (RNA binding assay). In brief, the device was subjected to surface patterning that resulted in a circular area coated with biotinylated anti-GFP antibodies within each unit cell. Next, NS4B-GFP expressed prepared "off chip" using coupled transcription/translation rabbit reticulocyte system (Promega) in the presence of microsomal membranes (Promega) was loaded into the chip and bound to the surface biotinylated anti-GFP antibodies. Cy5-labeled 3' neg terminus RNA probe was then loaded at a concentration of 1.5 nM. Each unit cell was then isolated followed by a 30 min incubation to allow binding of the protein to surface biotinylated anti-GFP antibodies, solvation of library compounds, and equilibration of proteins and target RNA. Next, MITOMI was performed trapping surface-bound complexes while expelling any solution phase molecules. After a brief wash to remove untrapped unbound material, the device was scanned and results analyzed. The ratio of bound RNA to expressed protein was calculated for each data point by measuring the median signal of Cy3 to median signal of bodipy. Results were normalized to signal measured in unit cells containing no inhibitory compound. Greater than 90% inhibition was defined as the cutoff for inhibition in the primary screen. 104 compounds which were above this cutoff and additional 110 yielding ambiguous results were subjected to a secondary screen. This was performed similarly, except that two smaller devices (640 unit cells per each) were used, the spotted compound concentration was 10 fold lower than in the primary screen, and 5 replicates were spotted for each compound. Inhibition greater than 2.5 fold was considered significant. 18 compounds identified in this screen were further analyzed for their antiviral effect on HCV RNA replication.

Determination of IC50 for In Vitro RNA Binding.

For an accurate measurement of IC50s, serial dilutions of the inhibitory compound were loaded onto the microfluidic device by continuous flow while maintaining a steady concentration of the compound in the flow channel. This helped to avoid expected losses of the spotted compounds from incomplete solubilization and/or binding of the compound to PDMS. The experiment was performed essentially as described for the RNA binding assay for transmembrane proteins except that the expressed protein and the Cy5-labeled HCV RNA probes were incubated in the device in the presence of the inhibitory compounds or their absence. IC50s were measured as described in the Statistical Analysis section below.

Expression and Purification of Recombinant NS4B.

GST-NS4B and GST were expressed in *E. coli* BL21 and purified as described elsewhere[11]. NS4B was fused in frame with an N-terminal 6his-MISTIC protein (membrane-integrating sequence for translation of IM protein constructs)[35]. Overnight cultures of *E. coli* transformed with mistic-NS4B plasmid were diluted 1:100 in 400 ml of fresh medium and grown at 37° C. to an OD of 0.8. Isopropyl-β-D-thiogalactopyranoside (IPTG) (Invitrogen) was then added to a final concentration of 0.1 mM. After 3 hours growth at 37° C., cells were pelleted and resuspended in 30 ml lysis buffer (50 mM NaCl, 50 mM Tris HCL (pH8), 100 mM Imidazole, 10 mM Decylmaltoside, Complete EDTA free protease inhibitors (Roche Applied Science)). Cells were lysed by one cycle in a French Press at a pressure of 10,000 psi for 1 minute, followed by centrifugation at 12,000 g for 5 minutes at 4° C. The supernatant was loaded on nickel column (Amersham). Following washes, protein was eluted in a buffer containing 400 mM Imidazole. Glycerol was added at a final concentration of 20% and samples were stored at −20° C. Purification was monitored by SDS-PAGE. Total protein concentration was measured using the RC-DC assay (Bio-Rad). NS4B-mistic was identified by Western blot analyses using monoclonal antibodies against 6-his (Santa Cruz Biotechnology) and NS4B (Virostat). 6his-mistic was expressed and purified in a similar manner.

GST Pull Down Assay.

Similar to a previously described strategy[36], 1 μg of purified GST-NS4B or GST was incubated for an hour at 37° C. in a 50 μl reaction mixture containing [32]P-labeled in vitro transcribed HCV RNA (corresponding to the 3' terminus of the negative viral strand) and binding buffer (10 mM DTT, 10 mM Na HEPES (pH 7.4), 33 mM NaCl, 0.1 mM EDTA, 10 mM MgCl2). 50 μl of tRNA pre-coated glutathione-agarose beads (Sigma) were then added, followed by 1 hour incubation at 4° C. to allow binding of GST to the beads. The beads were then washed three times in binding buffer and bound RNA was measured by liquid scintillation counting of sample aliquots. Control incubations with an RNA probe prepared in the absence of T7 RNA polymerase were used for background subtraction.

RNA Filter Binding Assay.

Assays were performed essentially as described[34]. Briefly, various concentrations of mistic-NS4B protein or mistic control were incubated for 1 hour at 30° C. with 3.3 nM [32]P-labeled in vitro transcribed HCV RNA probe in binding buffer (50 mM HEPES pH 7.0, 50 mM NaCl, 1 mM MgCl2, 10 ng/μl tRNA, and 0.2 mM Decylmaltoside) in a final volume of 40 μl. Membranes were pre-soaked in the binding buffer and assembled in a dot blot apparatus (Schleicher & Schull) from top to bottom as follows: nitrocellulose (Bio-rad), Hybond N+ (Amersham Biosciences), Whatman 3 mm filter paper. The binding reactions were loaded onto the dot-plot apparatus and filtered through the membranes. After washing, the membranes were air-dried and visualized by Phospho-imaging. Results represent percentage of bound RNA calculated by dividing the signal detected in the nitrocellulose membrane by the sum of the signals detected in the nitrocellulose and the Hybond membranes.

Cell Cultures and Electroporation.

Huh-7.5 cells were maintained in Dulbecco's modified minimal essential medium (Gibco) supplemented with 1% L-glutamine (Gibco), 1% penicillin, 1% streptomycin (Gibco), 1× nonessential amino acids (Gibco) and 10% fetal bovine serum (Omega Scientific). Cell lines were passaged twice weekly after treatment with 0.05% trypsin-0.02% EDTA and seeding at a dilution of 1:5. Subconfluent Huh-7.5 cells were trypsinized and collected by centrifugation at 700 g for 5 mM. The cells were then washed three times in ice-cold RNase-free PBS (BioWhittaker) and resuspended at $1.5*10^7$ cells/ml in PBS. Wild type or mutant FL-J6/JFH-5'C19Rluc2AUbi RNA for electroporation was generated by in vitro transcription of XbaI-linearized DNA templates using the T7 MEGAscript kit (Ambion), followed by purification, essentially as described above (In vitro RNA transcription and fluorescent labeling). 5 μg of RNA was mixed with 400 μl of washed Huh-7.5 cells in a 2 mm-gap cuvette (BTX) and immediately pulsed (0.82 kV, five 99 μs pulses) with a BTX-830 electroporator. After a 10 mM recovery at 25° C., pulsed cells were diluted into 10 ml of prewarmed growth medium. Cells from several electroporations were pooled to a common a stock and seeded in 6 well plates ($5*10^5$ cells per well). After 24 hr, medium was replaced and cells were grown in the presence of serial dilutions of the various inhibitory compounds (Sigma) identified in the screen. 17 commercially available compounds, out of the 18 identified, were analyzed. Untreated cells were used as a negative control for water soluble compounds. For compounds solubilized in DMSO, untreated cells were grown in the presence of corresponding concentrations of the solvent as a negative control. Medium was changed daily. After 72 hr of treatment, cells were subjected to an alamar blue based viability assay and luciferase assay.

Viability Assay.

Following 72 hrs of treatment, cells were incubated for 3 hrs at 37° C. in the presence of 10% Alamar Blue reagent (TREK Diagnostic Systems). Plates were then scanned and fluorescence was detected by using FLEXstation II 384 (Molecular Devices, Inc.). Depending on the inhibitory compound's solvent, water (other compounds not in DMSO) or DMSO (D042, (allylnorapomorphine), R-108, Tropicamide, Thalidomide, Glyburide, LFM-A13), signal was normalized relatively to untreated samples or samples grown in the presence of DMSO, respectively.

Luciferase Assay.

Viral RNA replication was determined using *Renilla* luciferase assay (Promega). The same samples subjected to the viability assay described above were analyzed in this assay. According to the manufacturer's protocol, cells were washed with ice cold PBS and scraped off the plate into 250 μl of ice-cold *Renilla* lysis buffer. 20 μl of the cell lysates were then loaded onto 96 well plates. 100 μl of the *Renilla* luciferase assay buffer containing the assay substrate were injected and luciferase activity was measured using a Berthold LB 96 V luminometer. As above, signal was normalized relative to untreated samples or samples grown in the presence of the corresponding concentration of DMSO.

Luciferase activity detected in samples treated with 100 u/ml Interferon alpha B2 (PBL biomedical labs) was used as a positive control, demonstrating three log reduction at 72 hr treatment. The experiment was repeated four times, each time with triplicates. IC50s were measured by fitting data to a three parameter logistic curve using the formula $Y=a+(b-a)/(1+10^{(X-c)})$ (BioDataFit, Chang Bioscience, Inc).

Real-Time PCR.

$5\times10^4$ Huh7.5 ells were infected with cell culture-grown HCV titered at $1.4\times10^4$ TCID50/ml, as described[29]. 2 hours after infection, cells were washed three times in culture medium. Cells were then treated daily with various concentrations of clemizole. After 72 hours, samples were subjected to the viability assay described above, following which TRIzol Reagent (Invitrogen) was added and total cell RNA was extracted in triplicates according to the manufacturer's instructions. Reverse transcription was then performed using random hexamers and Superscript II reverse transcriptase (Invitrogen, Carlsbad, Calif.). Real-time PCR was performed on the resulting cDNA to quantify the amounts of HCV and actin RNA (in separate reactions) in each sample. Standards were made using an in vitro-transcribed HCV RNA and human actin standard (Applied Biosystems, Foster City, Calif.). HCV was quantified using primers AGAGCCAT-AGTGGTCT (SEQ ID No: 17) and CCAAATCTCCAG-GCATTGAGC (SEQ ID No: 18) and probe 6-carboxyfluo-rescein-CACCGGAATTGCCAGGACGACCGG-6 (SEQ ID No: 19) carboxytetramethylrhodamine. Actin was quantified using beta-actin control reagents (Applied Biosystems) according to the manufacturer's instructions. HCV RNA level was adjusted to actin level and normalized relative to untreated samples.

Selection of Resistant Mutants.

Established HCV replicons-harboring cells and Huh7 cells electroporated de novo with a genotype 1b subgenomic HCV replicon (Bart 79I)[30] were passaged in the presence of neomycin and increasing concentrations of clemizole (1-16 µM). Colonies that were able to grow in the presence of the compound were isolated and propagated for 5-10 passages. Eleven colonies (out of ~60) survived the passages and were subjected to sequence analysis, as previously described[11].

Whole Cell RNA Electroporation.

Whole cell RNA was extracted from clemizole-resistant replicon clones and from untreated replicon cells using TRIzol reagent (Invitrogen). Equal amounts of whole cell RNA (50 µg) were electroporated into Huh7.5 cells as described above. Cells were grown under G418 selection in the presence or absence of clemizole for 3 weeks. The number of colonies was determined using Image J (NIH) following fixation and staining with Crystal violet.

Statistical Analysis.

Dissociation equilibrium constants were determined by fitting data to the equation describing equilibrium binding; $Y=a*X/(b+X)$ (a and b represent maximum binding and Kd, respectively) by nonlinear least squares regression fitting (BioDataFit, Chang Bioscience). IC50s were measured by fitting data to a three parameter logistic curve using the formula $Y=a+(b-a)/(1+10^{(X-c)})$ (a, b and c represent minimum binding, maximum binding and logEC50, respectively) (BioDataFit, Chang Bioscience, Inc).

Additional Information.

Calibration curve: To confirm adequate solubilization of the dried spotted RNA probes and to exclude the possibility that a large fraction of the solvents stick to the polydimethylsiloxane (PDMS) composing the microfluidic device, a calibration curve was generated. Known concentrations of soluble labeled RNA probes were loaded into the device by continuous flow and mean values of Cy3 signal from multiple unit cells were averaged. Based on this curve, the actual concentration of target RNA sequences used in the assay was calculated. On average, the actual assayed concentration was 0.55±0.02 of the spotted one. Of note, a similar factor (0.57) was calculated based on the ratio between a typical print volume and unit cell volume. All the presented data were adjusted according to this factor.

RNA binding experiment with high ionic strength buffer: The ionic strength of the buffer used in an RNA binding experiment may have an effect on the protein-RNA interaction. To confirm that the high affinity interactions detected in the RNA binding assay are not a result of enhancement of electrostatic interactions due to a low ionic strength buffer, RNA binding experiments of NS4B were performed by microfluidics using high (150 mM) ionic strength conditions. RNA binding by NS4B in the presence of PBS (137 mM NaCl, 2.7 mM KCl, 10 mM $Na_2HPO_4$, 2 mM $KH_2PO_4$) or 150 mM Hepes was similar to that detected with 50 mM Hepes buffer, commonly used for RNA binding assays by others (*J Biol Chem* 280, 36417-36428 (2005) and *J Virol* 80, 9865-9875 (2006), each of which is incorporated herein by reference). The Kd of NS4B binding to the 3' terminus of the HCV negative strand RNA in the high ionic strength conditions was measured at 6.6±3.3 nM (vs. a Kd of 3.4±1.0 nM in the presence of low (50 mM) ionic strength conditions). These results suggest that there is only a small electrostatic component to the observed RNA-binding.

Figure 14:
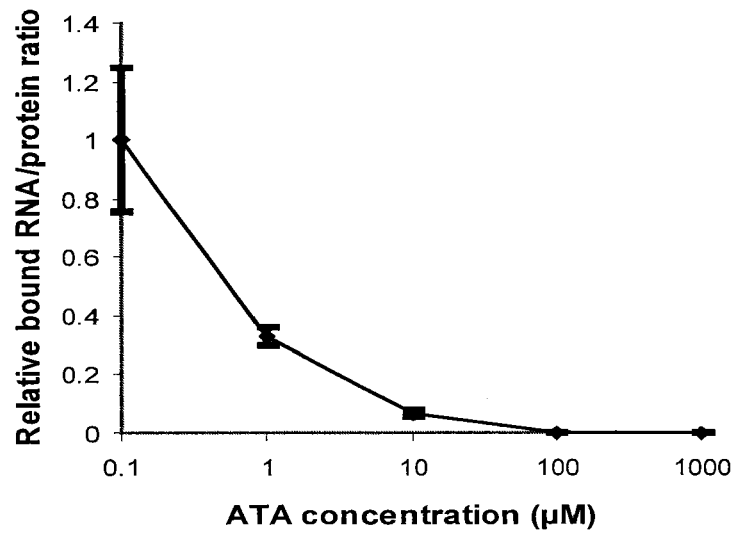
FIG. 14 illustrates results that show that ATA inhibits RNA binding by NS4B in a dose dependent manner.

ATA inhibits RNA binding by NS4B in a dose-dependent manner: Prior to the library screen, it was determined that HCV RNA binding by NS4B can be inhibited pharmacologically. Aurintricarboxilic acid (ATA) is a compound known to inhibit interactions of proteins with nucleic acids (*Nucleic acids res* 4, 3055-3064 (1977), which is incorporated herein by reference). Thus, ATA should inhibit binding of NS4B to HCV RNA. To test this hypothesis, the NS4B RNA binding assay was repeated in the presence of increasing concentrations of ATA. Indeed, ATA was found to inhibit binding of HCV RNA by NS4B in a dose-dependent manner, with an IC 50 of 0.49±0.01 µM (p value—0.0003) (FIG. 14).

Consistent with this result, ATA was one of the 18 compounds identified in the screen of the LOPAC library. Because this compound had been previously shown to inhibit the RNA binding activity of NS4B, this compound served as a useful internal control for the validity of the screen.

Specificity of hits identified in the small molecule screen: To determine the specificity of the hits identified in the small molecule screen, the HuR protein (one of the human RNA binding protein used to validate our RNA binding assay) was selected. Interestingly, other than binding to its target RNA sequence, 4A (FIG. 12), this protein has been previously shown by others (*Virology* 274, 378-390 (2000), which is incorporated herein by reference) to bind the 3' terminus of the negative HCV strand. Binding of HuR to the consensus 4A RNA sequence was tested in the presence of the inhibitory molecules shown to inhibit RNA binding by NS4B. No inhibitory effect on RNA binding was detected with the majority of the hits, including clemizole, at a concentration of 0.1 mM. Similarly, 0.1 mM of the identified compounds didn't have an inhibitory effect on binding of HuR to the 3' terminus of the negative HCV RNA strand. In contrast to the other hits, ATA, known as a non-specific inhibitor of protein-nucleic acids interactions, significantly inhibited HuR binding to both 4A and 3' terminus of the negative HCV strand. These results support the conclusion that the identified hits including clemizole are indeed specific to RNA binding by NS4B.

Figure Captions for Example 1

Figure 4A:
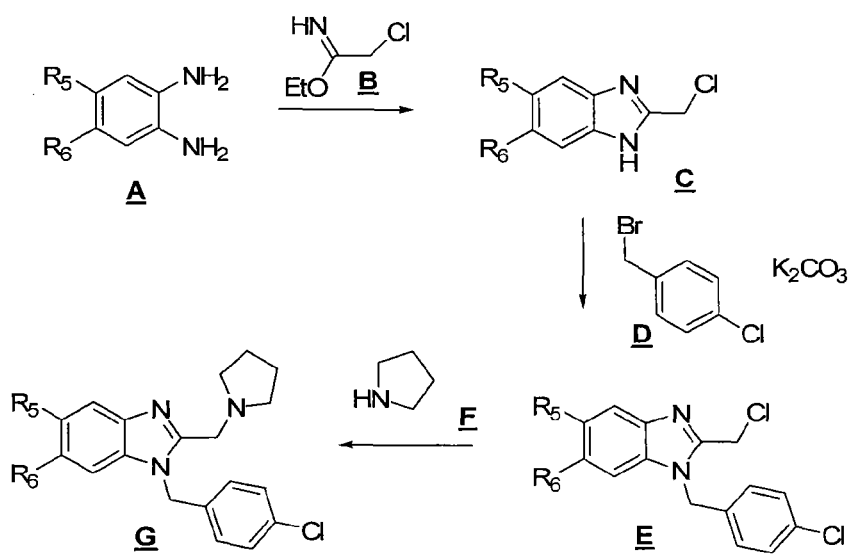
FIG. 4A illustrates an embodiment of a general method of synthesizing 5,6-disubstituted clemizole compounds.
Figure 4B:
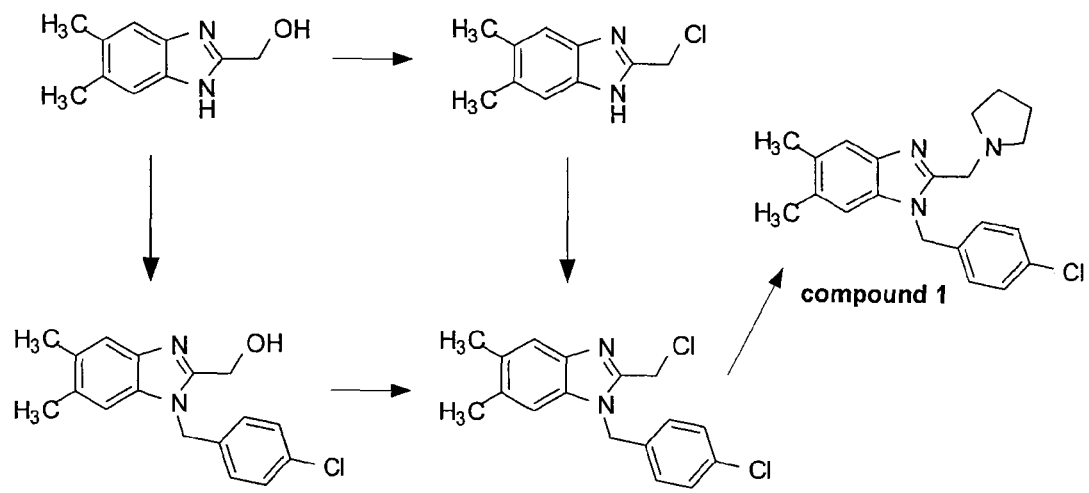
FIGS. 4B and 4C illustrate embodiments of synthesizing two 5,6-disubstituted clemizole compounds.
Figure 4C:
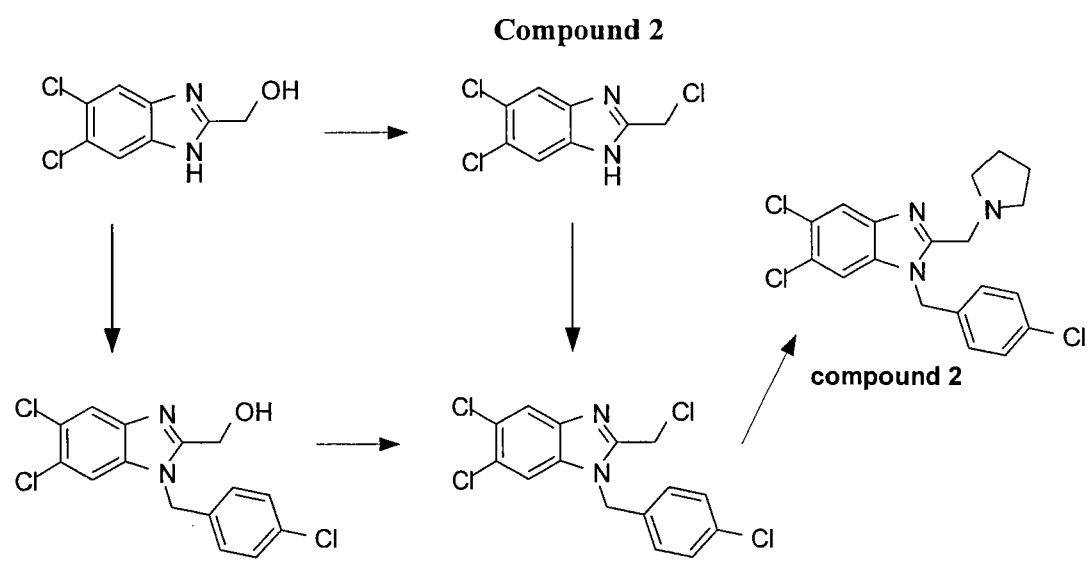

FIG. 4A illustrates an embodiment of a general method of synthesizing 5,6-disubstituted clemizole compounds. FIGS. 4B and 4C illustrate embodiments of synthesizing two 5,6-disubstituted clemizole compounds.

FIGS. 5a-5d illustrate results from protein-RNA interactions measured on a microfluidic platform. FIG. 5a is a table that illustrates the target RNA sequences used to study binding of HuD to RNA and comparison of Kd values measured using microfluidic affinity analysis to values previously measured by gel shift assay[21,22]. ND=not determined. FIG. 5b illustrates a binding curve of HuD to increasing concentration of AU3 (●) and AU3 mutant (Δ) RNA, as determined in the microfluidic affinity assay. Normalized mean values for 10-20 replicates measured in two independent experiments are shown for each graph. Error bars represent standard deviation. FIG. 5c is a digital image of fluorescent images from microfluidic chip: Left: NS4B-GFP and NS5A(AH)-GFP were anchored to the microfluidic device surface via its interaction with anti-GFP; Middle: An RNA probe corresponding to the 3' terminal region of the negative viral strand was labeled with Cy5 and incubated with the proteins on the device. Cy5 signal representing bound RNA is shown following a brief wash; Right: An overlay of the Cy5 signal and GFP signal representing bound RNA to protein ratio. FIG. 5d is a graph illustrating the in vitro Binding curve of NS4B to serial dilutions of the RNA probe.

FIGS. 6a and 6b illustrate results that show that NS4B binds specifically to the 3' terminus of the HCV negative strand RNA. FIG. 6a illustrates four HCV probes designed for embodiments of the present disclosure. 5' UTR (untranslated region) pos and 3' UTR pos corresponded to the 5' UTR and 3' UTR sequences of the positive viral strand respectively and 5' negative terminus and 3' negative terminus, corresponded to the 5' and 3' terminal regions of the negative strand, respectively. The position of these sequences with respect to the HCV open reading frame (ORF) is shown. FIG. 6b is a graph that illustrates the fractional binding of NS4B to equimolar concentrations of the four HCV probes and to a non-HCV RNA (delta virus RNA) probe. The 3' terminus of the negative genome strand is favored by >5×.

FIGS. 7a-7d illustrate the identification of RNA binding domains within NS4B and results. FIG. 7a illustrates that arginine-rich sequences known to confer RNA binding were found in viral and bacteriophage proteins[9,25,26]. Elements in the terminal loop of NS4B that conform quite nicely with arginine-rich-like motifs are shown at the bottom. Proteins listed are HIV Rev and Tat[25]; λ, Φ21 and P22 bacteriophage antiteuninator N proteins[25]; triple gene block protein 1 (TGBp1) of the bamboo mosaic virus (BaMV)[26] and poliovirus 2C[9]. FIG. 7b illustrates that positively charged amino acids (R and RR, bold and underlined) within the primary sequence of NS4B (genotype 1a). FIG. 7c is a schematic diagram indicating predicted transmembrane and intracellular domains of NS4B. Conserved positively charged amino acids in the C-terminal segment of NS4B are shown as R or RR. FIG. 7d is a graph that illustrates that arginine residues mediate RNA binding by NS4B. Binding of wild type NS4B-GFP, RRa and RRb NS4B-GFP mutants and NS5A(AH)-GFP to the 3' terminus of the negative viral RNA strand (1.5 nM) was determined by microfluidic affinity analysis. Bars represent standard deviation.

FIGS. 8a-8d illustrates results that a small molecule screen reveals that clemizole hydrochloride inhibits RNA binding by NS4B and in vivo HCV RNA replication. FIG. 8a is a digital image of the first screen which represented a low stringency measurement of inhibition of 1280 compounds, where the latter were categorized as having high (light gray), ambiguous (black), or no (gray) inhibition. Based on the initial screen 214 compounds were then measured again with higher stringency and with greater number of replicates and the best 18 inhibitors were tested for their ability to inhibit HCV replication via an in vivo cellular assay. FIG. 8b illustrates a graph showing in vitro inhibition of NS4B-RNA binding by the top 18 small molecules. FIG. 8c is a graph showing in vivo HCV luciferase-linked reporter cellular assay showing that clemizole inhibits HCV replication (left axis, bottom line ♦) with no measurable toxicity to the cell as measured by Alamar Blue (right axis, top line □). FIG. 8d is a graph showing in vitro NS4B-RNA binding: inhibition curve of clemizole.

FIGS. 9a-9e illustrate results corresponding to the clemizole-resistant mutant data. Replicon cells were passaged in the presence of clemizole and individual colonies were isolated, propagated and the HCV genomes harbored within were subjected to sequence analysis. FIG. 9a is a schematic diagram indicating predicted transmembrane and intracellular segments of NS4B. Conserved positively-charged amino acids are shown as R or RR. The clemizole resistant mutation, W55R, is shown as W R. FIG. 9b is a graph that illustrates HCV replication in Huh7.5 cells electroporated with 50 μg of whole cell RNA extracted from cells harboring either wild-type or the W55R mutant clone, followed by growth in the absence (white bars) or presence (grey bars) of 10 μM clemizole. Results represent relative numbers of colonies obtained compared to each corresponding untreated control. FIG. 9c illustrates the HCV replication assays initiated by electroporation of in vitro transcribed luciferase reporter-linked wild-type or W55R mutant HCV RNA genomes performed in the absence (white bars) or presence (grey bars) of 10 μM clemizole. Results represent replication level of each genome relative to its untreated level. FIG. 9d illustrates HCV RNA binding of wild type NS4B and the W55R NS4B mutant as measured in vitro by microfluidics in the presence of 10 nM clemizole (grey bars) and its absence (white bars). FIG. 9e illustrates in vitro binding curves of W55R NS4B mutant (solid line, ○) and wild type NS4B (broken line, ▲) to serial dilutions of the RNA probe.

FIGS. 10a-10c illustrate schematics of the microfluidic based RNA binding assay. 3 individual unit cells out of hundreds/thousands per microfluidic device) are shown in this scheme. FIG. 10a illustrates compartments and micromechanical valves. A valve is created where a control channel crosses a flow channel. The resulting thin membrane in the junction between the two channels can be deflected by hydraulic actuation. Using multiplexed valve systems allows a large number of elastomeric microvalves to perform complex fluidic manipulations within these devices.

FIG. 10a illustrates the experimental protocol. ● on top represents Cy3 labeled RNA probe. ○ on bottom represents surface bound bodipy-labeled protein.

FIG. 10b(1) illustrates the target RNA sequences labeled with Cy3 were spotted onto an epoxy-coated slide as a microarray.

FIG. 10b(2) illustrates the microfluidic device was aligned and bonded to the slide allowing contact of each spot in the array with a unit cell in the device. The device was subjected to surface patterning that resulted in a circular area coated with biotinylated anti-histidine antibodies within each unit cell (see Supplemental FIG. 10c). The "neck valve" separating the flow channels from the RNA chamber remained closed during this process.

FIG. 10b(3) illustrates that the device was then loaded with in vitro transcription/translation mixture containing DNA template encoding a his-labeled protein. Bodipy-labeled tRNALys was added for protein labeling.

FIG. 10b(4) illustrates that each unit cell was then isolated by the control of two "sandwich" micromechanical valves.

FIG. 10b(5) illustrates that the "neck valve" was opened forming a single compartment by combining the flow channel compartment with the RNA chamber. This was followed by an incubation to allow protein synthesis, binding of the synthesized protein to the surface biotinylated anti-his antibodies, solvation of target RNA, and equilibration of proteins and target RNA.

FIG. 10b(6) illustrates that MITOMI was then performed by actuation of a "button" membrane trapping surface-bound complexes while expelling any solution phase molecules.

FIG. 10b(7) illustrates that the "sandwich" valves were opened followed by a brief wash to remove untrapped unbound material.

FIG. 10b(8) illustrates that the "button" membrane was opened and the device was scanned by an array scanner. Trapped RNA molecules and expressed protein were detected. The ratio of bound RNA to expressed protein was calculated for each data point by measuring the median signal of Cy3 to median signal of bodipy (represented by ○ on the bottom).

FIG. 10c illustrates surface patterning. FIG. 10c(1) illustrates that the accessible surface area was derivatized by flowing a solution of biotinylated BSA (●) through all flow channels. FIG. 10c(2) illustrates that a Neutravidin solution (●) was loaded. FIG. 10c(3) illustrates that the "button" membrane was activated. FIG. 10c(4) illustrates all remaining accessible surface area except for a circular area of 60 μm masked by the button was passivated with biotinylated solution (●) 5) the "button" membrane was opened 6) a solution of biotinylated-antibody (●) was loaded allowing specific functionalization of the previously masked circular area. FIG. 10c(7) illustrates that in vitro expressed protein (●) was loaded into the device and bound to the biotinylated-antibody coating the discrete circular area. Each of the described steps was followed by a PBS wash.

FIGS. 11a-11b illustrate graphs showing the signal to noise ratio in our RNA binding assay. FIG. 11a is a graph that illustrates the binding of HuD-his (●) and Gus-his (□) to increasing concentration of the AU3 RNA probe. Representative experiments are shown. Bars represent standard deviation. FIGS. 11a and 11b are graphs that illustrates the binding of NS4B-GFP-microsomal membranes (mm) (●, continuous line) and NS5A(AH)-GFP-mm (■, dashed line) to increasing concentrations of the 3' terminus of the negative strand. The grey striped column represents the range of probe concentration for which the signal to noise ratio was the greatest. All of our reported experiments were performed within this range. Representative experiments are shown. Bars represent standard deviation.

FIGS. 12a-12c illustrate results from the microfluidics-based analysis of RNA binding by another human protein from the ELAV-like family, HuR (ELAV L1). FIG. 12a illustrates the target RNA sequences used to study binding of HuR to RNA and the phenotype demonstrated by conventional RNA binding methods (*EMBO J.* 16, 2130-2139 (1997), which is incorporated herein by reference).

FIG. 12b illustrates that HuR binds RNA by microfluidics. A microarray of Cy3-labeled target RNA sequences was used to program a microfluidic device, and binding of bodiby-labeled proteins expressed on the device to the RNA sequences was assayed. Results represent the ratio of bound RNA (median Cy3 signal) to expressed protein (median bodipy signal). Normalized mean values for 10-20 replicates measured in two independent experiments are shown. Error bars represent standard deviation. The grey bars represent binding of HuR-his and the clear bars that of Gus-his, used as a negative control.

FIG. 12c illustrates that HUR binding is not affected by the 5 most active compounds, but is affected by ATA. We tested binding of HUR to its 4A RNA target in the presence and absence of NS4B RNA binding inhibitors. Data represent mean value of 10-20 replicates and bars represent standard deviation.

FIGS. 13a-13c illustrate results from the binding of NS4B to HCV RNA by conventional methods. NS4B was expressed in *E. coli* fused to GST or mistic-6his and purified. FIG. 13a illustrates binding activity of GST-NS4B and GST to $^{32}$P-labeled RNA probe corresponding to the 3' terminus of the negative viral strand, as measured by a GST pull down assay. FIG. 13b illustrates nitrocellulose membranes from a representative RNA filter binding assay. $^{32}$P-labeled HCV RNA probe bound to 10 mM (left panel) or 2 mM (right panel) mistic-NS4B or mistic control is shown. FIG. 13c illustrates the percentage of bound RNA to mistic-NS4B and mistic proteins at protein concentrations of 10 mM (grey bars) and 2 mM (white bars), as measured by a filter binding assay.

FIG. 14 illustrates results that show that ATA inhibits RNA binding by NS4B in a dose dependent manner. A dose response curve of RNA binding by NS4B in the presence of increasing concentrations of ATA, as measured by microfluidics. The Y category is bound RNA to protein ratio relative to binding in the absence of ATA. The X category is ATA concentration (μM). Data were fit to a 3 parameter logistic curve using the formula Y=a+(b-a)/(1+10^(X-c)) (BioDataFit, Chang Bioscience) and IC50 was calculated at 0.49±0.01 μM (p value—0.0003).

FIG. 15 illustrates results that show that clemizole inhibits HCV replication by real-time PCR assays. Real-time PCR assay of HCV replication levels showing that clemizole inhibits HCV replication (left axis ♦ (bottom curve)) with no measurable toxicity to the cell (right axis, ■ (top curve)).

FIG. 16 is a digital image that shows that the RRb mutation decreased replication by ~45 fold, and the replicon harboring the RRa mutation was completely defective in RNA replication.

FIG. 17A shows a chemical structure of clemizole hydrochloride.

FIG. 17B shows a chemical structure of a clemizole derivative molecule with increased potency and efficacy.

FIG. 17C illustrates a graph that shows in vitro inhibition curve of Clemizole derivative molecule (●) and the parental Clemizole hydrochloride compound (□), as measured by microfluidics (bound RNA/protein ratio vs compound concentration (μM)).

FIG. 17D illustrates a graph that shows a dose response curve of HCV replication in the presence of increasing concentrations of Clemizole derivative molecule (●) and the parental Clemizole hydrochloride compound (□), as measured by a real-time PCR assay in HCV-infected cells (relative viral replication vs compound concentration (μM)).

References, each of which is incorporated herein:
1. Liang, T. J., Rehermann, B., Seeff, L. B. & Hoofnagle, J. H. Pathogenesis, natural history, treatment, and prevention of hepatitis C. *Ann Intern Med* 132, 296-305 (2000).
2. Reed, K. E. & Rice, C. M. Overview of hepatitis C virus genome structure, polyprotein processing, and protein properties. *Curr Top Microbiol Immunol* 242, 55-84 (2000).

3. Rice, C. M. Flaviviridae: The viruses and their replication. In B. N. Fields, D. M. Knipe, and P. M. Howley (ed.), Fields Virology. (Lippincott-Raven Publications, Philadelphia, Pa., 1996).
4. Egger, D. et al. Expression of hepatitis C virus proteins induces distinct membrane alterations including a candidate viral replication complex. *J Virol* 76, 5974-5984 (2002).
5. Elazar, M., Liu, P., Rice, C. M. & Glenn, J. S. An N-terminal amphipathic helix in hepatitis C virus (HCV) NS4B mediates membrane association, correct localization of replication complex proteins, and HCV RNA replication. *J Virol* 78, 11393-11400 (2004).
6. Gosert, R. et al. Identification of the hepatitis C virus RNA replication complex in Huh-7 cells harboring subgenomic replicons. *J Virol* 77, 5487-5492 (2003).
7. El-Hage, N. & Luo, G. Replication of hepatitis C virus RNA occurs in a membrane-bound replication complex containing nonstructural viral proteins and RNA. *J Gen Virol* 84, 2761-2769 (2003).
8. Kusov, Y. Y., Probst, C., Jecht, M., Jost, P. D. & Gauss-Müller, V. Membrane association and RNA binding of recombinant hepatitis A virus protein 2C. *Arch Virol* 143, 931-944 (1998).
9. Rodríguez, P. L. & Carrasco, L. Poliovirus protein 2C contains two regions involved in RNA binding activity. *J Biol Chem* 270, 10105-10112 (1995).
10. Echeverri, A. C. & Dasgupta, A. Amino terminal regions of poliovirus 2C protein mediate membrane binding. *Virology* 208, 540-553 (1995).
11. Einav, S., Elazar, M., Danieli, T. & Glenn, J. S. A nucleotide binding motif in hepatitis C virus (HCV) NS4B mediates HCV RNA replication. *J Virol* 78, 11288-11295 (2004).
12. Overington J P, A.-L. B., Hopkins A L. How many drug targets are there? *Nat Rev Drug Discov* 5, 993-996 (2006).
13. Lundin, M., Monné, M., Widell, A., Von Heijne, G. & Persson, M. A. A. Topology of the membrane-associated hepatitis C virus protein NS4B. *J Virol* 77, 5428-5438 (2003).
14. Hadd A G, R. D., Halliwell J W, Jacobson S C, Ramsey J M. Microchip device for performing enzyme assays. *Anal Chem* 69, 3407-3412 (1997).
15. Maerkl, S. J. & Quake, S. R. A systems approach to measuring the binding energy landscapes of transcription factors. *Science* 315, 233-237 (2007).
16. Toepke, M. W. & Beebe, D. J. PDMS absorption of small molecules and consequences in microfluidic applications. *Lab on a chip* 6, 1484-1486 (2006).
17. Lee, J. N., Park, C. & Whitesides, G. M. Solvent compatibility of poly(dimethylsiloxane)-based microfluidic devices. *Anal chem* 75, 6544-6554 (2003).
18. Whitesides, G. M. The origins and the future of microfluidics. *Nature* 442, 368-373 (2006).
19. Kang, L., Chung, B. G., Langer, R. & Khademhosseini, A. Microfluidics for drug discovery and development: from target selection to product lifecycle management. *Drug discovery today* 13, 1-13 (2008).
20. Myer, V. E., Fan, X. C. & Steitz, J. A. Identification of HuR as a protein implicated in AUUUA-mediated mRNA decay. *EMBO J.* 16, 2130-2139 (1997).
21. Park, S., Myszka, D. G., Yu, M., Littler, S. J. & Laird-Offringa, I. A. HuD RNA recognition motifs play distinct roles in the formation of a stable complex with AU-rich RNA. *Mol Cell Biol* 20, 4765-4772 (2000).
22. Park-Lee, S., Kim, S. & Laird-Offringa, I. A. Characterization of the interaction between neuronal RNA-binding protein HuD and AU-rich RNA. *J Biol Chem* 278, 39801-39808 (2003).
23. Glenn, J. S., Taylor, J. M. & White, J. M. In vitro-synthesized hepatitis delta virus RNA initiates genome replication in cultured cells. *J Virol* 64, 3104-3107 (1990).
24. Glenn, J. S., Watson, J. A., Havel, C. M. & White, J. M. Identification of a prenylation site in delta virus large antigen. *Science* 256, 1331-1333 (1992).
25. Burd, C. G. & Dreyfuss, G. Conserved structures and diversity of functions of RNA-binding proteins. *Science* 265, 615-621 (1994).
26. Wung, C. H. et al. Identification of the RNA-binding sites of the triple gene block protein 1 of bamboo mosaic potexvirus. *J Gen Virol* 80 (Pt 5), 1119-1126 (1999).
27. Spångberg, K., Wiklund, L. & Schwartz, S. HuR, a protein implicated in oncogene and growth factor mRNA decay, binds to the 3' ends of hepatitis C virus RNA of both polarities. *Virology* 274, 378-390 (2000).
28. Tscherne, D. M. et al. Time- and temperature-dependent activation of hepatitis C virus for low-pH-triggered entry. *J Virol* 80, 1734-1741 (2006).
29. Lindenbach, B. D. et al. Complete replication of hepatitis C virus in cell culture. *Science* 309, 623-626 (2005).
30. Elazar, M. et al. Amphipathic helix-dependent localization of NS5A mediates hepatitis C virus RNA replication. *J Virol* 77, 6055-6061 (2003).
31. Tong, X. et al. Identification and analysis of fitness of resistance mutations against the HCV protease inhibitor SCH 503034. *Antiviral Res* 70, 28-38 (2006).
32. Dimitrova, M., Imbert, I., Kieny, M. P. & Schuster, C. Protein-protein interactions between hepatitis C virus nonstructural proteins. *J Virol* 77, 5401-5414 (2003).
33. Blight, K. J., Kolykhalov, A. A. & Rice, C. M. Efficient initiation of HCV RNA replication in cell culture. *Science* 290, 1972-1974 (2000).
34. Huang, L. et al. Hepatitis C virus nonstructural protein 5A (NS5A) is an RNA-binding protein. *J Biol Chem* 280, 36417-36428 (2005).
35. Roosild, T. P. et al. NMR structure of Mistic, a membrane-integrating protein for membrane protein expression. *Science* 307, 1317-1321 (2005).
36. Schilders, G., Raijmakers, R., Raats, J. M. H. & Pruijn, G. J. M. MPP6 is an exosome-associated RNA-binding protein involved in 5.8S rRNA maturation. *Nucleic acids res* 33, 6795-6804 (2005).

Example 2

Figure 2:
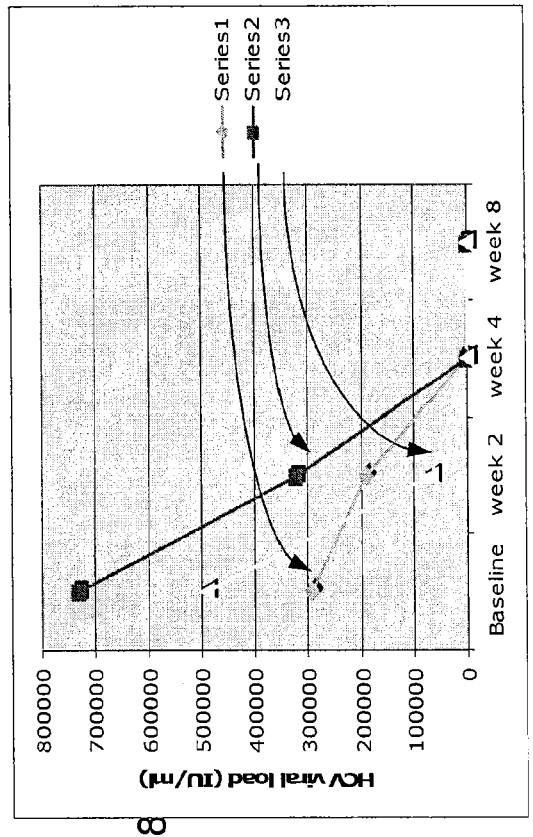
FIG. 2 illustrates baseline characteristics and serial HCV viral loads in the serum of patients.

To demonstrate the in vivo efficacy of clemizole in treating patients infected with HCV, 3 patients chronically-infected with HCV were treated with clemizole 100 milligrams, p.o. BID for 8 weeks. After the first four weeks of clemizole monotherapy, pegylated interferon was added. The baseline characteristics and serial HCV viral loads in the serum are presented in FIG. 2. HCV viral loads decreased significantly on treatment with clemizole alone, becoming completely, or nearly, undetectable after 4 weeks of treatment. These results demonstrate that clemizole is effective in treating patients infected with HCV.

Example 3

FIG. 4A illustrates a method that could be used to produce 5-6-disubstituted chemizole compounds. In particular, the methods could produce Compound 1 (disubstituted with methyl groups at the 5 and 6 positions (FIG. 4B)) and Compound 2 (disubstituted with Cl groups at the 5 and 6 positions (FIG. 4C)).

The disubstituted clemizole can be synthesized by: condensation of 4,5-disubstituted-benzene-1,2-diamine (A) and 2-chloro-acetimidic acid ethyl ester (B) yields 2-chloromethyl-5,6-disubstituted-1H-benzoimidazole (C); followed by alkylation with 1-bromomethyl-4-chloro-benzene (D) affords 1-(4-chloro-benzyl)-2-chloromethyl-5,6-disubstituted-1H-benzoimidazole (E); and the final alkylation of 1-(4-chloro-benzyl)-2-chloromethyl-5,6-disubstituted-1H-benzoimidazole (E) with pyrrolidine yields the 5,6-disubstituted Clemizole (1-(4-Chloro-benzyl)-5,6-disubstituted-2-pyrrolidin-1-ylmethyl-1H-benzoimidazole) (G).

Example 4

Table 3 shown below illustrates the effects of clemizole analogs on HCV RNA replication (AV) and cell viability (Viab) using the Luciferase and Alamar Blue assays described herein. Compound activities were measured at two concentrations to determine whether the effects were dose-dependent. Numerical values represent the percent of normal activity (either viral replication or cell viability) remaining after compound treatment; these values have also been binned to provide a rough measure of relative activity.

The percent inhibition relative to no drug control for each compound was determined at two concentrations of compound, 5 micromolar and 10 micromolar, and recorded in the table. In addition, these percentages were converted to a scoring system as follows: "−"=90-100% residual activity (i.e., no effect); "+"=60-90% residual activity; "++"=30-60% residual activity; "+++"=0-30% residual activity. Thus a compound scored as +++ in the replication assay has greater antiviral activity (AV) than a compound scored as +. Similarly, a compound scored as + in the cell metabolism assay (Viab=viability) is less toxic than a compound scored as +++.

The results demonstrate that H1 antagonism can be separated from antiviral activity, and that compounds lacking the tertiary amine group required for H1 activity can show enhanced antiviral effects relative to clemizole; numerous compounds show a strong separation between antiviral activity and impact on cell viability, supporting the conclusion that the former activity results from specific inhibition of NS4B/RNA binding; and many compounds demonstrate dose-dependent activity, as inhibition of HCV RNA replication is more pronounced at the higher (10 uM) concentration. Taken together, these structure-activity relationships demonstrate that the known and novel analogs of clemizole described herein can prevent HCV replication, and that analogs that lack H1 antagonism (and attendant CNS effects) maintain an acceptable therapeutic ratio.

TABLE 3

| Structure | 5 uM AV | 10 uM Viab | 5 uM AV | 10 uM Viab | 5 uM AV | 10 uM Viab | 5 uM AV | 10 uM Viab |
|---|---|---|---|---|---|---|---|---|
| benzimidazole with pyrrolidinylmethyl and 4-chlorobenzyl | 62 | 107 | 37 | 93 | + | − | ++ | − |
| 5-chloro-2-methyl-1-benzyl-benzimidazole | 87 | 99 | 60 | 94 | + | − | + | − |
| 5,6-dimethyl-1-(2,4-dichlorobenzyl)-benzimidazole | 30 | 83 | 8 | 70 | +++ | + | +++ | + |
| 1-(4-bromobenzyl)-benzimidazole | 23 | 81 | 8 | 68 | +++ | + | +++ | + |

TABLE 3-continued

| Structure | 5 uM AV | 5 uM Viab | 10 uM AV | 10 uM Viab | 5 uM AV | 5 uM Viab | 10 uM AV | 10 uM Viab |
|---|---|---|---|---|---|---|---|---|
| 2-methyl-1-(4-bromobenzyl)benzimidazole | 3 | 54 | 2 | 51 | +++ | ++ | +++ | ++ |
| 2-(hydroxymethyl)-1-(4-bromobenzyl)benzimidazole | 50 | 97 | 28 | 90 | ++ | − | +++ | − |
| 1-(4-methoxycarbonylbenzyl)benzimidazole | 74 | 101 | 54 | 96 | + | − | ++ | − |
| 1-(4-tert-butylbenzyl)benzimidazole | 30 | 87 | 12 | 76 | +++ | + | +++ | + |
| 1-(4-methylbenzyl)benzimidazole | 49 | 99 | 23 | 84 | ++ | − | +++ | + |
| 1-(4-methoxybenzyl)benzimidazole | 70 | 98 | 58 | 100 | + | − | ++ | − |

Key:
− 90-100% residual activity (no effect)
+ 60-90% residual activity
++ 30-60% residual activity
+++ 10-30% residual activity It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

```

What is claimed is:

1. A pharmaceutical composition for treating a host having a viral infection for a virus from the Flaviviridae family of viruses, comprising an inhibiting agent, wherein the inhibiting agent has the following structure:

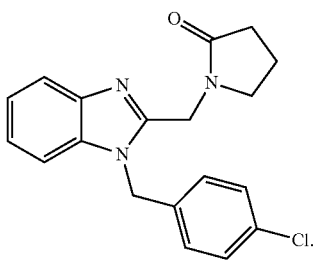 [SMILES: O=C1CCCN1Cc1nc2ccccc2n1Cc1ccc(Cl)cc1]

2. The pharmaceutical composition of claim 1, further comprising a second agent for treating the viral infection.

3. The pharmaceutical composition of claim 2, wherein the second agent is selected from the group consisting of: an anti-HCV therapeutic agent, an HCV NS3 protease inhibitor, an HCV NS5B RNA-dependent RNA polymerase inhibitor, a thiazolide, sustained release thiazolide, a nucleoside analog, and an interferon-alpha.

4. A pharmaceutical composition for treating a host having a viral infection for a virus from the Flaviviridae family of viruses, comprising an inhibiting agent, wherein the inhibiting agent has the following structure:

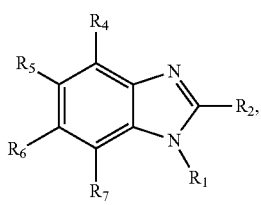

wherein $R_1$ is

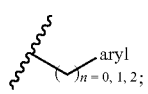

wherein $R_2$ is

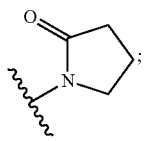

n is 1, and where X is

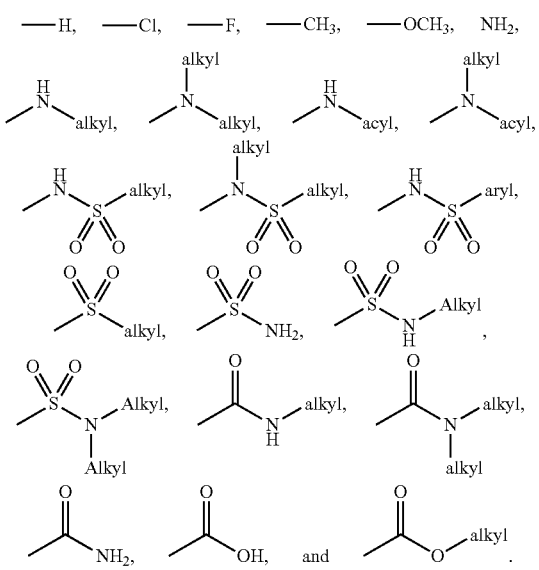

wherein each of $R_4$-$R_7$ is independently selected from the group consisting of:

—H, —Cl, —F, —CH$_3$, —OCH$_3$, NH$_2$, and various substituted amino, sulfonamide, sulfonyl, amide, and ester groups as shown.

5. The pharmaceutical composition of claim 4, further comprising a second agent for treating the viral infection.

6. The pharmaceutical composition of claim 5, wherein the second agent is selected from the group consisting of: an anti-HCV therapeutic agent, an HCV NS3 protease inhibitor, an HCV NS5B RNA-dependent RNA polymerase inhibitor, a thiazolide, a sustained release thiazolide, a nucleoside analog, and an interferon-alpha.

* * * * *

                              SEQUENCE LISTING

<160> NUMBER OF SEQ ID NOS: 19

<210> SEQ ID NO 1
<211> LENGTH: 341
<212> TYPE: DNA
<213> ORGANISM: Hepatitis C Virus

<400> SEQUENCE: 1
gccagccccc tgatgggggc gacactccac catgaatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gataaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac c                        341

<210> SEQ ID NO 2
<211> LENGTH: 341
<212> TYPE: DNA
<213> ORGANISM: Hepatitis C Virus

<400> SEQUENCE: 2
cggucggggg acuaccccg cugugaggug guacuuagug aggggacacu ccuugaugac       60 agaagucgu cuuucgcaga ucgguaccgc aaucauacuc acagcacguc ggagguccug      120 gggggagg cccucucggu aucaccagac gccuuggcca cucaugugc cuuaacgguc       180 cugcuggccc aggaaagaac cuauuugggc gaguuacgga ccucuaaacc cgcacggggg    240
cguucugacg aucggcucau cacaacccag cgcuuuccgg aacaccauga cggacuaucc    300
cacgaacgcu cacggggccc uccagagcau cuggcacgug g                        341

<210> SEQ ID NO 3
<211> LENGTH: 526
<212> TYPE: DNA
<213> ORGANISM: Hepatitis C Virus

<400> SEQUENCE: 3
agacccaagc tggctagcgt ttaaacttaa gcttggtacc gagctcggat ccactagtcc      60
agtgtggtgg aattctgcag atatcataat acgactcact atagccagcc cccgattggg     120
ggcgacactc caccatagat cactccctg tgaggaacta ctgtcttcac gcagaaagcg     180
tctagccatg gcgttagtat gagtgtcgtg cagcctccag gacccccct cccgggagag     240 ccatagtggt ctgcggaacc ggtgagtaca ccggaattgc caggacgacc gggtcctttc    300
ttggatcaac ccgctcaatg cctggagatt tgggcgtgcc ccgcgagac tgctagccga    360
```

-continued

```
gtagtgttgg gtcgcgaaag gccttgtggt actgcctgat agggtgcttg cgagtgcccc      420
gggaggtctc gtagaccgtg caccatgagc acgaatccta aacctcaaag aaaaaccaaa      480
gggcgcgcca tggatcgata tccagcacag tggcggccgc tcgagt                    526
```

```
<210> SEQ ID NO 4
<211> LENGTH: 526
<212> TYPE: DNA
<213> ORGANISM: Hepatitis C Virus

<400> SEQUENCE: 4
```

```
acucgagcgg ccgccacugu gcuggauauc gauccauggc gcgcccuuug guuuucuuu       60 gagguuuagg auucgugcuc auggugcacg gucuacgaga ccucccgggg cacucgcaag     120 caccucuauca ggcaguacca caaggccuuu cgcgacccaa cacuacucgg cuagcagucu    180
cgcgggggca cgcccaaauc uccaggcauu gagcgggttg auccaagaaa ggacccgguc    240
guccuggcaa uuccgugua cucaccgguu ccgcagacca cuauggcucu cccggggagg     300 ggguccugg  aggcugcacg acacucauac uaacgccaug gcuagacgcu uucugcguga    360
agacaguagu uccucacagg ggagugaucu augguggagu gucgcccca aucggggcu      420 ggcuauagug agucguauua ugauaucugc agaauuccac cacacuggac uaguggaucc    480
gagcucggua ccaagcuuaa guuuaaacgc uagccagcuu ggucu                    526
```

```
<210> SEQ ID NO 5
<211> LENGTH: 16
<212> TYPE: PRT
<213> ORGANISM: Artificial Sequence
<220> FEATURE:
<223> OTHER INFORMATION: RNA binding domain

<400> SEQUENCE: 5
```

```
Thr Arg Gln Ala Arg Arg Asn Arg Arg Arg Arg Trp Arg Glu Arg Gln
1               5                   10                  15
```

```
<210> SEQ ID NO 6
<211> LENGTH: 17
<212> TYPE: PRT
<213> ORGANISM: Artificial Sequence
<220> FEATURE:
<223> OTHER INFORMATION: RNA binding domain

<400> SEQUENCE: 6
```

```
Ala Leu Gly Ile Ser Tyr Gly Arg Lys Lys Arg Arg Gln Arg Arg Arg
1               5                   10                  15

Pro
```

```
<210> SEQ ID NO 7
<211> LENGTH: 18
<212> TYPE: PRT
<213> ORGANISM: Artificial Sequence
<220> FEATURE:
<223> OTHER INFORMATION: RNA binding domain

<400> SEQUENCE: 7
```

```
Met Asp Ala Gln Thr Arg Arg Arg Glu Arg Arg Ala Glu Lys Gln Ala
1               5                   10                  15

Gln Trp
```

```
<210> SEQ ID NO 8
<211> LENGTH: 18
```

```
<212> TYPE: PRT
<213> ORGANISM: Artificial Sequence
<220> FEATURE:
<223> OTHER INFORMATION: RNA binding domain

<400> SEQUENCE: 8

Gly Thr Ala Lys Ser Arg Tyr Lys Ala Arg Arg Ala Glu Leu Ile Ala
1               5                   10                  15

Glu Arg

<210> SEQ ID NO 9
<211> LENGTH: 18
<212> TYPE: PRT
<213> ORGANISM: Artificial Sequence
<220> FEATURE:
<223> OTHER INFORMATION: RNA binding domain

<400> SEQUENCE: 9

Gly Asn Ala Lys Thr Arg Arg His Glu Arg Arg Arg Lys Leu Ala Ile
1               5                   10                  15

Glu Arg

<210> SEQ ID NO 10
<211> LENGTH: 38
<212> TYPE: PRT
<213> ORGANISM: Artificial Sequence
<220> FEATURE:
<223> OTHER INFORMATION: RNA binding domain

<400> SEQUENCE: 10

Met Asp Asn Arg Ile Thr Asp Leu Leu Thr Arg Ser Gly Tyr Leu Arg
1               5                   10                  15

Thr Ser Glu Pro Arg Gly Ala Gly Gln Gln Leu Val Val His Ala Val
                20                  25                  30

Ala Gly Ala Gly Lys Thr
                35

<210> SEQ ID NO 11
<211> LENGTH: 8
<212> TYPE: PRT
<213> ORGANISM: Artificial Sequence
<220> FEATURE:
<223> OTHER INFORMATION: RNA binding domain

<400> SEQUENCE: 11

Asn Glu Arg Asn Arg Arg Ser Asn
1               5

<210> SEQ ID NO 12
<211> LENGTH: 57
<212> TYPE: PRT
<213> ORGANISM: Artificial Sequence
<220> FEATURE:
<223> OTHER INFORMATION: RNA binding domain

<400> SEQUENCE: 12

Arg Arg His Val Gly Pro Gly Glu Gly Ala Val Gln Trp Met Asn Arg
1               5                   10                  15

Leu Ile Ala Phe Ala Ser Arg Gly Asn His Val Ser Pro Thr His Tyr
                20                  25                  30

Val Pro Glu Ser Asp Ala Ala Ala Arg Val Thr Ala Ile Leu Ser Ser
                35                  40                  45

Leu Thr Val Thr Gln Leu Leu Arg Arg
```

```
                    50                  55

<210> SEQ ID NO 13
<211> LENGTH: 261
<212> TYPE: PRT
<213> ORGANISM: Artificial Sequence
<220> FEATURE:
<223> OTHER INFORMATION: membrane protein sequence

<400> SEQUENCE: 13

Ala Ser His Leu Pro Tyr Ile Glu Gln Gly Met Met Leu Ala Glu Gln
1               5                   10                  15

Phe Lys Gln Lys Ala Leu Gly Leu Leu Gln Thr Ala Ser Arg His Ala
            20                  25                  30

Glu Val Ile Thr Pro Ala Val Gln Thr Asn Trp Gln Lys Leu Glu Val
        35                  40                  45

Phe Trp Ala Lys His Met Trp Asn Phe Ile Ser Gly Ile Gln Tyr Leu
    50                  55                  60

Ala Gly Leu Ser Thr Leu Pro Gly Asn Pro Ala Ile Ala Ser Leu Met
65                  70                  75                  80

Ala Phe Thr Ala Ala Val Thr Ser Pro Leu Thr Thr Gly Gln Thr Leu
                85                  90                  95

Leu Phe Asn Ile Leu Gly Gly Trp Val Ala Ala Gln Leu Ala Ala Pro
            100                 105                 110

Gly Ala Thr Ala Phe Val Gly Ala Gly Leu Ala Gly Ala Ala Ile
            115                 120                 125

Gly Ser Val Gly Leu Gly Lys Val Leu Val Asp Ile Leu Ala Gly Tyr
130                 135                 140

Gly Ala Gly Val Ala Gly Ala Leu Val Ala Phe Lys Ile Met Ser Gly
145                 150                 155                 160

Glu Val Pro Ser Thr Glu Asp Leu Val Asn Leu Leu Pro Ala Ile Leu
                165                 170                 175

Ser Pro Gly Ala Leu Val Val Gly Val Val Ser Ala Ala Ile Leu Arg
            180                 185                 190

Arg His Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
    210                 215                 220

Pro Glu Ser Asp Ala Ala Arg Val Thr Ala Ile Leu Ser Ser Leu
225                 230                 235                 240

Thr Val Thr Gln Leu Leu Arg Arg Leu His Gln Trp Ile Ser Ser Glu
                245                 250                 255

Cys Thr Thr Pro Cys
            260

<210> SEQ ID NO 14
<211> LENGTH: 17
<212> TYPE: RNA
<213> ORGANISM: Artificial Sequence
<220> FEATURE:
<223> OTHER INFORMATION: RNA probe sequence

<400> SEQUENCE: 14
auuuauuuau uuauuua                                              17

<210> SEQ ID NO 15
<211> LENGTH: 17
<212> TYPE: RNA
```

```
<213> ORGANISM: Artificial Sequence
<220> FEATURE:
<223> OTHER INFORMATION: RNA probe sequence

<400> SEQUENCE: 15
cuuucuuucu uucuuuc                                                    17

<210> SEQ ID NO 16
<211> LENGTH: 8
<212> TYPE: PRT
<213> ORGANISM: Artificial Sequence
<220> FEATURE:
<223> OTHER INFORMATION: nucleotide binding sequence

<400> SEQUENCE: 16

Gly Ser Val Gly Gly Leu Gly Lys
1               5

<210> SEQ ID NO 17
<211> LENGTH: 10
<212> TYPE: PRT
<213> ORGANISM: Artificial Sequence
<220> FEATURE:
<223> OTHER INFORMATION: Epitope tag

<400> SEQUENCE: 17

Cys Tyr Pro Tyr Asp Val Pro Asp Tyr Ala
1               5                   10

<210> SEQ ID NO 18
<211> LENGTH: 21
<212> TYPE: PRT
<213> ORGANISM: Artificial Sequence
<220> FEATURE:
<223> OTHER INFORMATION: Epitope tag

<400> SEQUENCE: 18

Cys Cys Ala Ala Ala Thr Cys Thr Cys Ala Gly Gly Cys Ala Thr
1               5                   10                  15

Thr Gly Ala Gly Cys
            20

<210> SEQ ID NO 19
<211> LENGTH: 24
<212> TYPE: PRT
<213> ORGANISM: Artificial Sequence
<220> FEATURE:
<223> OTHER INFORMATION: Epitope tag

<400> SEQUENCE: 19

Cys Ala Cys Cys Gly Gly Ala Ala Thr Thr Gly Cys Cys Ala Gly Gly
1               5                   10                  15

Ala Cys Gly Ala Cys Cys Gly Gly
            20
```